United States Patent
Oakey et al.

(10) Patent No.: US 12,077,638 B2
(45) Date of Patent: Sep. 3, 2024

(54) METHODS OF GENERATING MICROPARTICLES AND POROUS HYDROGELS USING MICROFLUIDICS

(71) Applicant: University of Wyoming, Laramie, WY (US)

(72) Inventors: John Oakey, Laramie, WY (US); Kaspars Krutkramelis, Laramie, WY (US); Bingzhao Xia, Calamvale (AU)

(73) Assignee: University of Wyoming, Laramie, WY (US)

( * ) Notice: Subject to any disclaimer, the term of this patent is extended or adjusted under 35 U.S.C. 154(b) by 0 days.

(21) Appl. No.: 15/335,184

(22) Filed: Oct. 26, 2016

(65) Prior Publication Data
US 2017/0145169 A1    May 25, 2017

Related U.S. Application Data

(60) Provisional application No. 62/285,352, filed on Oct. 26, 2015.

(51) Int. Cl.

| | |
|---|---|
| *A61K 36/9066* | (2006.01) |
| *A61K 9/50* | (2006.01) |
| *A61K 35/12* | (2015.01) |
| *A61L 27/16* | (2006.01) |
| *A61L 27/18* | (2006.01) |
| *A61L 27/38* | (2006.01) |
| *A61L 27/52* | (2006.01) |
| *A61L 27/56* | (2006.01) |
| *B01F 23/41* | (2022.01) |
| *B01F 25/433* | (2022.01) |
| *B01F 33/3011* | (2022.01) |
| *B01J 2/06* | (2006.01) |
| *B01J 13/00* | (2006.01) |
| *B01J 19/00* | (2006.01) |
| *C08F 2/32* | (2006.01) |
| *C08F 2/48* | (2006.01) |
| *C08J 3/075* | (2006.01) |
| *C08J 9/26* | (2006.01) |
| *C12N 5/00* | (2006.01) |
| *C08F 216/12* | (2006.01) |
| *C08F 222/10* | (2006.01) |

(52) U.S. Cl.
CPC .............. *C08J 3/075* (2013.01); *A61K 9/5026* (2013.01); *A61K 35/12* (2013.01); *A61L 27/16* (2013.01); *A61L 27/18* (2013.01); *A61L 27/38* (2013.01); *A61L 27/52* (2013.01); *A61L 27/56* (2013.01); *B01F 23/41* (2022.01); *B01F 25/4331* (2022.01); *B01F 33/3011* (2022.01); *B01J 2/06* (2013.01); *B01J 13/0052* (2013.01); *B01J 19/0093* (2013.01); *C08F 2/32* (2013.01); *C08F 2/48* (2013.01); *C08J 9/26* (2013.01); *C12N 5/0012* (2013.01); *B01J 2219/00792* (2013.01); *B01J 2219/00936* (2013.01); *C08F 216/125* (2013.01); *C08F 222/102* (2020.02); *C08J 2201/046* (2013.01); *C08J 2205/022* (2013.01); *C08J 2207/10* (2013.01); *C08J 2335/02* (2013.01); *C08J 2345/00* (2013.01)

(58) Field of Classification Search
None
See application file for complete search history.

(56) References Cited

U.S. PATENT DOCUMENTS

| | | | |
|---|---|---|---|
| 5,573,934 | A | 11/1996 | Hubbell et al. |
| 5,631,079 | A | 5/1997 | Gutman et al. |
| 2002/0193546 | A1 | 12/2002 | Freeman et al. |
| 2003/0045597 | A1 | 3/2003 | Randolph et al. |
| 2007/0242111 | A1 | 10/2007 | Pamula et al. |
| 2011/0104052 | A1 | 5/2011 | Barnett et al. |
| 2011/0129941 | A1 | 6/2011 | Kumacheva et al. |
| 2020/0254417 | A1 | 8/2020 | Oakey et al. |

FOREIGN PATENT DOCUMENTS

| | | |
|---|---|---|
| CN | 101018816 A | 8/2007 |
| CN | 102171234 A | 8/2011 |
| CN | 102898134 A | 1/2013 |
| WO | WO 2019/079414 A1 | 4/2019 |

OTHER PUBLICATIONS

Zhou et al. (MEMS 2015, Estoril, Portugal, Jan. 18-22, 2015, pp. 472-475) Core-Shell Microparticle . . . .*
Ligon et al. ( Chem. Rev., 114, 557-589, 2014) Strategies to Reduce . . . .*
Fairbanks (Biomaterials, 30(35), 6702-6707, 2009 ) Photoinitiated polymerization . . . .*
Sia et al. (Electrophoresis, 24, 3563-3576, 2003) Microfluidic devices . . . .*
Lemke et al. ( J. Am. Chem. Soc., 131(38), 13610-13612, 2009), Microfluidic Device for Single-Molecule Experiments with Enhanced Photostability.*
Jiang et al. (Journal of Colloid and Interface Science, vol. 448, Jun. 15, 2015, pp. 275-279) Microfluidic generation of uniform water droplets using gasas the continuous phase.*
Krutkramelis et al. (18th International Conference on Miniaturized, Systems for Chemistry and Life Sciences, Oct. 26-30, 2014) Microfluidic Hydrogel Particle . . . .*

(Continued)

*Primary Examiner* — Tigabu Kassa
(74) *Attorney, Agent, or Firm* — Leydig, Voit & Mayer, Ltd.

(57) ABSTRACT

Provided herein are methods utilizing microfluidics for the oxygen-controlled generation of microparticles and hydrogels having controlled microparticle sizes and size distributions and products from provided methods. The included methods provide the generation of microparticles by polymerizing an aqueous solution dispersed in a non-aqueous continuous phase in an oxygen-controlled environment. The process allows for control of size of the size of the aqueous droplets and, thus, control of the size of the generated microparticles which may be used in biological applications.

27 Claims, 25 Drawing Sheets

(56) References Cited

OTHER PUBLICATIONS

Abbyad et al. (2010) "Sickling of red blood cells through rapid oxygen exchange in microfluidic drops," Lab Chip. 10:2505-2509.
Ahmed (Mar. 2015) "Hydrogel: Preparation, characterization, and applications: A Review," Journal of Advanced Research. 6(2):105-121.
Anderson et al. (May 2011) "The performance of human mesenchymal stem cells encapsulated in cell-degradable polymer-peptide hydrogels," Biomaterials. 32(14):3564-3574.
Andrzejewska (2001) "Photopolymerization kinetics of multifunctional monomers," Progress in Polymer Science. 26:605-665.
Appleyard et al. (2011) "Bar-coded hydrogel microparticles for protein detection: synthesis, assay and scanning," Nature Protocols. 6:1761-1774.
Armstrong (1994) "The analysis of free radicals, lipid peroxides, antioxidant enzymes and compounds related to oxidative stress as applied to the clinical chemistry laboratory," Free radicals in diagnostic medicine. 366:43-58.
Bamford et al. (Aug. 1949) "The autoxidation of tetralin," Proceedings of the Royal Society of London A: Mathematical, Physical and Engineering Sciences. 198(1053):252-267.
Benoit et al. (Oct. 2008) "Small functional groups for controlled differentiation of hydrogel-encapsulated human mesenchymal stem cells," Nature Materials. 7(10):816-823.
Benya et al. (Aug. 1982) "Dedifferentiated chondrocytes reexpress the differentiated collagen phenotype when cultured in agarose gels," Cell. 30(1):215-224.
Billiet et al.(2012) "A review of trends and limitations in hydrogel-rapid prototyping for tissue engineering," Biomaterials. 33:6020-6041.
Bryant et al. (2000) "Cytocompatibility of UV and visible light photoinitiating systems on cultured NIH/3T3 fibroblasts in vitro," Journal of Biomaterials Science, Polymer. 11:439-457.
Bryant et al. (2004) "Encapsulating chondrocytes in degrading PEG hydrogels with high modulus: engineering gel structural changes to facilitate cartilaginous tissue production," Biotechnology and Bioengineering. 86(7):747-755.
Burdick et al. (2002) "Photoencapsulation of osteoblasts in injectable RGD-modified PEG hydrogels for bone tissue engineering," Biomaterials. 23:4315-4323.
Burkoth et al. (2000) "A review of photocrosslinked polyanhydrides: in situ forming degradable networks," Biomaterials. 21:2395-2404.
Cabiscol et al. (Mar. 2000) "Oxidative stress in bacteria and protein damage by reactive oxygen species," International Microbiology. 3(1):3-8.
Choh et al. (Apr. 11, 2011) "Facile synthesis and characterization of disulfide-cross-linked hyaluronic acid hydrogels for protein delivery and cell encapsulation," Biomacromolecules. 12(4):1126-1136.
Chou et al. (Oct. 2009) "Characterization of photocrosslinked alginate hydrogels for nucleus pulposus cell encapsulation," J. Biomed. Mater. Res. 91A(1):187-194.
Cox et al. (1986) "Oxygen diffusion in poly(dimethyl siloxane) using fluorescence quenching. I. Measurement technique and analysis," Journal of Polymer Science Part A: Polymer Chemistry. 24:621-636.
De Geest et al. (2005) "Synthesis of Monodisperse Biodegradable Microgels in Microfluidic Devices," Langmuir. 21:10275-10279.
Decker et al. (1985) "Kinetic approach of oxygen inhibition in ultraviolet-and laser-induced polymerizations," Macromolecules. 18:1241-1244.
Dendukuri et al. (2007) "Stop-flow lithography in a microfluidic device," Lab Chip 7:818.
Dendukuri et al. (Oct. 21, 2008) "Modeling of Oxygen-Inhibited Free Radical Photopolymerization in a PDMS Microfluidic Device," Macromolecules. 41(2):8547-8556.
Du et al. (2008) "Directed assembly of cellladen microgels for fabrication of 3D tissue constructs," Proceedings of the National Academy of Sciences. 105(28):9522-9527.
Duffy et al. (1999) "Rapid prototyping of microfluidic switches in poly (dimethyl siloxane) and their actuation by electroosmotic flow," Journal of Micromechanics and Microengineering. 9:211.
Esterbauer (1992) "The role of lipid peroxidation and antioxidants in oxidative modification of LDL," Free Radical Biology and Medicine. 13(4):341-390.
Fairbanks et al. (Oct. 7, 2009) "Photoinitiated polymerization of PEG-diacrylate with lithium phenyl-2, 4, 6-trimethylbenzoylphosphinate: polymerization rate and cytocompatibility," Biomaterials. 30(35):6702-6707.
Fairbanks et al. (Dec. 28, 2009) "A Versatile Synthetic Extracellular Matrix Mimic via Thiol-Norbornene Photopolymerization," Adv. Mater. 21(48):5005-5010.
Ford (2006) "A macroporous hydrogel for the coculture of neural progenitor and endothelial cells to form functional vascular networks in vivo," Proceedings of the National Academy of Sciences. 103:2512-2517.
Gobaa et al. (Oct. 9, 2011) "Artificial niche microarrays for probing single stem cell fate in high throughput," Nat Meth. 8(11):949-955.
Gref et al. (Mar. 18, 1994) "Biodegradable long-circulating polymeric nanospheres," Science. 263(5153):1600-1603.
Grigoriev et al. (2006) "Chaotic mixing in microdroplets," Lab Chip. 6:1369-1372.
Guo et al. (Jan. 2010) "Repair of osteochondral defects with biodegradable hydrogel composites encapsulating marrow mesenchymal stem cells in a rabbit model," Acta Biomaterialia. 6(1):39-47.
Hamilton et al. (2013) "Development of 3-D Hydrogel Culture Systems With On Demand Cell Separation," Biotechnology Journal. 8:485-495.
Hazel et al. (2013) "Changes in cytoplasmic volume are sufficient to drive spindle scaling," Science. 342:853-856.
Hoyle et al. (Feb. 22, 2010) "Thiol-Ene Click Chemistry," Angew. Chem. Int. 49(9):1540-1573.
Hwang et al. (2009) "Stop-Flow Lithography for the Production of Shape-Evolving Degradable Microgel Particles," Journal of the American Chemical Society. 131:4499-4504.
Hwang et al. (2010) "Benchtop fabrication of PDMS microstructures by an unconventional photolithographic method," Biofabrication. 2:045001-045001.
Imlay (1988) "DNA damage and oxygen radical toxicity," Science. 240(4857):1302- 1309.
Jariwala et al. (2011) "Modeling effects of oxygen inhibition in mask-based stereolithography," Rapid Prototyping Journal. 17:168-175.
Jiang et al. (Nov. 25, 2017) "A microfluidic-based cell encapsulation platform to achieve high long-term cell viability in photopolymerized PEGNB hydrogel microspheres," J. Mater. Chem. B. 5:173-180.
Kar et al. (Jan. 2016) "Poly(ethylene glycol) hydrogels with cell cleavable groups for autonomous cell delivery," Biomaterials. 77:186-197.
Karihaloo et al. (Jul. 17, 2013) "J. Honeybee combs: how the circular cells transform into rounded hexagons," J R Soc Interface. 10(86):20130299-20130299.
Klein et al. (May 21, 2015) "Droplet barcoding for single-cell transcriptomics applied to embryonic stem cells," Cell. 161(5):1187-1201.
Kloxin et al. (Dec. 2010) "Synthesis of photodegradable hydrogels as dynamically tunable cell culture platforms," Nature Protocols. 5:1867-1887.
Kloxin et al. (Apr. 2009) "Photodegradable hydrogels for dynamic tuning of physical and chemical properties," Science. 324(5923):59-63.
Kloxin et al. (Aug. 2010) "Mechanical properties of cellularly responsive hydrogels and their experimental determination," Adv. Mater. 22(31):3484-3494.
Krutkramelis et al. (Feb. 24, 2016) "Monodisperse polyethylene glycol diacrylate hydrogel microsphere formation by oxygen-controlled photopolymerization in a microfluidic device," Lab Chip. 16:1457-1465.
Kubie (1927) "The solubility of O2, CO2, and N2 in mineral oil and the transfer of carbon dioxide from oil to air," Journal of Biological Chemistry. 72(2):545-548.

(56) References Cited

OTHER PUBLICATIONS

Kuck et al. (2008) "Photopolymerization as an innovative detection technique for low-density microarrays," Biotech. 45:179-186.
Kumacheva et al. (2003) "Two-Dimensional Colloid Crystals Obtained by Coupling of Flow and Confinement," Phys. Rev. Lett. 91:128301.
Lacy et al. (1991) "Maintenance of normoglycemia in diabetic mice by subcutaneous xenografts of encapsulated islets," Science. 254(5039):1782-1784.
Ladygin et al. (1984) "Kinetics of the Reactions of Peroxy-Radicals Formed by the Electronirradiation of Normal and Cyclic Hydrocarbons in the Presence of Oxygen," High Energy Chemistry. 18(4):241-244.
Lam et al. (Mar. 2016) "Evaluation of cell-laden polyelectrolyte hydrogels incorporating poly(L-Lysine) for applications in cartilage tissue engineering," Biomaterials. 83:332-346.
Lanasa et al. (2011) "Presence of pores and hydrogel composition influence tensile properties of scaffolds fabricated from well-defined sphere templates," Journal of Biomedical Materials Research Part B: Applied Biomaterials. 96B:294-302.
Landfester et al. (2010) "Chemical Design of Responsive Microgels," Adv Polym Sci. 234:39-63.
Lebourg et al. (2007) "Biodegradable polycaprolactone scaffold with controlled porosity obtained by modified particle-leaching technique," J Mater Sci: Mater Med. 19:2047-2053.
Lewis et al. (2010) "Microfluidic Fabrication of Hydrogel Microparticles Containing Functionalized Viral Nanotemplates," Langmuir. 26:13436-13441.
Li et al. (2014) "Micropatterned cell-cell interactions enable functional encapsulation of primary hepatocytes in hydrogel microtissues," Tissue Engineering. 20A(15-16):2200-2212.
Ligon et al. (2014) "Strategies to Reduce Oxygen Inhibition in Photoinduced Polymerization," Chem. Rev. 114:557-589.
Lin et al. (Dec. 2011) "PEG hydrogels formed by thiol-ene photoclick chemistry and their effect on the formation and recovery of insulin-secreting cell spheroids," Biomaterials. 32(36):9685-9695.
Lin et al. (Jul. 24, 2009) "Controlling Affinity Binding with Peptide-Functionalized Poly(ethylene glycol) Hydrogels," Adv. Funct. Mater. 19(14):2325-2331.
Lindner et al. (Mar. 1995) "Implantation of encapsulated catecholamine and GDNF-producing cells in rats with unilateral dopamine depletions and parkinsonian symptoms," Experimental Neurology. 132(1):62-76.
Lu et al. (Jan. 27, 2006) "A digital micro-mirror device-based system for the microfabrication of complex, spatially patterned tissue engineering scaffolds," J. Biomed. Mater. Res. 77A(2):396-405.
Ma et al. (2014) "On the flow topology inside droplets moving in rectangular microchannels," Lab Chip. 1-10.
Macosko et al. (May 21, 2015) "Highly Parallel Genome-wide Expression Profiling of Individual Cells Using Nanoliter Droplets," Cell. 161(5):1202-1214.
Mahoney et al. (Apr. 2006) "Three-dimensional growth and function of neural tissue in degradable polyethylene glycol hydrogels," Biomaterials. 27(10):2265-2274.
Majima et al. (Oct. 1991) "Phenyl-2,4,6-trimethylbenzoylphosphinates as water-soluble photoinitiators. Generation and reactivity of O $\dot{P}(C_6H_5)(O^-)$ radical anions," Macromolecular Chemistry and Physics. 192(10):2307-2315.
Mann et al. (2001) "Smooth muscle cell growth in photopolymerized hydrogels with cell adhesive and proteolytically degradable domains: synthetic ECM analogs for tissue engineering," Biomaterials. 22:3045-3051.
Mayo (1968) "Free radical autoxidations of hydrocarbons," Accounts of Chemical Research. 1(7):193-201.
Metters et al. (2000) "A Statistical Kinetic Model for the Bulk Degradation of PLA-b-PEG- b-PLA Hydrogel Networks," J. Phys. Chem. B. 104:7043-7049.
Monette et al. (Jan. 2016) "Chitosan thermogels for local expansion and delivery of tumor-specific T lymphocytes towards enhanced cancer immunotherapies," Biomaterials. 75:237-249.

Mooney et al. (2011) "Control of Neural Cell Composition in Poly(Ethylene Glycol) Hydrogel Culture with Soluble Factors," Tissue Engineering. 17A:2805-2815.
Mũnoz et al. (Mar. 3, 2014) "Gelatin hydrogels formed by orthogonal thiol-norbornene photochemistry for cell encapsulation," 2:1063-1072.
Murua et al. (Dec. 8, 2008) "Cell microencapsulation technology: towards clinical application," Journal of Controlled Release. 132(2):76-83.
Nair et al. (2012) "UV-Induced Radical Photo-Polymerization: A Smart Tool for Preparing Polymer Electrolyte Membranes for Energy Storage Devices," Membranes. 2:687-704.
Nguyen et al. (2002) "Photopolymerizable hydrogels for tissue engineering applications," Biomaterials. 23:4307-4314.
Nicodemus et al. (2008) "Cell encapsulation in biodegradable hydrogels for tissue engineering applications," Tissue Engineering. 14B:149-165.
O'Brien (Feb. 6, 2006) "Modeling the Effect of Oxygen on Photopolymerization Kinetics," Macromol. Theory Simul. 15(2):176-182.
O'Brien et al. (Feb. 2, 2006) "Oxygen inhibition in thiol-acrylate photopolymerizations," J. Polym. Sci. Polym. Chem. 44(6):2007-2014.
Olabisi et al. (2010) "Hydrogel Microsphere Encapsulation of a Cell-Based Gene Therapy System Increases Cell Survival of Injected Cells, Transgene Expression, and Bone Volume in a Model of Heterotopic Ossification," Tissue Engineering. 16A:3727-3736.
Oliveira et al. (2011) "Polymer-based microparticles in tissue engineering and regenerative medicine," Biotechnol Progress. 27:897-912.
Panda et al. (Jul. 2008) "Stop-flow lithography to generate cell-laden microgel particles," Lab Chip. 8(7):1056-6.
Patel et al. (Aug. 1, 2011) "Hydrogel Biomaterials," Ch. 14, In; Biomedical Engineering—Frontiers and Challenges. pp. 275-296.
Peppas (2000) "Hydrogels in pharmaceutical formulations," European Journal of Pharmaceutics and Biopharmaceutics. 50:27-46.
Perez et al. (Oct. 10, 2011) "A collagen peptide-based physical hydrogel for cell encapsulation," Macromol. Biosci. 11(10):1426-1431.
Pregibon et al. (2007) "Multifunctional encoded particles for highthroughput biomolecule analysis," Science. 315:1393.
Priola et al. (Sep. 1993) "Properties of polymeric films obtained from U.V. cured poly(ethylene glycol) diacrylates," Polymer. 34(17):3653-3657.
Reece et al. (Aug. 2016) "Microfluidic techniques for high throughput single cell analysis," Current Opinion in Biotechnology. 40:90-96.
Rice et al. (2004) "Encapsulating chondrocytes in copolymer gels: Bimodal degradation kinetics influence cell phenotype and extracellular matrix development," J. Biomed. Mater. Res. 70A:560-568.
Riess et al. (1982) "Solubility and Transport Phenonena in Perfluorochemicals Relevant to Blood Substitution and Other Biomedical Applications," Pure and Applied Chemistry. 54(12):2383-2406.
Roberts et al. (Dec. 2013) "Comparison of photopolymerizable thiol-ene PEG and acrylate-based PEG hydrogels for cartilage development," Biomaterials. 34(38):9969-9979.
Ross et al. (1979) "Rate Constants for Reactions of Inorganic Radicals in Aqueous Solution," US Department of Commerce, National Bureau of Standards. pp. 1-55.
Sawhney et al. (1993) "Bioerodible hydrogels based on photopolymerized poly(ethylene glycol)-co-poly (alpha-hydroxy acid) diacrylate macromers," Macromolecules. 26:581-587.
Seliktar (Jun. 1, 2012) "Designing cell-compatible hydrogels for biomedical applications," Science. 336(6085):1124-1128.
Shih et al. (Jun. 18, 2012) "Cross-Linking and Degradation of Step-Growth Hydrogels Formed by Thiol-Ene Photoclick Chemistry," Biomacromolecules. 13(7):2003-2012.
Shiku et al. (Jan. 21, 2006) "Oxygen permeability of surface-modified poly(dimethylsiloxane) characterized by scanning electrochemical microscopy," Chem. Lett. 35(2):234-235.

(56) References Cited

OTHER PUBLICATIONS

Siltanen et al. (Apr. 1, 2016) "Microfluidic fabrication of bioactive microgels for rapid formation and enhanced differentiation of stem cell spheroids," Acta Biomaterialia. 34:125-132.

Sivadas et al. (2011) "Inhalable, bioresponsive microparticles for targeted drug delivery in the lungs," Journal of Pharmacy and Pharmacology. 63:369-375.

Smaller et al. (1968) "Electron Paramagnetic Resonance Studies of Transient Free Radicals Produced by Pulse Radiolysis," Argonne National Lab, III.

Stadtman (2003) "Free radical-mediated oxidation of free amino acids and amino acid residues in proteins," Amino acids. 25(3-4):207-218.

Subramaniam et al. (Jan. 2016) "Hydroxyapatite-calcium sulfate-hyaluronic acid composite encapsulated with collagenase as bone substitute for alveolar bone regeneration," Biomaterials. 74:99-108.

Suh et al. (2011) "Using Stop-Flow Lithography to Produce Opaque Microparticles: Synthesis and Modeling," Langmuir. 27(2):13813-13819.

Tang et al. (2011) "A PDMS viscometer for assaying endoglucanase activity," Analyst. 136:1222-1226.

Thorsen et al. (2001) "Dynamic Pattern Formation in a Vesicle-Generating Microfluidic Device," Phys. Rev. Lett. 86:4163-4166.

Tsang et al. (2004) "Three-dimensional tissue fabrication," Advanced Drug Delivery Reviews. 56:1635-1647.

Vanapalli et al. (2008) "Fluidic Assembly and Packing of Microspheres in Confined Channels," Langmuir. 24:3661-3670.

Vegas et al. (Mar. 2016) "Long-term glycemic control using polymer-encapsulated human stem cell-derived beta cells in immune-competent mice," Nat Med. 22(3):306-311.

Vermue (1994) "Tetralin and oxygen transfer in the liquid-impelled loop reactor," Bioprocess Engineering. 11(6):224-228.

Weber et al. (Jul. 2007) "The effects of cell-matrix interactions on encapsulated beta-cell function within hydrogels functionalized with matrix-derived adhesive peptides," Biomaterials. 28(19):3004-3011.

Weber et al. (Nov. 19, 2008) "Cell-Matrix Interactions Improve 13-Cell Survival and Insulin Secretion in Three-Dimensional Culture," Tissue Engineering. 14A(12): 1959-1968.

Whittemore (1995) "A detailed analysis of hydrogen peroxide-induced cell death in primary neuronal culture," Neuroscience. 67(4):921-932.

Wiseman et al. (Jan. 1, 1996) "Damage to DNA by reactive oxygen and nitrogen species: role in inflammatory disease and progression to cancer," Biochemical Journal. 313(1):17-29.

Xia et al. (2008) "Soft Lithography," Annual Review of Materials Science. 28:153-184.

Xia et al. (2016) "Oxygen-Purged Microfluidic Device to Enhance Cell Viability in Photopolymerized PEG Hydrogel Microparticles," Biomacromolecules. 17(7):2459-2465.

Yadavalli et al. (2004) "Microfabricated protein-containing poly (ethylene glycol) hydrogel arrays for biosensing," Sensors and Actuators B: Chemical. 97(2):290-297.

Yang et al. (Oct. 2005) "The effect of incorporating RGD adhesive peptide in polyethylene glycol diacrylate hydrogel on osteogenesis of bone marrow stromal Cells," Biomaterials. 26(30):5991-5998.

Yu et al. (2001) "Photopolymerization behavior of di(meth)acrylate oligomers," Journal of Materials Science. 36:3599-3605.

Zhu (2010) "Bioactive modification of poly(ethylene glycol) hydrogels for tissue engineering," Biomaterials. 31:4639-4656.

International Search Report corresponding to International Patent Application No. PCT/US2016/058897, dated Jan. 17, 2017.

European Extended Search Report issued in EP 16860701.8, dated Jun. 3, 2019, related to the present application, 7 pp.

International Preliminary Report on Patentability issued in PCT/US2016/058897, dated May 1, 2018, 8 pp.

O'Brien et al. (Mar. 3, 2006) "Impact of Oxygen on Photopolymerization Kinetics and Polymer Structure," Macromolecules. 39:2501-2506.

O'Brien & Bowman (2004) "The Impact of Oxygen on Photopolymerization Kinetics," Technical Proceedings, 9 pp.

European Office Action issued in 16860701-8 on Feb. 13, 2020.

An et al. (Jul. 2014) "Synthesis of colloidal microgels using oxygen-controlled flow lithography," Soft Matter 10(38): 7595-7605.

Ansari et al. (Mar. 2016) "Muscle Tissue Engineering Using Gingival Mesenchymal Stem Cells Encapsulated in Alginate Hydrogels Containing Multiple Growth Factors," Annals of Biomedical Engineering 44(6):1908-1920.

Chinese Office Action, dated Jun. 3, 2020, in Chinese Patent Application No. 201680075469.9, 31 pp.

European Office Action, dated Jun. 23, 2020, corresponding to European Patent Application No. 16860701.8, 4 pp.

Shin et al. (publicly available Jun. 2014) "Photodegradable Hydrogels for Capture, Detection, and Release of Live Cells," Angew. Chemi. Int. (Jul. 2014) 53(31): 8221-8224.

Ahmad et al. (Apr. 2015) "Hydrogel Microparticles as an Emerging Tool in Pharmaceutical Field: a Review," Adv. Polym. Technol. 35 (2), 121-128.

Anderson et al. (2000) "Fabrication of Topologically Complex Three-Dimensional Microfluidic Systems in PDMS by Rapid Prototyping," Anal. Chem. 72 (14), 3158-3164.

Anna et al. (2006) "Microscale Tipstreaming in a Microfluidic Flow Focusing Device," Phys. Fluids 18 (12), 121512, 13 pp.

Burdick et al. (2004) "Fabrication of Gradient Hydrogels Using a Microfluidics/Photopolymerization Process," Langmuir 20 (13), 5153-5156.

Buwalda et al. (2017) "Hydrogels for Therapeutic Delivery: Current Developments and Future Directions," Biomacromolecules 18 (2), 316-330.

Colley et al. (2002) "Probing the Reactivity of Photoinitiators for Free Radical Polymerization: Time-Resolved Infrared Spectroscopic Study of Benzoyl Radicals," J. Am. Chem. Soc. 124 (50), 14952-14958.

Debroy et al. (2017) "Fabrication of Non-Spherical Hydrogel Particles for Drug Delivery," poster for NIH Western Region IDeA conference, Oct. 18, 2017.

Debroy et al. (2018) "Interfacially-mediated oxygen inhibition for precise and continuous poly (ethylene glycol) diacrylate (PEGDA) particle fabrication," Journal of Colloid and Interface Science 510, 334-344, available online Sep. 22, 2017.

Debroy et al. (2018) "Supplementary Material for Interfacially-mediated oxygen inhibition for precise and continuous poly (ethylene glycol) diacrylate (PEGDA) particle fabrication," Journal of Colloid and Interface Science, available online at https://doi.org/10.1016/j.jcis.2017.09.081, 10 pp.

DeForest et al. (2009) "Sequential Click Reactions for Synthesizing and Patterning Three-Dimensional Cell Microenvironments," Nature Materials 8 (8), 659-664.

Du et al. (1995) "ABA Type Copolymers of Lactide with Poly(Ethylene Glycol). Kinetic, Mechanistic, and Model Studies," Macromolecules 28, 2124-2132.

Hagel et al. (2013) "Diffusion and Interaction in PEG-DA Hydrogels," Biointerphases 8 (36), 1-9.

Holtze et al. (2008) "Biocompatible Surfactants for Water-in-Fluorocarbon Emulsions," Lab Chip 8 (10), 1632-1639.

International Preliminary Report on Patentability issued in No. PCT/US2018/056237, dated Apr. 30, 2020, 9 pp.

International Search Report and Written Opinion corresponding to International Patent Application No. PCT/US2018/056237, dated Dec. 21, 2018, 11 pp.

Joao (2016) "Inverted Colloidal Crystal Scaffolds: New Substitutes for Bone Tissue Engineering," Doctoral dissertation, Universidade NOVA de Lisboa (Portugal) [online], retrieved on Nov. 27, 2018 from https://run.unl.pt/handle/10362/19891. Dec. 2016, p. 25, 8 pp.

Jockusch et al. (2001) "Photochemistry and Photophysics of A-Hydroxy Ketones," Macromolecules 34 (6), 1619-1626.

Kenney et al. (1998) "Mutation Typing Using Electrophoresis and Gel-Immobilized Acrydite," BioTechniques 25 (3), 516-521.

Kharkar et al. (Jul. 2015) "Design of Thiol- and Light-Sensitive Degradable Hydrogels Using Michael-Type Addition Reactions," Polym. Chem. 6 (31), 5565-5574.

(56) References Cited

OTHER PUBLICATIONS

Kim et al. (2007) "Controlled Production of Emulsion Drops Using an Electric Field in a Flow-Focusing Microfluidic Device," Appl. Phys. Lett. 91 (13), 133106-3.
Kim et al. (2014) "Droplet Microfluidics for Producing Functional Microparticles," Langmuir 30 (6), 1473-1488, published online Nov. 8, 2013.
Lee et al. (2010) "Development of Macroporous Poly(Ethylene Glycol) Hydrogel Arrays Within Microfluidic Channels," Biomacromolecules 11 (12), 3316-3324.
McDonald et al. (2002) "Poly(Dimethylsiloxane) as a Material for Fabricating Microfluidic Devices," Acc. Chem. Res. 35 (7), 491-499.
Melville et al. (1954) "Biological Properties of Biotin D- and L-Sulfoxides," J. Biol. Chem. No. 208, 503-512.
Mexal et al. (1975) "Oxygen Availability in Polyethylene Glycol Solutions and Its Implications in Plant-Water Relations," Plant Physiology No. 55, 20-24.
Miller et al. (2003) "N-Vinylamides and Reduction of Oxygen Inhibition in Photopolymerization of Simple Acrylate Formulations," In Photoinitiated Polymerization; ACS Symposium Series; 847, pp. 2-14.
Peppas et al. (1989) "A Simple Equation for the Description of Solute Release. III. Coupling of Diffusion and Relaxation," International Journal of Pharmaceutics No. 57, 169-172.
Peppas et al. (2006) "Hydrogels in Biology and Medicine: From Molecular Principles to Bionanotechnology," Adv. Mater. 18 (11), 1345-1360.
Rehman et al. (1999) "Immobilization of Acrylamide-Modified Oligonucleotides by Co-Polymerization," Nucleic Acids Res 27 (2), 649-655.
Saenz et al. (1999) "Ceramic Biomaterials: an Introductory Overview," Journal of Materials Education 21: 297-306.
Sakhalkar (2005) "Enhanced Adhesion of Ligand-Conjugated Biodegradable Particles to Colitic Venules," The FASEB Journal 1-19.
Sang et al. (2013) "A Microfluidic Technique for Generating Monodisperse Submicron-Sized Drops," RSC Advances 3 (7), 2330-2336.
Shim et al. (Mar. 2015) "Dynamic designing of microstructures by chemical gradient-mediated growth," Nature Communications 6, 6584. https://doi.org/10.1038/ncomms7584, 7 pp.
Tan et al. (2004) "Design of Microfluidic Channel Geometries for the Control of Droplet Volume, Chemical Concentration, and Sorting," Lab Chip 4 (4), 292-298.
Teh et al. (2008) "Droplet Microfluidics," Lab Chip 8 (2), 198-220.
West et al. (1999) "Polymeric Biomaterials with Degradation Sites for Proteases Involved in Cell Migration," Macromolecules 32 (1), 241-244.
Yang et al. (Jul. 2016) "Spatially Patterned Matrix Elasticity Directs Stem Cell Fate," Proc Natl Acad Sci USA 113 (31), E4439-E4445.
Chinese Office Action, dated Feb. 24, 2021, corresponding to Chinese Patent Application No. 201680075469.9, 21 pages.
U.S. Appl. No. 16/647,869, filed Oct. 17, 2018.
An et al. (2013) "Synthesis of biomimetic oxygen-carrying compartmentalized microparticles using flow lithography," Lab Chip. 13:4765-4774.
Anseth et al. (2002) "In Situ Forming Degradable Networks and Their Application in Tissue Engineering and Drug Delivery," Journal of Controlled Release 78, 199-209.
Australian First Examination Report, dated issued Aug. 23, 2021, corresponding to Australian Application Serial No. 2016346332, 2 pp.
Beamish et al. (2009) "The Effects of Monoacrylated Poly(Ethylene Glycol) on the Properties of Poly(Ethylene Glycol) Diacrylate Hydrogels Used for Tissue Engineering," J. Biomed. Mater. Res. 9999A, NA-NA.
Becker et al. (2006) "The Role of Hydroquinone Monomethyl Ether in the Stabilization of Acrylic Acid," Chem. Eng. Technol. 29 (10), 1227-1231.
Bong et al. (2010) "Magnetic Barcoded Hydrogel Microparticles for Multiplexed Detection," Langmuir 26 (11), 8008-8014.
Buenger et al. (2012) "Hydrogels in Sensing Applications," Progress in Polymer Science 37 (12), 1678-1719.
Burton et al. (1981) "Autoxidation of Biological Molecules. 1. The Antioxidant Activity of Vitamin E and Related Chain-Breaking Phenolic Antioxidants in Vitro," J. Am. Chem. Soc. No. 103, 6472-6477.
Chinese Office Action, dated Aug. 4, 2021, corresponding to Chinese Patent Application No. 201680075469.9, 9 pp.
Choi et al. (2012) "Multiplexed Detection of mRNA Using Porosity-Tuned Hydrogel Microparticles," Anal. Chem. 84 (21), 9370-9378.
Chong (1969) "Oxygen Consumption During Induction Period," Journal of Applied Polymer Science 13, 241-247.
Cruise et al. (1998) "Characterization of Permeability and Network Structure of Interfacially Photopolymerized Poly(Ethylene Glycol) Diacrylate Hydrogels," Biomaterials No. 19, 1287-1294.
Dang et al. (2012) "Preparation of Monodisperse PEG Hydrogel Microparticles Using a Microfluidic Flow-Focusing Device," Journal of Industrial and Engineering Chemistry 18 (4), 1308-1313.
Datta (2007) "Characterization of Polyethylene Glycol Hydrogels for Biomedical Applications," LSU Master's Theses, 3502. 117 pp. https://digitalcommons.lsu.edu/gradschool_theses/3502.
Gou et al. (2006) "Consumption of the Molecular Oxygen in Polymerization Systems Using Photosensitized Oxidation of Dimethylanthracene," Chemical Engineering Communications 193 (5), 620-627.
Griffith (2000) "Polymeric Biomaterials," Acta mater 2000, No. 48, 263-277.
Hamidi et al. (2008) "Hydrogel Nanoparticles in Drug Delivery," Advanced Drug Delivery Reviews 60 (15), 1638-1649.
Harrane et al. (2011) "PLA-Based Biodegradable and Tunable Soft Elastomers for Biomedical Applications," Biomed. Mater. 6 (6), 065006-065012.
He et al. (2004) "Concentrating Solutes and Nanoparticles Within Individual Aqueous Microdroplets," Anal. Chem. 76 (5), 1222-1227.
Helgeson et al. (2011) "Hydrogel Microparticles From Lithographic Processes: Novel Materials for Fundamental and Applied Colloid Science," Current Opinion in Colloid & Interface Science 16 (2), 106-117.
Höfer et al. (2008) "Oxygen Scavengers and Sensitizers for Reduced Oxygen Inhibition in Radical Photopolymerization," J. Polym. Sci. A Polym. Chem. 46 (20), 6916-6927.
Hoffman (2012) "Hydrogels for Biomedical Applications," Advanced Drug Delivery Reviews 64, 18-23.
Hristova et al. (2005) "Addition of Benzoyl Radicals to Butyl Acrylate: Absolute Rate Constants by Time-Resolved EPR," Macromolecules 38 (18), 7714-7720.
Jeong et al. (2012) "Controlled Generation of Submicron Emulsion Droplets via Highly Stable Tip-Streaming Mode in Microfluidic Devices," Lab Chip 12 (8), 1446-1453.
Jockusch et al. (1998) "Phosphinoyl Radicals: Structure and Reactivity. a Laser Flash Photolysis and Time-Resolved ESR Investigation," J. Am. Chem. Soc. 120 (45), 11773-11777.
Jockusch et al. (1999) "Radical Addition Rate Constants to Acrylates and Oxygen: A-Hydroxy and A-Amino Radicals Produced by Photolysis of Photoinitiators," J. Am. Chem. Soc. 121 (16), 3921-3925.
Kim et al. (2013) "Mathematical Analysis of Oxygen Transfer Through Polydimethylsiloxane Membrane Between Double Layers of Cell Culture Channel and Gas Chamber in Microfluidic Oxygenator," Microfluid Nanofluid 15 (3), 285-296.
Kizilel et al. (2006) "Mathematical Model for Surface-Initiated Photopolymerization of Poly(Ethylene Glycol) Diacrylate," Macromol. Theory Simul. 15 (9), 686-700.
Le Goff et al. (Nov. 2015) "Hydrogel Microparticles for Biosensing," European Polymer Journal 72 (C), 386-412.
Lee et al. (2009) "Poly(Ethylene Glycol) Hydrogel Microparticles Containing Enzyme-Fluorophore Conjugates for the Detection of Organophosphorus Compounds," Sensors and Actuators B: Chemical 137 (1), 209-214.

(56) References Cited

OTHER PUBLICATIONS

Lewis et al. (2010) "Fabrication of Uniform DNA-Conjugated Hydrogel Microparticles via Replica Molding for Facile Nucleic Acid Hybridization Assays," Anal. Chem. 82 (13), 5851-5858.

Liu et al. (May 2016) "Methods for Generating Hydrogel Particles for Protein Delivery," Annals of Biomedical Engineering 44 (6), 1946-1958.

Luchini et al. (2008) "Smart Hydrogel Particles: Biomarker Harvesting: One-Step Affinity Purification, Size Exclusion, and Protection Against Degradation," Nano Lett. 8 (1), 350-361.

Lustig et al. (1988) "Solute Diffusion in Swollen Membranes. IX. Scaling Laws for Solute Diffusion in Gels," Journal of Applied Polymer Science 735-747.

Mahadik et al. (2014) "Microfluidic Generation of Gradient Hydrogels to Modulate Hematopoietic Stem Cell Culture Environment," Adv. Healthcare Mater. 3 (3), 449-458.

Merkel et al. (2000) "Gas Sorption, Diffusion, and Permeation in Poly(Dimethylsiloxane)," Journal of Polymer Science Part B Polymer Physics 38, 415-434.

Niinomi (2008) "Metallic Biomaterials" J Artif Organs, 11 (3), 105-110.

Oh et al. (2008) "The Development of Microgels/Nanogels for Drug Delivery Applications," Progress in Polymer Science 33 (4), 448-477.

Ramanan et al. (2006) "Development of a Temperature-Sensitive Composite Hydrogel for Drug Delivery Applications," Biotechnol Progress 22 (1), 118-125.

Saunders et al. (1999) "Microgel Particles as Model Colloids: Theory, Properties and Applications," Advances in Colloid and Interface Science No. 80, 1-25.

Scaiano et al. (2012) "Photochemical Norrish Type I Reaction as a Tool for Metal Nanoparticle Synthesis: Importance of Proton Coupled Electron Transfer," Chem. Commun. 48 (40), 4798-4808.

Scherzer et al. (2005) "Temperature Dependence of the Oxygen Solubility in Acrylates and Its Effect on the Induction Period in UV Photopolymerization," Macromol. Chem. Phys. 206 (2), 240-245.

Tan et al. (2005) "Microfluidic Separation of Satellite Droplets as the Basis of a Monodispersed Micron and Submicron Emulsification System," Lab Chip 5 (10), 1178-1183.

Turturro et al. (2013) "Kinetic Investigation of Poly(Ethylene Glycol) Hydrogel Formation via Perfusion-Based Frontal Photopolymerization: Influence of Free-Radical Polymerization Conditions on Frontal Velocity and Swelling Gradients," Macromolecular Reaction Engineering 7 (2), 107-115.

Xia et al. (Jul. 2017) "Cytocompatible Cell Encapsulation via Hydrogel Photopolymerization in Microfluidic Emulsion Droplets," Biomicrofluidics 11 (4), 044102-044111.

Zhu et al. (2017) "Passive and Active Droplet Generation with Microfluidics: a Review," Lab Chip 17 (1), 34-75.

\* cited by examiner

METHODS OF GENERATING MICROPARTICLES AND POROUS HYDROGELS USING MICROFLUIDICS

CROSS-REFERENCE TO RELATED APPLICATIONS

This application claims the benefit of and priority to U.S. Provisional Patent Application No. 62/285,352, filed Oct. 26, 2015, which is hereby incorporated by reference in its entirety.

STATEMENT REGARDING FEDERALLY SPONSORED RESEARCH OR DEVELOPMENT

This invention was made with U.S. Government Support under grant (BBBE 1254608) by the National Science Foundation Faculty Early Career Development (CAREER) Program, and by (P20RR016474 and P20GM103432) the NIH-funded Wyoming IDeA Networks of Biomedical Research Excellence program to J. Oakey. The U.S. Government has certain rights in the invention.

BACKGROUND OF INVENTION

PEG-based hydrogels have become widely used as drug delivery and tissue scaffolding materials. Common among PEG hydrogel-forming polymers are photopolymerizable acrylates in the form of polyethylene glycol diacrylate (PEGDA). Microfluidics and microfabrication technologies have recently enabled the miniaturization of PEGDA structures, thus enabling many possible applications for nano- and micro-structured hydrogels. The presence of oxygen, however, dramatically inhibits the photopolymerization of PEGDA, which in turn frustrates hydrogel formation in environments of persistently high oxygen concentration. Using PEGDA that has been encapsulated within a fluorocarbon oil with polydimethylsiloxane (PDMS) microfluidic devices, we show that polymerization is completely inhibited below critical droplet diameters. By developing an integrated model incorporating reaction kinetics and oxygen diffusion, we demonstrate that the critical droplet size is largely determined by the oxygen transport rate, which is dictated by the oxygen saturation concentration of the continuous oil phase. To overcome this fundamental limitation, we present a nitrogen micro-jacketed microfluidic device that establishes an oxygen-reduced environment, which enables the stable, rapid on-chip photopolymerization of microscale PEGDA emulsion droplets.

Photopolymerization also plays an important role in numerous industrial and research applications, including biomaterials for cell encapsulation and delivery. A common design of hydrogel materials for cell encapsulation is the use of diacrylated macromers. The presence of oxygen is known to inhibit the photopolymerization of PEGDA, but does not require mitigation on the macroscale. reactions, and most notably, it limits polymerization carried out in air permeable polydimethylsiloxane (PDMS) microfluidic devices. In this example, we present an innovative nitrogen micro-jacketed microfluidic device that creates oxygen-controlled environment in PDMS for a stable particle photopolymerization on a chip.

Inverse colloidal crystals (ICCs) are the product of a lost wax fabrication method in which colloidal particles are assembled into ordered matrices in the presence of a liquid continuous phase. Following solidification of the continuous phase, particles are subsequently extracted, leaving behind a structured pore network. ICCs have been developed for a variety of scientific and technological applications, yet their utility remains limited by harsh processing conditions required to solubilize particles for pore framework formation. In this example, we present a new approach to ICC construction based upon photodegradable polyethylene glycol diacrylate particle synthesis. Because the degradation of particulate phase requires only optical illumination, particle assemblies can be eroded within tightly confining microchannels, creating microfluidic-integrated ICCs. Using this approach, photodegradable particle assemblies are used to pattern porous polyethylene glycol hydrogel network structure and interconnectivity. The non-invasive, gentle erosion of photodegradable PEG particles allows secondary objects to be embedded within the pores of the ICC. This approach is also facile, gentle and cytocompatible, indicating that it holds great potential for structuring functional biomaterials.

SUMMARY OF THE INVENTION

Provided herein are methods utilizing microfluidics for the oxygen-controlled generation of microparticles and hydrogels having controlled microparticle sizes and size distributions and products from provided methods. The included methods provide the generation of microparticles by polymerizing an aqueous solution dispersed in a non-aqueous continuous phase in an oxygen-controlled environment. The process allows for control of size of the size of the aqueous droplets and, thus, control of the size of the generated microparticles which may be used in biological applications. The ability to select the size of the microparticles is beneficial for a variety of applications, including drug screening, drug delivery, transplantation studies, tissue engineering, and stem cell therapies. The provided methods are versatile and can utilize a variety of polymer systems and initiators. For example, the provided methods may utilize photopolymerization or chemical polymerization depending on the desired function.

The ability to control the amount of oxygen present in the system is beneficial during polymerization. For example, an excess amount of oxygen may chemically interfere with the initiator, inhibiting polymerization. Further, oxygen present during a polymerization reaction may generate oxygen-containing species which may be harmful or toxic to biological materials which are later introduced to the microspheres. Thus, the ability to regulate the amount of oxygen in both the non-aqueous phase and the aqueous phase provides benefits to polymerization chemistry and biological compatibility.

In an aspect, provided is a method preparing a plurality of microparticles in a microfluidics device in an oxygen-controlled environment comprising the steps of: a) providing a continuous phase comprising a non-aqueous liquid and a dispersed phase comprising an aqueous solution comprising a monomer or a macromer, and an initiator; b) forming a composition comprising microdroplets of the aqueous phase and the non-aqueous liquid; c) purging the composition comprising the microdroplets and the non-aqueous liquid with an oxygen-free gas; and d) polymerizing the monomer or the macromer in the microdroplets to form microparticles.

In an embodiment, for example, the oxygen-free gas is nitrogen. In embodiments, the oxygen-free gas is provided at a pressure selected from the range of 0.1 atm to 10 atm, greater than or equal to 1 atm or optionally, greater than or equal to 2 atm. In embodiments, the microdroplets have a surface area to volume ratio of less than or equal to 3/radius of the microdroplet, a surface area to volume ratio of greater than or equal 3/radius of the microdroplet or, optionally, selected from the range of 1/radius of the microdroplet to 5/radius of the microdroplet.

In an embodiment, the initiator is a chemical initiator or a photoinitiator. In an embodiment, for example, the initiator is a photoinitiator and the step of polymerizing the monomer or macromer is carried out in the presence of ultraviolet light. In an embodiment, the photoinitiator is lithium phenyl-2,4,6-trimethylbenzoylphosphinate (LAP) or Irgacure 1173.

In embodiments, the non-aqueous fluid has an oxygen solubility selected from the range of 0.01 mol/m$^3$ to 4 mol/m$^3$, a solubility greater than or equal to 0.5 mol/m$^3$, or optionally, greater than or equal to 1 mol/m$^3$. In an embodiment, wherein the non-aqueous liquid comprises a fluorocarbon oil, for example, a segregated hydrofluoroether. In an embodiment, the non-aqueous liquid is a segregated hydrofluoroether such as 3M® Novec 7500, 3M®Fluoroinert FC 40, 3M®Fluoroinert FC 70 or 3M® Fluoroinert FC 77. In embodiments, the non-aqueous liquid further comprises a surfactant, for example, a polyhexafluoropropylene oxide containing polymer. In an embodiment, the surfactant is provided at a concentration selected from the range of 0.1% to 4%, a concentration greater than or equal to 1%, or optionally, greater than or equal to 2%. In an embodiment, for example, the polyhexafluoropropylene oxide containing polymer is a Dolomite FluoroPEG surfactant, RAN Biotechnologies FluoroPEG surfactant or Krytox FSL 157.

The provided methods may be used to generate hydrogels including hydrogels with photodegradable microparticles. In an embodiment, for example, the microparticles are hydrogel microparticles. In an embodiment, the microparticles, the monomer and/or the macromer are photodegradable. In an embodiment, aid aqueous solution comprises a macromer, and the macromer is a polyethylene glycol (PEG)-based macromer. In an embodiment, the PEG-based photodegradable macromer has a molecular weight selected from the range of 200 to 20,000 Daltons. In an embodiment, for example, the PEG-based macromer is a PEG-diacrylate (PEGDA) macromer or a PEG-norbornene (PEGNB) macromer.

The provided methods and products may be useful to generate micro- or nano-sized microparticles and hydrogels. The controlled size and/or size distribution of the particles may allow for particles corresponding to the diameter of individual cells, allowing for the encapsulation or entrainment of cells within a hydrogel or scaffold. In an embodiment, the microparticles have a mean diameter of less than or equal to 1000 μm, of less than or equal to 500 μm, less than or equal to 100 μm, less than or equal to 60 μm or, for example, less than or equal to 50 μm.

In an embodiment, the step of purging the composition reduces the amount of oxygen in the composition by selected from the range of 1% to 90%. In embodiment, the step of purging the composition reduces the amount of oxygen in the composition by selected from the range of 5% to 50%, greater than or equal to 25% or, for example, greater than or equal to 50%. In an embodiment, the step of purging the composition reduces the amount of oxygen in the non-aqueous liquid by selected from the range of 1% to 90%. In embodiment, the step of purging the composition reduces the amount of oxygen in the non-aqueous liquid by selected from the range of 5% to 50%, greater than or equal to 25% or, for example, greater than or equal to 50%.

In an embodiment, for example, the step of purging provides the oxygen-free gas is in communication with the composition for selected from the range of 1 μs to 10 s. In embodiments, for example, the step of purging provides the oxygen-free gas in communication with the composition for greater than or equal to 1 s. In an embodiment, the step of purging the composition further comprises a membrane between the composition and the oxygen-free gas. In an embodiment, the membrane has a thickness selected from the range of 10 μm to 500 μm. In an embodiment, for example, the membrane is a polydimethylsiloxane membrane.

In embodiments, the provided methods further comprise the steps of: e) at least partially encapsulating the microparticles within a non-photodegradable polymer, wherein the microparticles are photodegradable; and f) photodegrading the photodegradable microparticles to produce a composite porous hydrogel. In embodiments, the provided methods further comprise the steps of: g) contacting the composite porous hydrogel with a biological material, thereby distributing the biological material into pores of the composite porous hydrogel. In an embodiment, for example, the biological material is a biologically viable material.

In an embodiment, for example, the biologically viable material comprises cells. In embodiments, the pores of the composite porous hydrogel have lateral dimension to receive an individual cell. In embodiments, said biologically viable material is selected from the group consisting of: mesenchymal stem cells, β cells, satellite muscle cells, proteins, therapeutic small molecules, imaging molecules, secondary nanoparticles and any combination thereof. In embodiments, the composition is a water in oil emulsion, for example, a micro-emulsion or a nano-emulsion.

In an aspect, provided is a plurality of microparticles prepared by the process of: a) providing a continuous phase comprising a non-aqueous liquid and a dispersed phase comprising an aqueous solution comprising a monomer or a macromer, and an initiator; b) forming a composition comprising microdroplets of the aqueous phase and the non-aqueous liquid; c) purging the composition comprising the microdroplets and the non-aqueous liquid with an oxygen-free gas; and d) polymerizing the monomer or the macromer in the microdroplets to form microparticles.

In embodiments, the process to prepare the plurality of microparticles includes parameters (e.g. oxygen reduction, microparticle size, pressure, etc.), materials (e.g. non-aqueous liquids, surfactants, monomers, macromers, biological materials, etc.), and/or additional process steps (e.g. partially encapsulating the microparticles, photodegrading the microparticles, contacting with a biological material, etc.) as described herein.

In an aspect, provided is a method for preparing a composite hydrogel with a biological material comprising the steps of: a) providing a continuous phase comprising a non-aqueous liquid and a dispersed phase comprising an aqueous solution comprising a photodegradable monomer or a photodegradable macromer, and an initiator; b) forming a composition comprising microdroplets of the aqueous phase and the non-aqueous liquid; c) purging the composition comprising the microdroplets and the non-aqueous liquid with an oxygen-free gas; d) polymerizing the photodegradable monomer or the photodegradable macromer of the microdroplets to form photodegradable microparticles; e) at least partially encapsulating the photodegradable microparticles within a non-photodegradable polymer; f) photodegrading the photodegradable microparticles to produce a composite porous hydrogel; and g) contacting the composite porous hydrogel with a biologically material, thereby capturing a portion of the biological material in the composite porous hydrogel.

In embodiments, method of preparing a composite hydrogel with biological material includes parameters (e.g. oxygen reduction, microparticle size, pressure, etc.), materials (e.g. non-aqueous liquids, surfactants, monomers, macromers, biological materials etc.), and/or additional process steps (e.g. partially encapsulating the microparticles, photodegrading the microparticles, contacting with a biological material, etc.) as described herein.

In an embodiment, for example, the biological material is viable. In embodiments, the biological material is a plurality of viable cells. In an embodiment, for example, the composite hydrogel has a plurality of pores each sized to receive an individual cell and the step of contacting the composite porous hydrogel results in a portion of the plurality of cells each encapsulated in a pore of the composite porous hydrogel.

In an aspect, provided is a method for encapsulating a biological material in microparticles comprising the steps of: a) providing a continuous phase comprising a non-aqueous liquid and a dispersed phase comprising an aqueous solution comprising a monomer or a macromer, the biological material and an initiator; b) forming a composition comprising microdroplets of the aqueous phase and the non-aqueous liquid; c) purging the composition comprising the microdroplets and the non-aqueous liquid with an oxygen-free gas; and d) polymerizing the monomer or the macromer in the microdroplets to form microparticles containing biological material.

In embodiments, the method for encapsulating biological material in microparticles includes parameters (e.g. oxygen reduction, microparticle size, pressure, etc.), materials (e.g. non-aqueous liquids, surfactants, monomers, macromers, biological materials etc.), and/or additional process steps (e.g. partially encapsulating the microparticles, photodegrading the microparticles, contacting with a biological material, etc.) as described herein.

In an embodiment, the biological material is a viable biological material. In an embodiment, for example, the biological material comprises a single cell. In embodiments, single cell refers to individual microdroplets having only a single cell per microdroplet. In an embodiment, a plurality of the microdroplets each contain one of the cells. In an embodiment, for example, the microparticles are photodegradable; and the provided method further comprises the steps of: e) at least partially encapsulating the microparticles within a non-photodegradable polymer, and f) photodegrading the photodegradable microparticles to produce a composite porous hydrogel having a plurality of pores containing a biological material.

In an aspect, provided is a method for preparing an inverse colloidal crystal containing biological material comprising the steps of: a) providing a continuous phase comprising a non-aqueous liquid and a dispersed phase comprising an aqueous solution comprising a photodegradable monomer or a photodegradable macromer, said biological material and an initiator; b) forming a composition comprising microdroplets of said aqueous phase and said non-aqueous liquid; c) purging said composition comprising said microdroplets and the non-aqueous liquid with an oxygen-free gas; d) polymerizing said monomer or said macromer in said microdroplets to form photodegradable microparticles containing biological material; e) at least partially encapsulating said photodegradable microparticles within a non-photodegradable polymer, and photodegrading said photodegradable microparticles to produce an inverse colloidal crystal having a plurality of pores containing a biological material.

In embodiments, the method for preparing an inverse colloidal crystal containing a biological material includes parameters (e.g. oxygen reduction, microparticle size, pressure, etc.), materials (e.g. non-aqueous liquids, surfactants, monomers, macromers, biological materials etc.), and/or additional process steps (e.g. partially encapsulating the microparticles, photodegrading the microparticles, contacting with a biological material, etc.) as described herein.

In an embodiment, for example, said biological material is a viable cell and a plurality of said microdroplets each contain a single viable cell. In embodiments, said non-photodegradable polymer is provided in the liquid phase and said step of photodegrading simultaneously photocures said non-photodegradable polymer.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

DETAILED DESCRIPTION OF THE INVENTION

Figure 1:
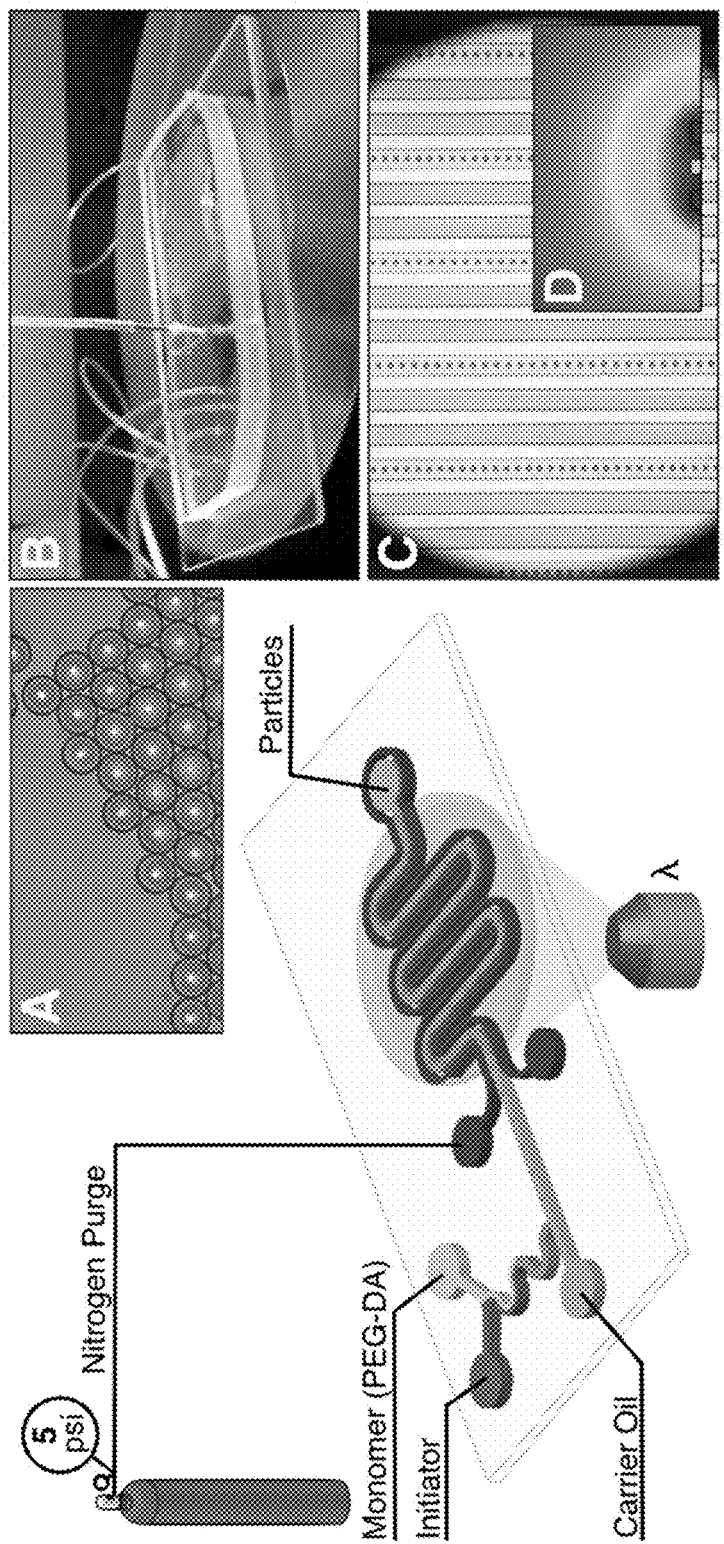
FIG. 1. illustrates hydrogel microparticle fabrication via microfluidic emulsification, nitrogen purging and photopolymerization.

In general, the terms and phrases used herein have their art-recognized meaning, which can be found by reference to standard texts, journal references and contexts known to those skilled in the art. The following definitions are provided to clarify their specific use in the context of the invention.

As used herein, the term "polymer" refers to a molecule composed of repeating structural units connected by covalent chemical bonds often characterized by a substantial number of repeating units (e.g., equal to or greater than 3 repeating units, optionally, in some embodiments equal to or greater than 10 repeating units, in some embodiments greater or equal to 30 repeating units) and a high molecular weight (e.g. greater than or equal to 20,000 Da, in some embodiments greater than or equal to 50,000 Da or greater than or equal to 100,000 Da). Polymers are commonly the polymerization product of one or more monomer or macromer precursors. The term polymer includes homopolymers, or polymers consisting essentially of a single repeating monomer subunit. The term polymer also includes copolymers which are formed when two or more different types of monomers are linked in the same polymer. Useful polymers include organic polymers or inorganic polymers that may be in amorphous, semi-amorphous, crystalline or semi-crystalline states.

"Monomer" and/or "Macromer" each refer to a reagent which can undergo polymerization under appropriate conditions. A monomer or macromer reagent comprises at least one monomer or macromer molecule, where a monomer or macromer molecule is a molecule which can undergo polymerization, thereby contributing constitutional units to the structure of a polymer or oligomer. In an embodiment, a monomer or macromer reagent may be represented by an average or dominant chemical structure and comprise monomer molecules having that chemical structure but may also contain components with other chemical structures. For example, a monomer or macromer reagent may comprise impurities having chemical structures other than the average or dominant structure of the reagent. Macromer may refer to a reagent which is polymeric, e.g., has a number of repeating units but may further undergo polymerization to form a polymer of macromer repeating units. In embodiments, for example, macromer refers to reagents having a high molecular weight (e.g. greater than or equal to 200 Da, in some embodiments greater than or equal to 1000 Da or greater than or equal to 10,000 Da).

"Non-photodegradable polymer" refers to a polymer is that is not photodegradable under selected exposure conditions, e.g., selected wavelength range, intensity, power or a combination thereof. In an embodiment, for example, a non-photodegradable polymer refers to a polymer that does not degrade under the conditions present to degrade photodegradable polymers as described herein.

"Microparticles" refers to particles including polymers, having relatively small dimensions including diameter, radius, height, width, depth, etc. In embodiments, for example, microparticles refer to particles having a lateral dimension (e.g. diameter) of less than or equal to equal to 1 mm. In some embodiments, microparticles refers to particles having an average or mean diameter of less than or equal to 500 µm, less than or equal to 100 µm, or less than or equal to 50 µm. In some embodiments, microparticles are microspheres. In some embodiments, microparticles refer to particles having lateral dimensions selected from the range of 10 nm to 1000 µm, preferably for some embodiments, 10 nm to 100 µm.

"Microdroplets" refer to microparticles in the liquid phase. For example, in some embodiments, microdroplets refer to droplets having a mean or average diameter of less than or equal to 500 µm, less than or equal to 100 µm, or less than or equal to 50 µm. In embodiments, microdroplets refer to liquids in a suspension, for example an emulsion. In an embodiment, microdroplets refer to aqueous liquids suspended in a non-aqueous liquid. In some embodiments, microdroplets refer to particles having lateral dimensions selected from the range of 10 nm to 1000 µm, preferably for some embodiments, 10 nm to 100 µm.

"Oxygen-free gas" refers to any fluid in the vapor phase containing substantially no oxygen. In embodiments, for example, oxygen-free gas refers to a gas having less than 10% oxygen, less than 1% oxygen, less than 0.1% oxygen. In some embodiments, for example, oxygen-free gas refers to a gas has less than 0.01% oxygen by partial pressure or concentration.

"Oxygen-controlled environment" refers to a vessel or microfluidic device wherein the amount of oxygen present within the device or in communication with the reagents can be altered and/or preselected. In embodiments, oxygen-controlled environment refers to a microfluidic device in which the oxygen content may be reduced, for example, by purging or displacing oxygen with an oxygen-free gas.

"Hydrogel" refers to an at least partially hydrophilic substance having characterized by high water absorbency. In embodiments, hydrogel comprises an at least partially hydrophilic polymer, superabsorbent polymer or biomacromolecule, for example in a network configuration. Hydrogels may be characterized as a water swollen but insoluble substance. In embodiments, for example, hydrogels may absorb water greater than or equal to 10 times the hydrogel weight, greater than or equal to 50 times the hydrogel weight or, optionally, greater than or equal to 100 times the hydrogel weight.

FIG. 1. Provides A) a Schematic of on-chip "one pot" hydrogel microparticle fabrication via microfluidic emulsification, nitrogen purging and photopolymerization. B) Fully polymerized hydrogel particles (r~50 µm). C) A photograph of the integrated microfluidic device in operation. UV exposure of the droplet transfer serpentine belt can be observed on the right hand side of the device. D) Micrograph of mono-disperse particles flowing through a serpentine belt (ivory) surrounded by nitrogen micro-jacket (purple). E) COMSOL simulated cross-sectional diffusion profile of nitrogen (blue) displacing air (red) in PDMS that was reached after ~10 min.

Figure 2:
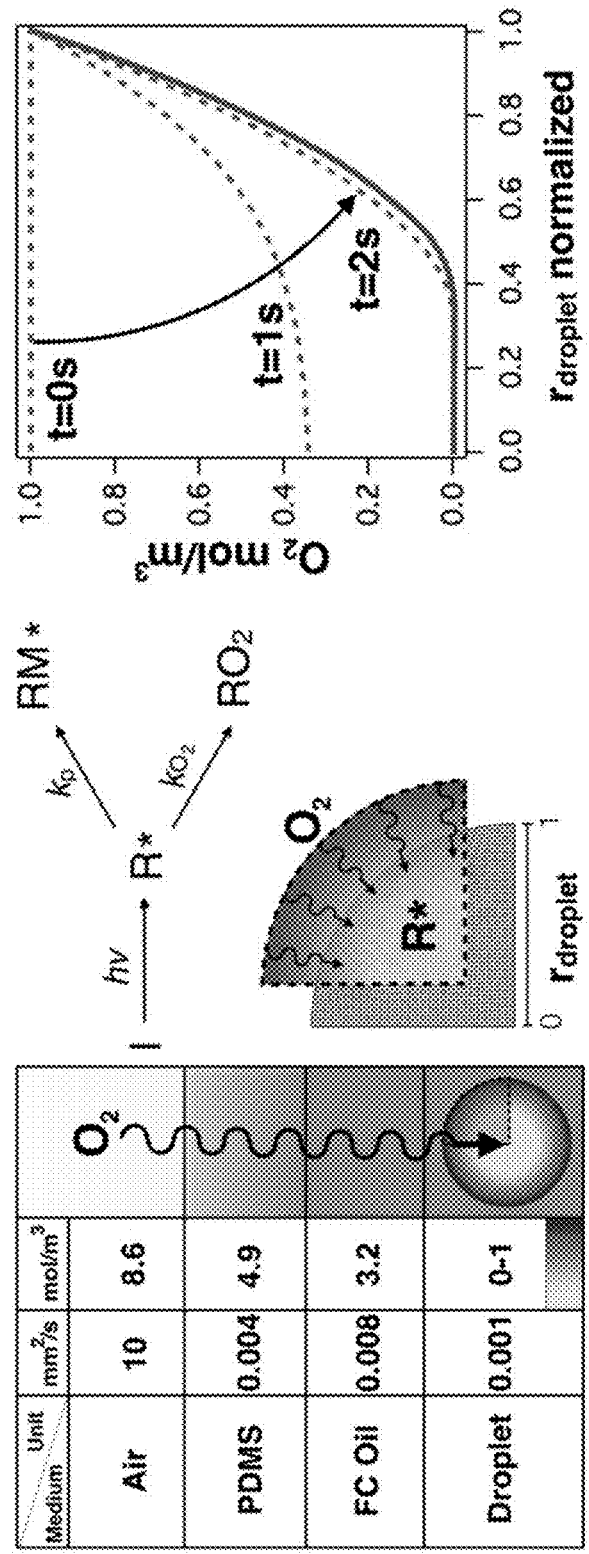
FIG. 2. Provides an analysis of the effects of oxygen on PEGDA photopolymerization in microfluidic multiphase droplets under ambient atmosphere.

FIG. 2. Provides an analysis of the effects of oxygen on PEGDA photopolymerization in microfluidic multiphase droplets under ambient atmosphere. Far left: A summary of nominal oxygen diffusivity and equilibrium concentration for each region of interest in the multiphase microfluidic droplet-generating device. Values are summarized from various literature sources (REF 1.10, 1.43-1.47). A schematic illustration of oxygen transport from air into PDMS, through fluorocarbon oil, and into the microdroplet (not to scale) is also shown. Given the absence of diffusion barriers, the concentration of oxygen in an un-purged device is not constrained until it reaches the microdroplet. At center, a reaction schematic illustrates the polymerization reaction and rival initiator scavenging mechanism. Oxygen concentration in the droplet was evaluated with a COMSOL 1-D radial model of oxygen diffusion and reaction. A meshed quadrant with a 1-D concentration overlay surface provides a representative oxygen concentration profile. On the far right, a typical time dependent oxygen concentration profile in a microparticle of radius, $r=30$ µm during course of polymerization. The model predicts that while photoinitiator radicals quickly deplete oxygen initially present within the droplet, equilibrium is rapidly established by continuously diffusing oxygen from the oil phase. With UV intensity of 10 mW/cm$^2$, a semi-steady state oxygen profile is achieved in the droplet after only ~2 seconds.

Figure 3:
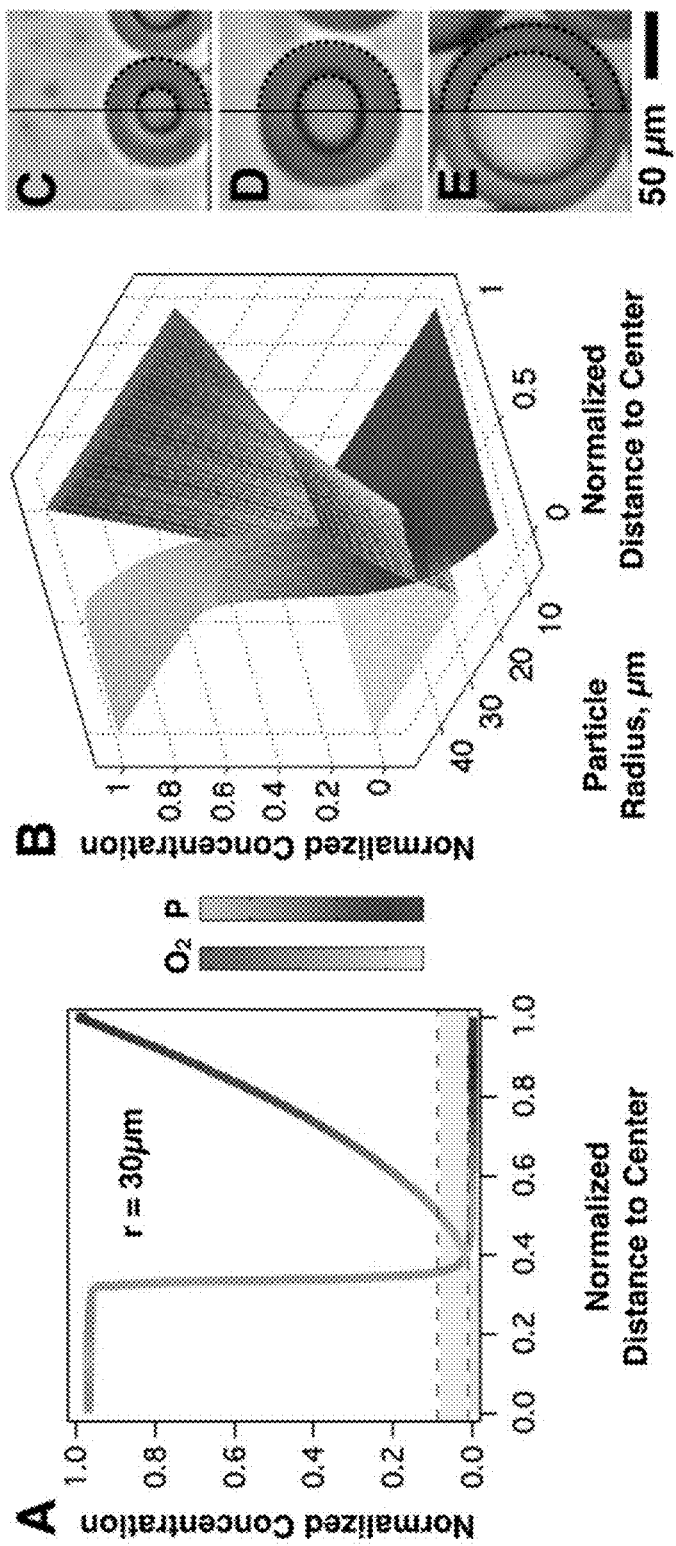
FIG. 3. illustrates Oxygen diffusivity sets the lower threshold for droplet polymerization in multiphase microfluidic devices.

FIG. 3. Illustrates Oxygen diffusivity sets the lower threshold for droplet polymerization in multiphase microfluidic devices. A) Polymerized PEGDA fraction, shown in green, strongly depends on diffused oxygen concentration (red) in a microdroplet (r=30 µm). As polymerization is impeded by dissolved oxygen, only a fraction of the droplet's radial volume is polymerized (~0.38) and the rest (~0.38-1) remains liquid oligomer (blue). The gray region represents minimum polymerization fraction values needed to observe gelation of the monomer solution (REF 1.48, 1.53). B) A 3-D surface plot, compiled from a set of analogous curves for particle radius in range of r=10-50 µm, illustrates a threshold for droplet polymerization at r<20 µm. To the right, we show microscope bright field images of partially polymerized 40% PEGDA-700 particles (A: r~30 µm, B: r~50 µm, C: r~60 µm). Images were partially overlaid with color to help visualize distinct polymerized and unpolymerized fractions.

Figure 4:
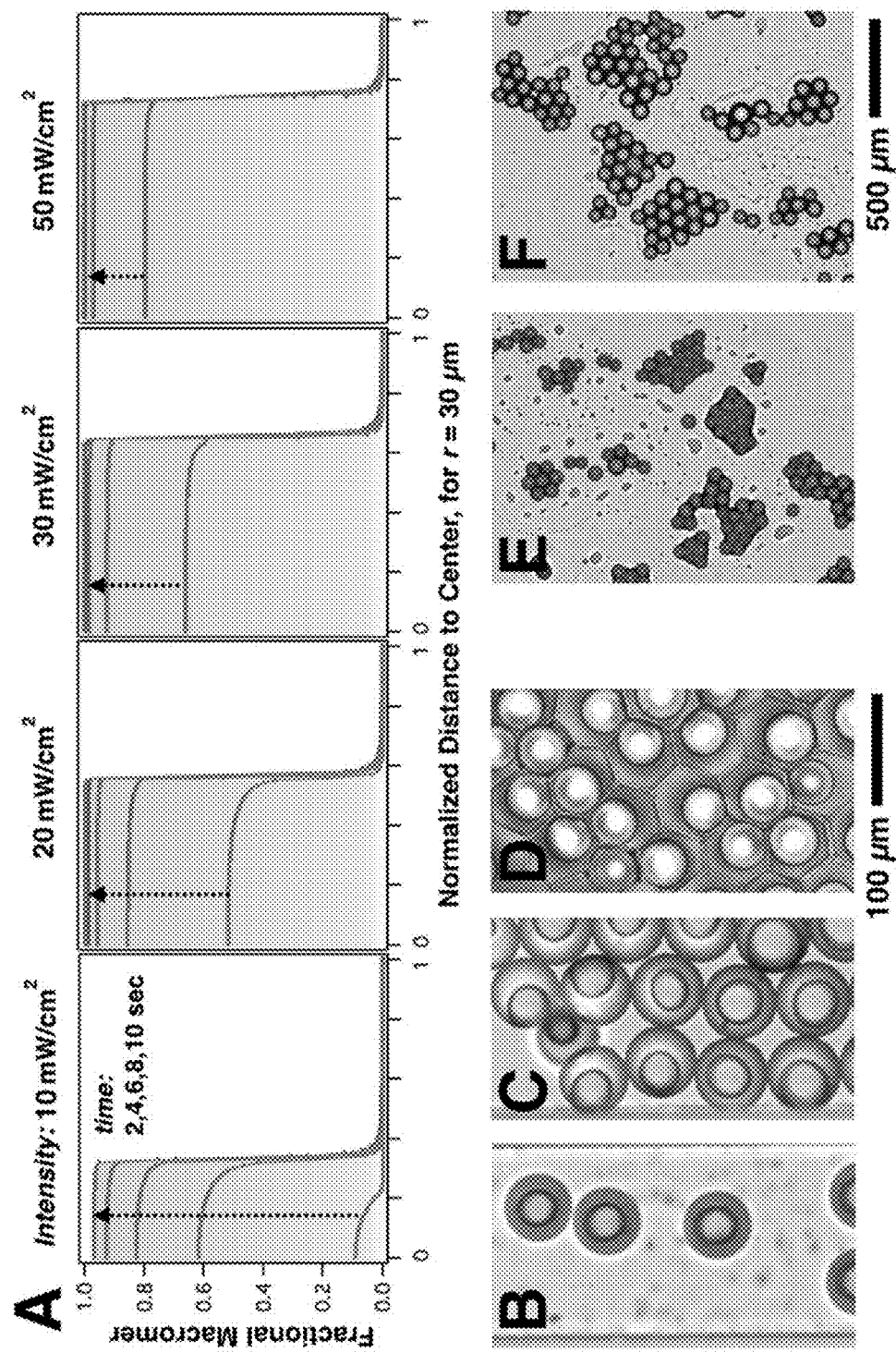
FIG. 4. provides curves illustrating the fraction of polymerized PEGDA as function of exposure time and intensity are shown for a model droplet (r=30 μm).

FIG. 4. Provides curves illustrating the fraction of polymerized PEGDA as function of exposure time and intensity are shown for a model droplet (r=30 µm). With increasing intensity, all polymerized fraction curves shift to right and thus the partially polymerized droplet radius increases. Additionally, with increased UV intensity these concentration-time curves shift up as monomer double bond conversion is expedited, relative to the rate of oxygen diffusion. B: The polymerized core of partially polymerized emulsion droplets is evident under flow and C: upon flow cessation, in which polymerized droplet cores settle at droplet interfaces. D: Passive removal of the oil from partially polymerized emulsions drives self-assembly of hexagonal matrices stabilized by surfactant present at the interface. E and F: Un-polymerized fraction variations have been also experimentally observed by changing following variables: initiator concentration, initial macromer concentration, and UV intensity.

Figure 5:
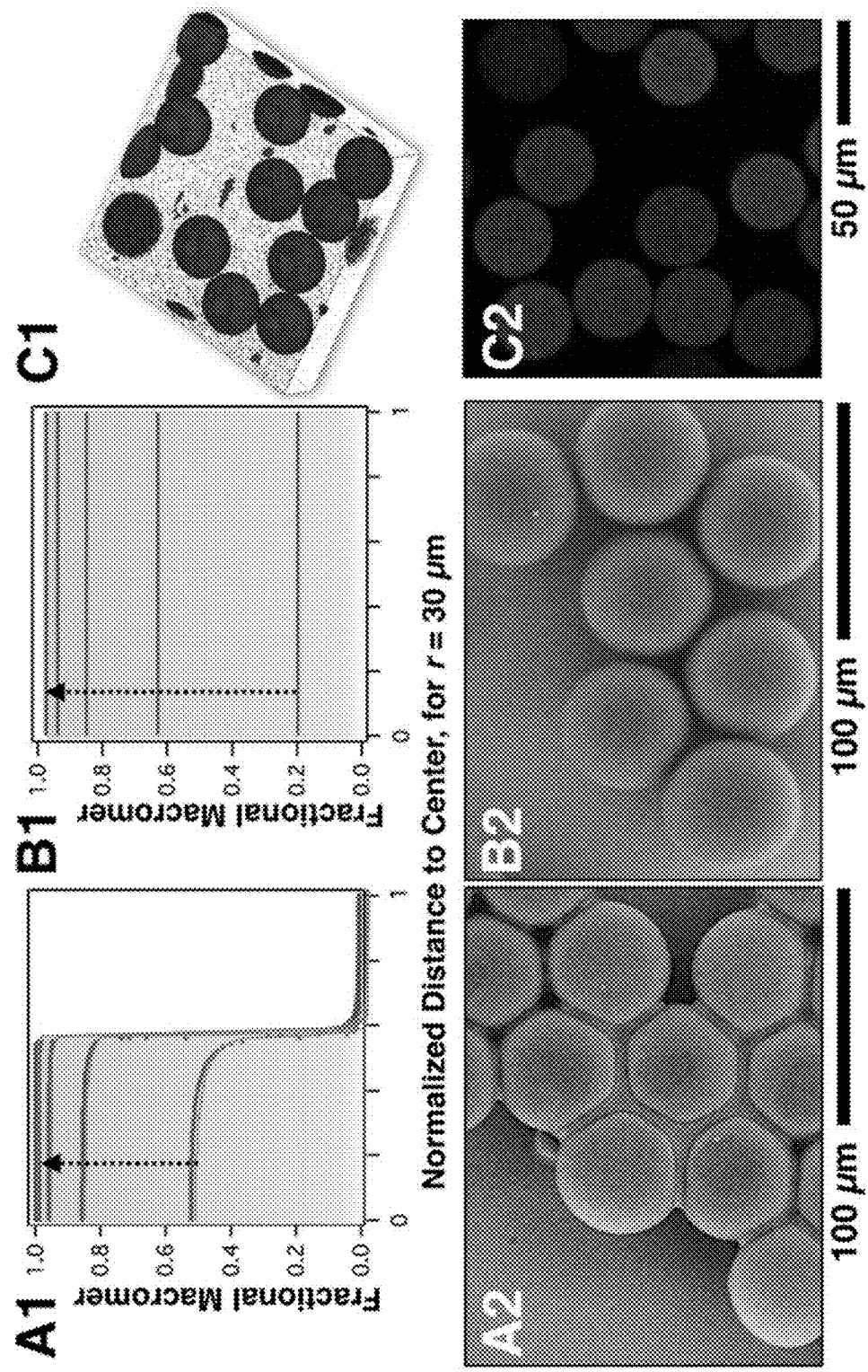
FIG. 5. provides graphs and SEM images illustrating partially and fully polymerized particles.

FIG. 5. Graphs and SEM images displayed in sections A and B, respectively contrast partially and fully polymerized particles. Upon particle extraction from oil, thin unpolymerized liquid fraction is difficult to remove and it typically surrounds hydrogel spheres, holding particles together (A2). Fully polymerized particles do not exhibit an unpolymerized liquid layer (B2). Fully polymerized hydrogel particles marked with rhodamine acrylate have been also produced and imaged with confocal microscopy to verify polymerization uniformity within particles. Image C1 and C2 show a three-dimensional stack image and cross sectional image of the polymerized particles, respectively. This particular imaging technique confirmed the localization of rhodamine within the particle by copolymerization, and therefore particle polymerization.

Figure 6:
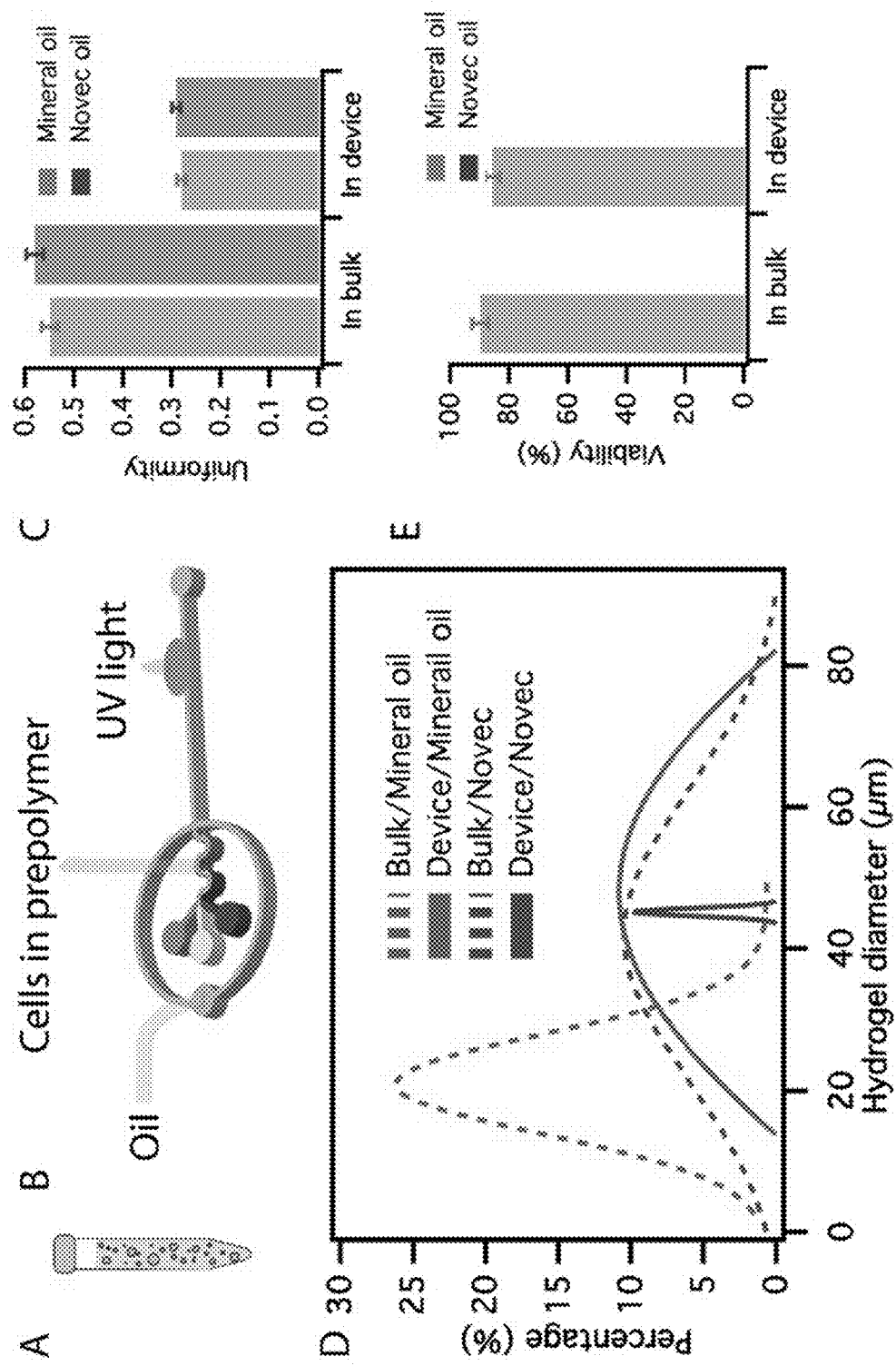
FIG. 6. sets forth an illustration showing the encapsulation of cells by various methods.

FIG. 6. Sets forth an illustration showing the encapsulation of cells by various methods. (A) Cell encapsulation in bulk. (B) Cell encapsulation in microfluidic device. (C) Size distribution of hydrogel micro particles using different polymerization methods. (D) Uniformity of hydrogel micro particles using different polymerization methods. (E) Post-encapsulation viability of cells encapsulated using different methods, in bulk and in device, using Mineral oil and Novec 7500, respectively.

Figure 7:
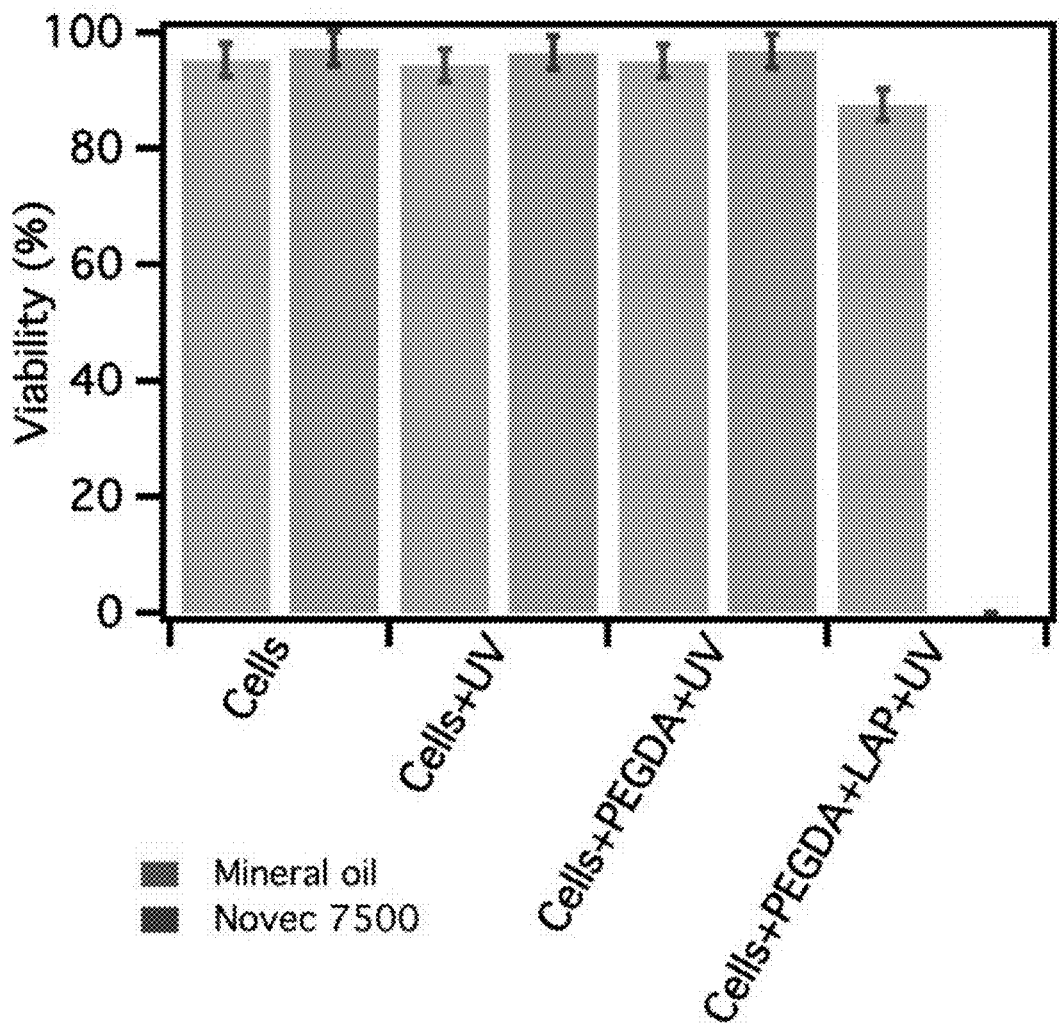
FIG. 7. provides Cell viability studies as a function of different parameters involved in cell encapsulation in the microfluidic device using Mineral oil and Novec 7500, respectively.

FIG. 7. Provides Cell viability studies as a function of different parameters involved in cell encapsulation in the microfluidic device using Mineral oil and Novec 7500, respectively.

Figure 8:
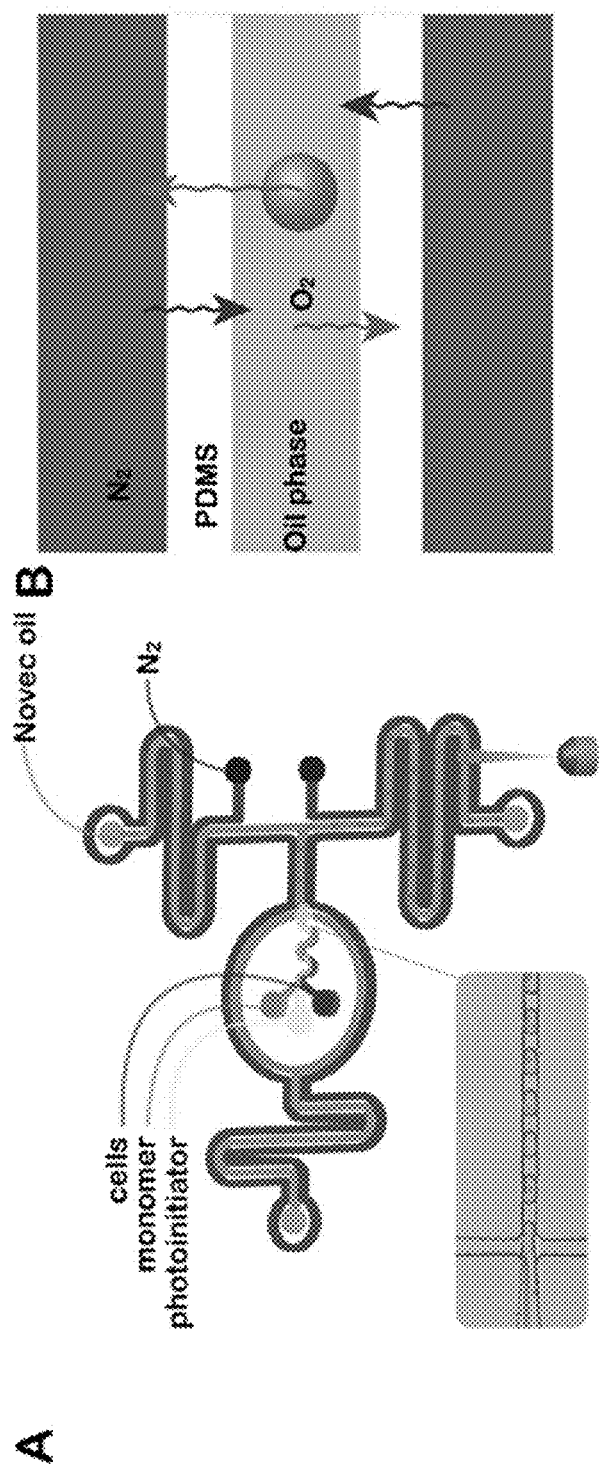
FIG. 8. illustrates Cell encapsulation using the nitrogen jacked two-layer microfluidic device.

FIG. 8. Illustrates Cell encapsulation using the nitrogen jacked two-layer microfluidic device. (A) Schematic illustration of the two-layer nitrogen jacked microfluidic device. The initiator, cell suspension, and monomer mixture were fully mixed in device and then merged with a fluorocarbon oil to generate cell-laden droplets at the nozzle of the first layer of the device. Fluid Flow channels are bounded on each side by in-plane nitrogen channels. Formed emulsion droplets were photopolymerized to hydrogel by exposure to UV light in the second layer of the device. (B) Schematic of oxygen purging from the system. Increased nitrogen pressure decreases oxygen solubility, which results in oxygen diffusion from the droplet and oil into the PDMS matrix.

Figure 9:
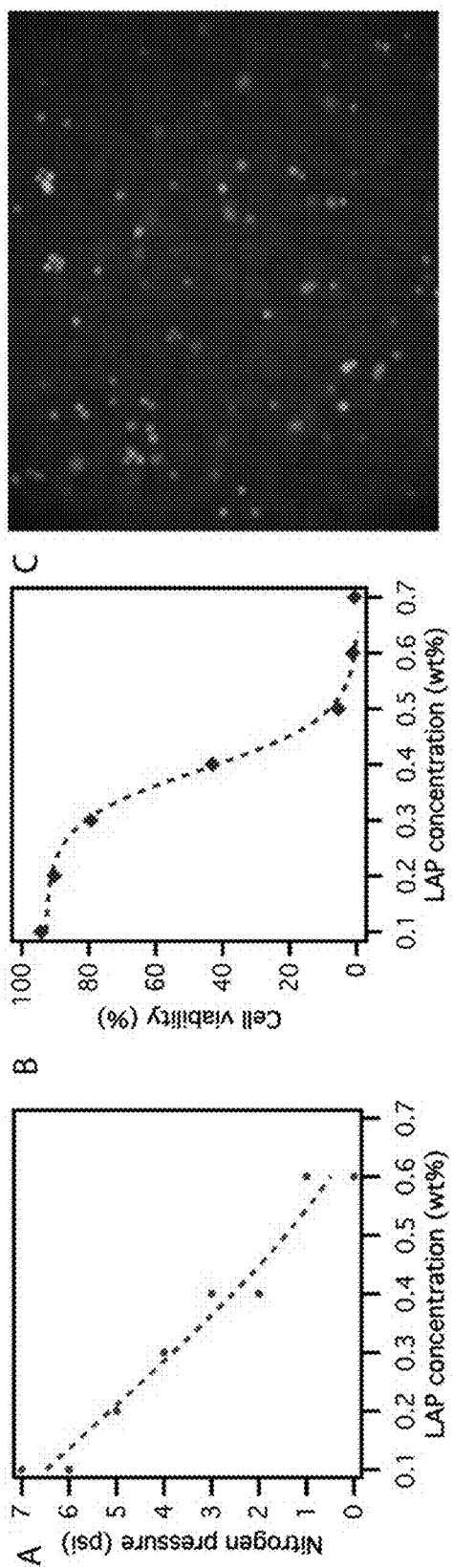
FIG. 9. provides post-encapsulation viability of cells under different LAP and nitrogen concentrations.

FIG. 9. Provides (A) Minimum LAP concentration needed for the polymerization under different nitrogen pressure (B) Post-encapsulation viability of cells with different LAP concentration at a constant nitrogen pressure (psi=7) in the nitrogen pre-purged microfluidic device. (C) Post-encapsulation viability of cells was assayed by live-dead stain, where the live cells were green, and the dead cells were red.

Figure 10:
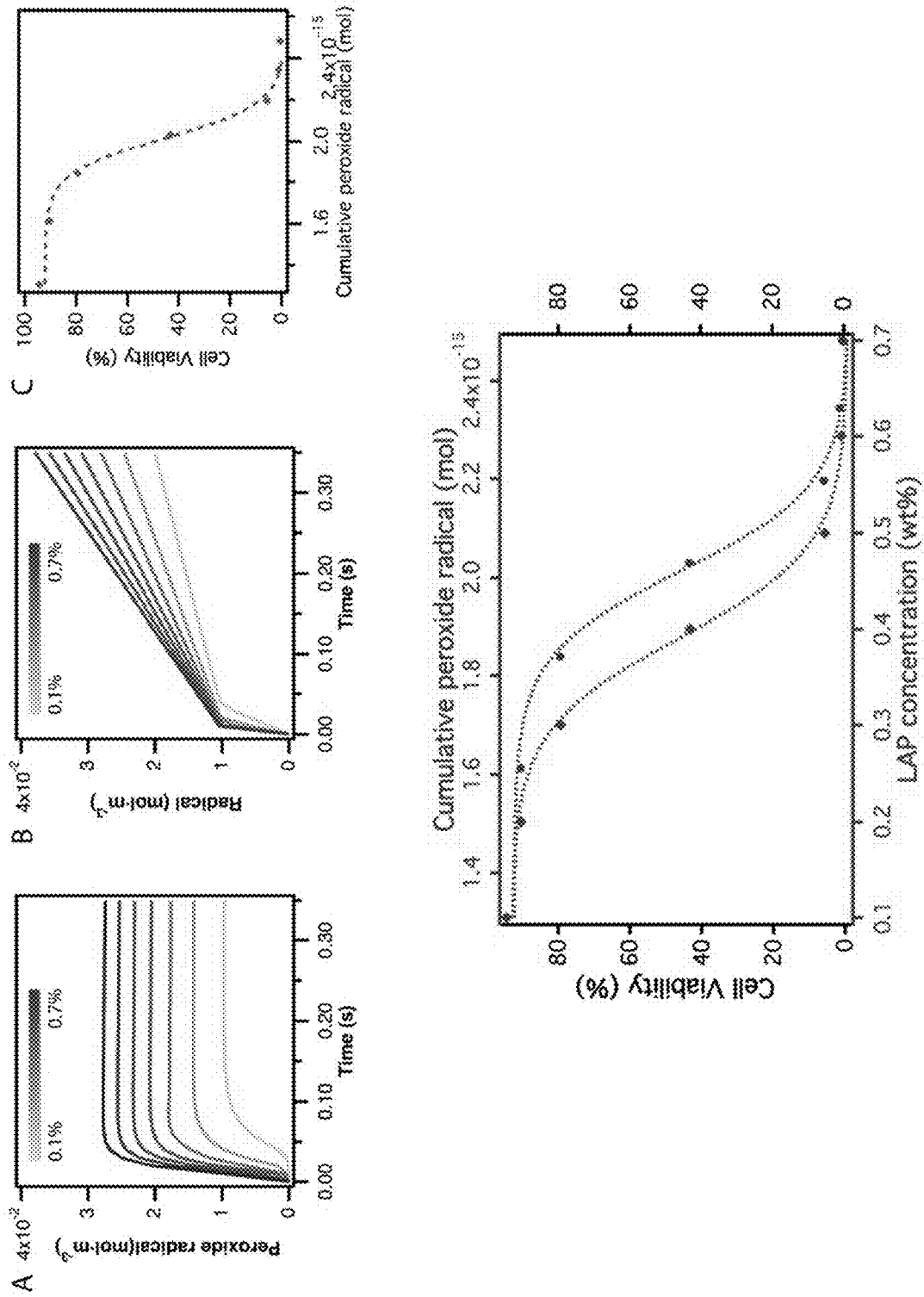
FIG. 10. provides cumulative concentrations of peroxide radical over time.

FIG. 10. Provides (A) Cumulative concentration of peroxide radical and radical in dependence of time in the droplets or hydrogel micro particles. (B) Cumulative concentration of peroxide radicals in dependence of time in the droplets or hydrogel micro particles. (C) Cumulative amount of peroxide radical in time equal to 0.35 s and the corresponding post-encapsulation viability of cells in hydrogel micro particles.

Figure 11:
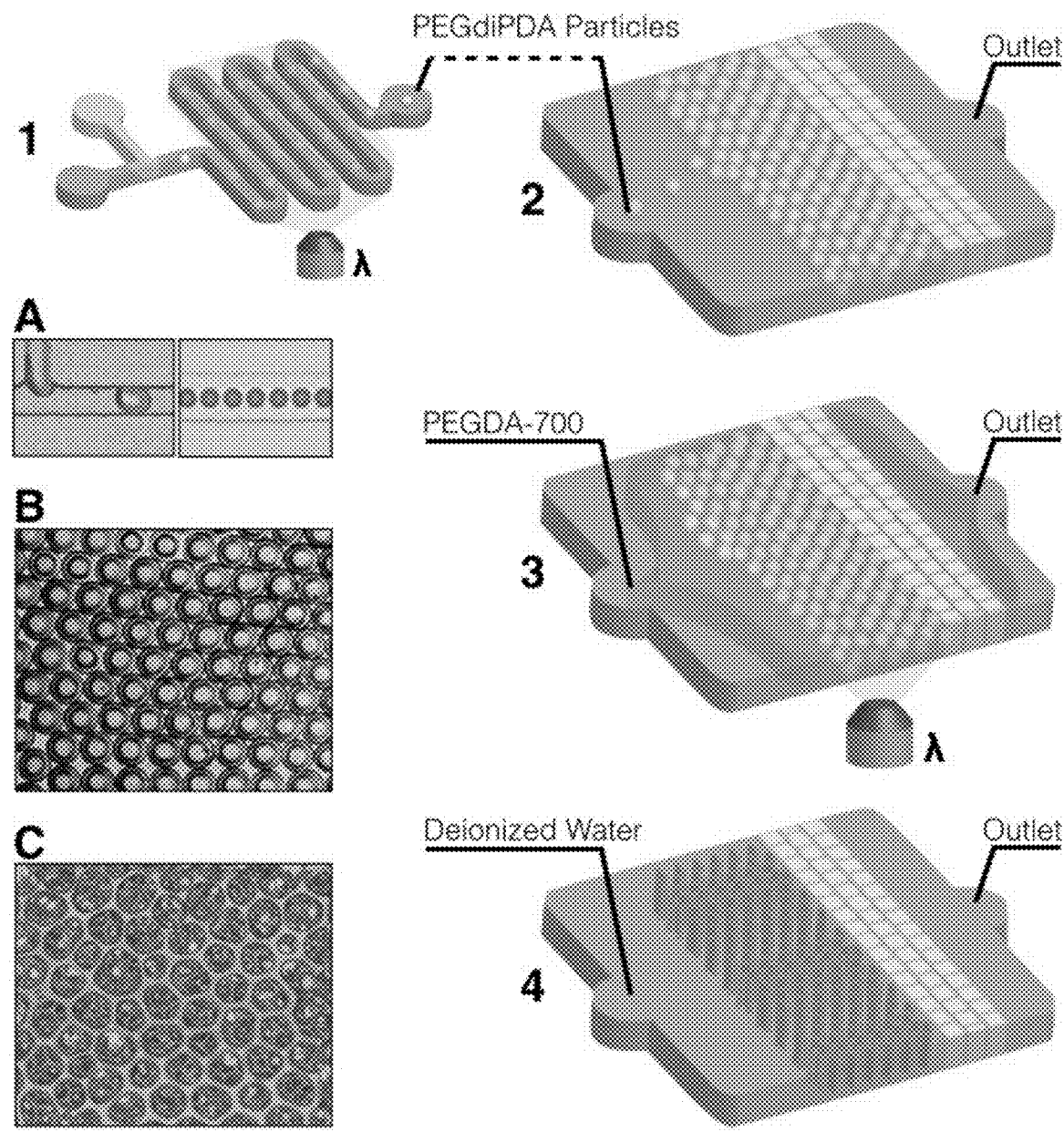
FIG. 11. provides a schematic illustrating the process of porous scaffold fabrication within a microfluidic channel.

FIG. 11. is a Schematic illustrating the process of porous scaffold fabrication within a microfluidic channel. Monodisperse PEGdiPDA microparticles are mass-produced in a T-junction microfluidic device and used as a porogen for ICC preparation (1, A) PEGdiPDA particles are packed via laminar flow in a slit-filter microfluidic device. (2) The assembled particle matrix is infused with PEG-DA macromer solution and the particle structure is locked in via secondary UV (405+nm) photo-polymerization. (3, B) Once the continuous phase is polymerized, photo-degradation of template particles is achieved with 365 nm UV light. A schematic of a PEG-DA hydrogel ICC fabricated within a microfluidic device is shown in image 4 and image C shows a confocal image of the resultant macroporous ICC.

Figure 12:
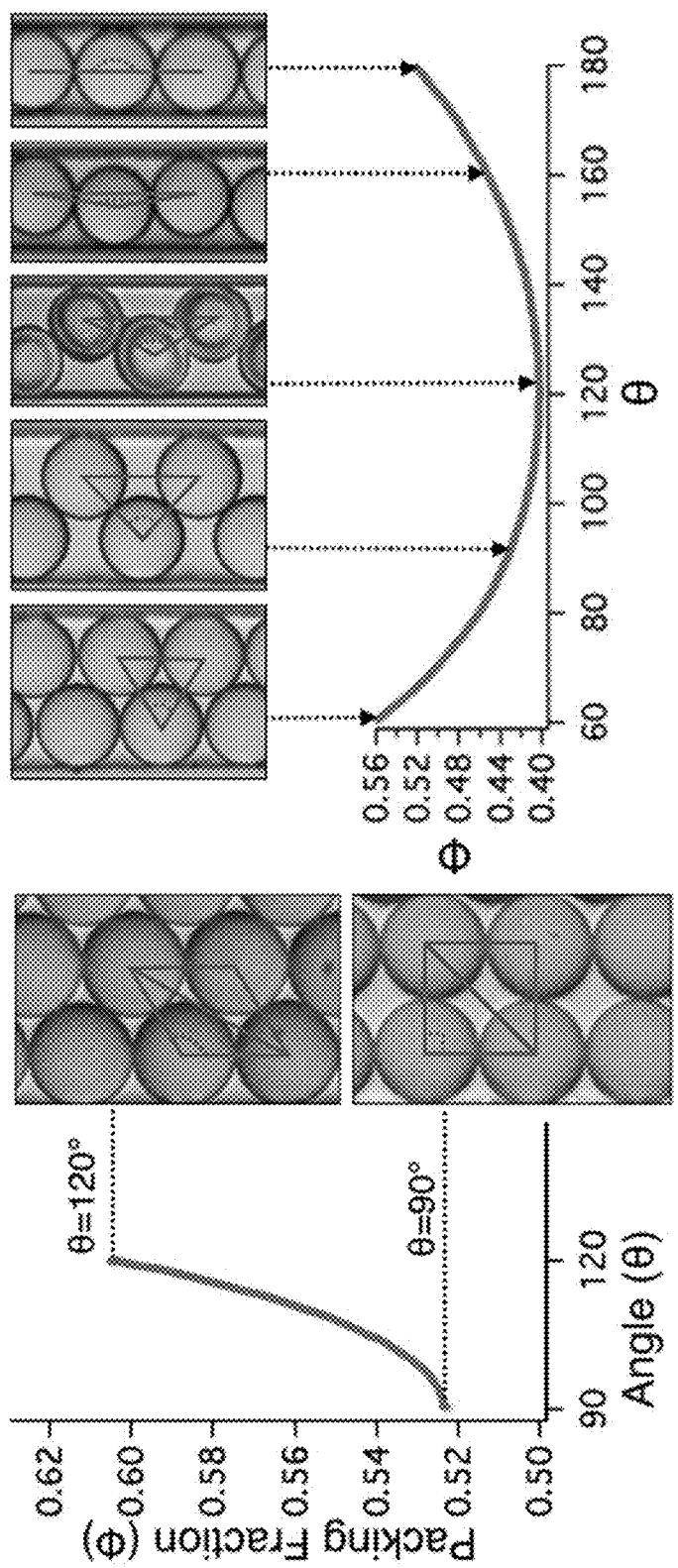
FIG. 12. illustrates flow assisted planar (2-D) hydrogel particle assembly in microfluidic channels producing closely packed structures with order dictated by channel dimensions.

FIG. 12. Illustrates Flow assisted planar (2-D) hydrogel particle assembly in microfluidic channels produces closely packed structures with order dictated by channel dimensions. The plot at far left illustrates a general trend of particle organization and particle packing fraction as function of adjacent angle between neighboring particles. At right, it is clear that 2-D order in narrow slit channels is dominated by the boundaries, which reduce packing density as low as ~0.4.

Figure 13:
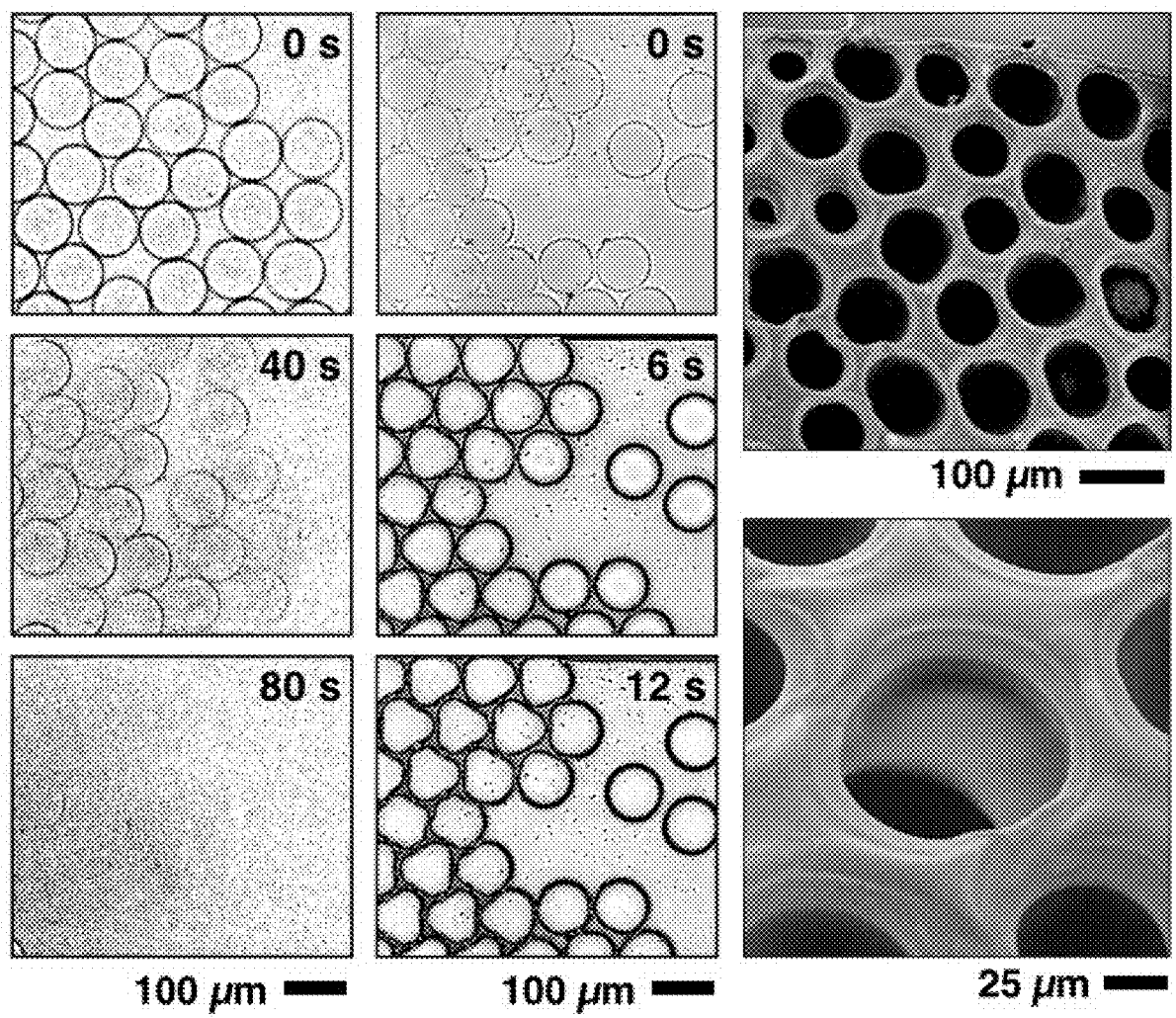
FIG. 13. illustrates simultaneous, rapid, and non-invasive inverse opal formation.

FIG. 13. illustrates simultaneous, rapid, and non-invasive inverse opal formation. PEGdiPDA hydrogel particles exposed to 365 nm light degraded within ~80 seconds. Panels A-F track the time course of the particle degradation, while (corresponding bright-field microscopy snapshot images in the left column), the non-degradable macromer (40% PEGDA-700) is simultaneously crosslinked. The polymerization reaction occurs over only ~12 seconds (bright-field microscopy snapshot images in the middle column), and producing 2-D porous scaffold. Scanning electron microscope images of fabricated porous scaffolds from photodegradable particles are shown in the right column.

Figure 14:
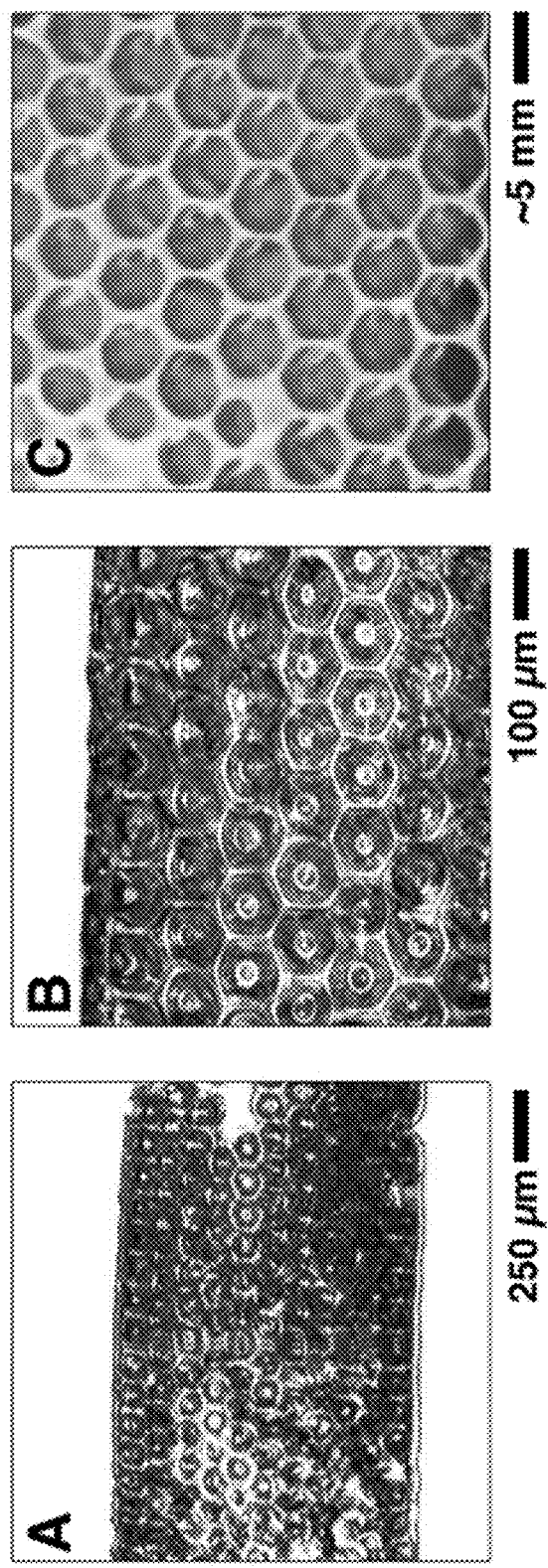
FIG. 14. provides surface scanning laser confocal microscope images of a porous hydrogel scaffold assembled and produced in a microfluidic device from photodegradable hydrogel particles (A, B) and bee honeycombs (C).

FIG. 14. A, B show surface scanning laser confocal microscopic images of a porous hydrogel scaffold assembled and produced in a microfluidic device from photodegradable hydrogel particles. Flow induced packing has kept hydrogel particles in close contact with each other, however upon secondary phase polymerization we also observe transformation of spherical pores into hexagonal (B). Our obtained hexagonal hydrogel pore structure (B) resembles bee honeycombs (C). Speculatively, this phenomenon occurs for similar reasons as in bee honeycombs, mainly due to tension forces pulling at the three wall junction as the continuous phase prep polymer undergoes polymerization (REF 3.11).

Figure 15:
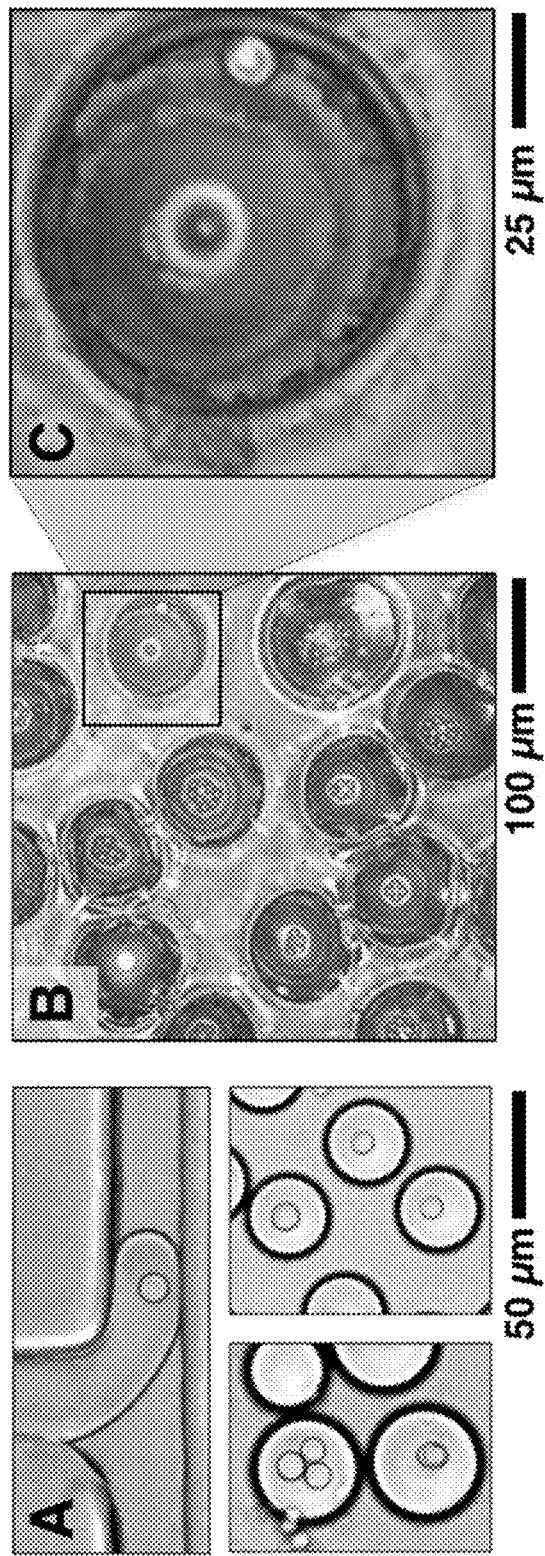
FIG. 15. illustrates gentle erosion of the particle network allowing secondary particles to be seeded within the porous inverse opal architecture.

FIG. 15. illustrates gentle erosion of the particle network allows secondary particles to be seeded within the porous inverse opal architecture. As a demonstration of this concept, in image A, =5 μm polystyrene beads are encapsulated within a droplet, which is subsequently polymerized to form a bead-laden. hydrogel particle (inset images). Image B and C show a porous hydrogel inverse opal seeded with polystyrene beads. An isolated microvoid is highlighted of evidence of pre-seeding.

Example 1: Monodisperse Polyethylene Glycol Diacrylate Hydrogel Microsphere Formation by Oxygen-Controlled Photo-Polymerization in a Microfluidic Device Introduction Acrylate-based polymers are regarded for their transparency, color variation, robust mechanical properties, and elasticity (REF 1.1). Acrylates are easily photopolymerized on industrial scales and widely used in chemical applications as adhesives, sealant composites, and protective coatings (REF 1.1, 1.2). Compared to other synthetic monomers, acrylates are often preferred due to their biocompatibility and chemical versatility, allowing modification with a range of monofunctional or multifunctional moieties (REF 1.3-1.4). Oligomeric acrylates can be used to produce highly crosslinked networks by photopolymerization methods (REF 1.5). Based on these characteristics, a class of photopolymerizable polyethylene glycol (PEG)-based hydrogels has been developed around acrylate polymerization chemistries (REF 1.6-1.8).

Photopolymerization is a convenient and cytocompatible alternative to solvent-based or thermal curing, and can be carried out both in-vitro and in-vivo (REF 1.9). The photoinitiated free radical polymerization of acrylates is typically performed in the presence of a photoactive initiator that generates free radicals upon exposure to ultraviolet light. Acrylate free radical polymerization is strongly inhibited, however, by the scavenging of free radicals by oxygen (REF 1.10-1.12). Dissolved oxygen is typically present throughout bulk PEGDA solutions, but is quickly consumed, allowing polymerization to proceed. Prolonged oxygen scavenging can occur if the solution is in contact with an oxygen source, such as an air interface or a surface with a sufficiently high oxygen solubility and permeation rate. On a microscale, the inhibition of photopolymerization reactions is exacerbated due to increased surface-to-volume ratios.

PEGDA is attractive to use as a cell encapsulant and tissue scaffold because of its tissue-like physical properties, which can be tailored to closely mimic extracellular matrices, cytocompatibility and synthetic versatility. Over a certain polymer composition range, highly water-swollen PEGDA hydrogel networks have been proven to be cytocompatible encapsulants for many cell types including fibroblasts (REF 1.13), chondrocytes (REF 1.14), vascular smooth muscle cells (SMCs) (REF 1.15), endothelial cells (ECs) (REF 1.16), osteoblasts (REF 1.17) neural cells (REF 1.18) and stem cells (REF 1.19). Synthetic customization of PEGDA macromolecular architecture and chemistry provides a large diversity of properties, making it an attractive alternative to natural hydrogels. PEGDA hydrogel networks can be decorated with cell-adhesive peptide groups that allow the formation of bioactive hydrogels that promote cell adhesion, spreading and tissue elaboration (REF 1.20) Modifications to the PEG crosslinker can provide an ability to spatially and temporally remodel the hydrogel by hydrolytic (REF 1.6), proteolytic (REF 1.7) or optical degradation (REF 1.21). Directed network remodeling has become widely used as a strategy for temporally regulating hydrogel properties.

Microscale PEGDA hydrogel particles, or "microgels" are of emerging importance to the sensing (REF 1.22), drug and tissue engineering (REF 1.23) communities due to intraparticle diffusion, facile antibody or oligonucleotide conjugation, and potential for in vivo applications. PEG microgels have been successfully fabricated via stop-flow lithography, a single-phase microfluidic step-wise photopolymerization technique. Stop-flow lithography in poly(dimethylsiloxane) (PDMS) microfluidic devices exploits the elastomer's high oxygen permeability and oxygen transport rates to maintain thin unpolymerized zones near channel surfaces due to inhibition by oxygen (REF 1.23-1.24). These unpolymerized films prevent the adhesion of polymerized structures to channel surfaces, allowing them to be freely harvested as particles. Other applications include the fabrication of complex shape microparticles (REF 1.23, 1.25), cell encapsulation (REF 1.23), and complex particle barcoding (REF 1.26, 1.27).

Stop-flow lithography has allowed particles to be produced with arbitrary and precise two dimensional shapes defined by the photo mask, and incomplete polymerization produces particles with lateral gradients of crosslinking density arising from oxygen diffusion from the particle edges (REF 1.28). Despite the broad versatility of this technique, the required presence of ambient oxygen constrains particle fabrication rates, and significantly limits the ability to simultaneously dictate particle size and polymer composition (REF 1.23).

PEG microspheres may be fabricated at much higher rates than stop-flow lithography by emulsifying two-phase oil-water suspensions. Microparticles are commonly prepared by bulk aqueous phase emulsification via sonication, vortexing, or homogenization, or by microfluidic drop-wise emulsification. Following emulsification, stabilized particles suspended within the immiscible oil are photopolymerized by irradiation (REF 1.29, 1.30). Hydrogel particles made by either bulk or microfluidic emulsification have potential applications in a wide range of promising medical research applications including targeted drug-delivery (REF 1.31), cell encapsulation (REF 1.7), assembly of complex scaffold frameworks (REF 1.32), and biomaterial encapsulation (REF 1.33).

Bulk emulsification is typically performed with relatively large volumes of solution, and produces larger microparticles (>100 µm) over a wide size distribution. The photopolymerization process in bulk emulsions is similar to that in bulk homogeneous PEG macromere solutions, in which oxygen inhibition is quickly overcome as oxygen in the surrounding oil phase is rapidly depleted.

Microfluidic emulsification, on the other hand, is a precise and repeatable process that can produce uniform size particles with an exceptional control of their respective composition. To preserve size homogeneity, it is desirable to photopolymerize droplets upon the device immediately after they are formed. This is possible and has been demonstrated with large droplets (REF 1.34), or droplets of high PEG or initiator concentration (REF 1.36). Conversely, continuous photopolymerization has not been demonstrated in smaller droplets with lower, cytocompatible PEG-initiator compositions. In both of these cases, the oxygen inhibition of free radical polymerization, amplified by fluorocarbon oils and PDMS devices, prohibits photopolymerization. As such, despite the tremendous potential suggested for the microfluidic fabrication of monodisperse, small (<40 µm) cytocompatible PEG hydrogel microspheres, their continuous fabrication has not yet been reliably achieved.

In order to enable acrylate polymerization within microscale emulsion droplets, various techniques to eliminate oxygen during free radical polymerization have been proposed, such as vacuum-based degassing (REF 1.37), nitrogen purging (REF 1.38), PDMS diffusion barriers (REF 1.39) and photopolymerization under sealed, inert gas environments (REF 1.40). Most of these oxygen-shielding techniques are challenging or costly to implement. Isolating entire microfluidic processing apparatus, including pumps, syringes, tubing, devices and microscope) from oxygen is impractical. For an oxygen-degassed PDMS device, the experimental run time is temporary limited to minutes before oxygen is replenished throughout the device. To address oxygen-inhibition during polymerization and enable stable, long-term microfluidic microparticle synthesis, we disclose a unique nitrogen micro-jacketed PDMS microfluidic device design (FIG. 1). Performance of the $N_2$ micro-jacketed device is characterized experimentally and complemented with a coupled $O_2$ reaction-diffusion finite element numerical model. This approach overcomes the limitations of other droplet photopolymerization devices, providing the ability to independently specify polymerized particle size and composition, while making available a range of cytocompatible compositions that were previously inaccessible.

Materials and Methods

FIG. 1A illustrates the microfluidic device design, which includes PDMS microchannels for fluid flow, flanked with channels to carry nitrogen. This configuration sufficiently elevated the local nitrogen concentration, depleted oxygen in the PMDS and prevented oxygen from diffusing through and interacting with fluids. We have exploited the gas permeability and membrane-like characteristics of PDMS to saturate the microchannel region with nitrogen (FIG. 1) during PEGDA microparticle polymerization.

Device Construction

PDMS microfluidic devices were fabricated from single layer photolithographically patterned masters using standard PDMS photolithography techniques (REF 1.41, 1.42), and bonded to 2"×3" glass slides. Shown schematically and in optical micrograph images (FIGS. 1B and 1C, respectively), PDMS devices consisted of a 100 µm thick droplet generation and transport channel sheathed by a 100 µm thick nitrogen jacketing channel. The PDMS wall thickness between parallel fluid and nitrogen channels was 100 µm, sufficient to hold the PDMS-glass bond intact up to 5 psi at the device inlet (pressures of +10 psi required increase of the wall thickness between the channel walls of up to 250 µm).

Fluid Control

Fluidic inlet and outlet holes of the nitrogen-jacketed PDMS particle photopolymerization device were connected to fluid sources and collection reservoirs, respectively, via microbore Tygon® tubing (0.01"ID×0.03"OD, ND-100-80, United States Plastic Corp.). Nitrogen was introduced into the device through a microbore Teflon tubing at a positive permeation pressure of ~5 psig. The nitrogen gas flow was controlled with a pressure regulator that allowed a given pressure to be specified at the device inlet. An open gas outlet was not used, and it was found the $N_2$ purging was more effective if the outlet remained closed and the channel pressurized (as seen in FIG. 1 D, gas channels are slightly wider due to inflation under nitrogen pressure). Operating fluids (oil and hydrogel macromer solution) were loaded into disposable plastic syringes (1-10 ml, Becton Dickinson) and the flow of each component was independently controlled with a syringe pump (Nemesys syringe pump, Cetoni, Germany).

Device Operation

A T-junction (REF 1.41) microfluidic channel configuration was used to emulsify the macromer solution into a fluorocarbon oil, Novec™ 7500, 3 M (+2% wt. Krytox FSL 157 as a surfactant, DuPont). Fluorocarbon oil was chosen because of low viscosity and vapor pressure; ease of particle phase extraction with minimal remaining oil residue, and the high two-phase stability relative to other commonly used oils. Produced droplets traveled downstream in a long serpentine channel with a residence time of seconds. Droplets contained monomer solution at concentrations of 10-40% PEGDA-700 (v/v) (CAS Number 26570-48-9, Sigma Aldrich), 1-6% Irgacure 1173 initiator (v/v) (CAS Number 7473-98-5, Sigma Aldrich) in water. Droplet composition was varied to alter reaction kinetics to validate modeling. By varying flow rates of the continuous and dispersed fluids, the produced droplet size was also controlled at the T-junction over a range of r=5-50 µm. In the serpentine channel, droplets were exposed to UV light (5-15 mW/cm$^2$). Illumination was performed with a fluorescent illumination system (Prior Lumen-200), and an inverted microscope (IX 71, Olympus) with a DAPI filter cube and 2-4× objective. UV light intensity was measured with a handheld cure site radiometer (Power Puck II, Uvicure). Produced microparticles were collected in a microcentrifuge tube (Eppendorf) or directly upon a cover slip for imaging with bright field microscopy. Partially polymerized particle recovery from the oil phase to an aqueous medium was achieved by fluorocarbon oil evaporation or filter-based drainage followed by a multi-stage sonication wash for ~10 minutes in deionized water (the washing fluid was consecutively drained and changed 3-4 times). Sonication washing effectively removed any unpolymerized liquid fraction and surfactant from the polymerized droplet core. Conversely, fully polymerized particles retained their surfactant, creating hydrophobic surfaces that prevented dispersion into an aqueous phase. Fully polymerized particle re-suspension in water was therefore achieved by the introduction of a secondary aqueous-based surfactant (Pluronic®) prior to filtration and washing.

Numerical Model of Polymerization and Inhibition

A one-dimensional model of free radical hydrogel photopolymerization in the presence of oxygen was created to describe spatial and temporal states of PEG-DA within water-in-oil (WO) emulsion droplets. This model serves the need to quantify the competition between polymerization and oxygen inhibition within oxygen-supplying PDMS microfluidic devices. The model was built in the COMSOL multiphysics software package using the assumptions and parameters described below. To visualize the model output we present two dimensional concentration profiles, built upon a quadrant circle, representing a quarter of a droplet cross section from center to wall (FIG. 2). Finite element analysis was performed over the area of the quarter circle, meshed into 10,000 quadrilateral elements. Time dependent studies were performed using the Transport of Diluted Species COMSOL physics module. Total simulation times of 10 seconds with individual time steps of 0.1-1 seconds were used throughout the study, but were tuned to achieve solution convergence.

Results and Discussion

Theory and Simulation

PEGDA photopolymerization begins with the photoactivation of an initiator, in which initiator molecules (I) absorb UV light (hv), decompose, and transform into radical species (R). Subsequently, radical species are free to react with monomer (M) to initiate and propagate chain formation, or self-terminate via oxygen reaction (reaction schematic, FIG. 2). Due to high oxygen solubility and diffusivity in the fluorocarbon oil and PDMS respectively, the region surrounding droplets may be effectively considered to be an inexhaustible oxygen source. As a result, the oxygen concentration at the droplet boundary is assumed to be perpetually saturated. In an aqueous microdroplet, the nominal equilibrium solubility of oxygen ($c_{O2}$) is ~1 mol/m$^3$ and the rate of oxygen scavenging is initially five orders of magnitude larger than the rate of polymer propagation, thus polymerization will not proceed until oxygen is depleted. Radicals are rapidly consumed by oxygen because the rate of the inhibitory reaction is much faster than that of polymerization ($k_{O2}[O_2] \gg k_p[M]$). Polymerization only resumes once the respective rates of oxygen inhibition and polymerization are equivalent, or $k_{O2}[O_2] \sim k_p[M]$ (REF 1.10).

Table A summarizes a reaction step sequence implemented in our model and that is commonly used for describing free radical polymerization (REF 1.10, 1.48, 1.49). In step 1, a radical specie is formed, step 2 initiates the polymer chain formation with the radical specie, and step 3 is a propagation step during which polymerization takes place. Steps 4 and 5 are both considered termination steps where radicals are either terminated by the oligomer chain reaction or oxygen inhibition.

TABLE A

Reaction Mechanism for Acrylate Monomer Polymerization

| Step # | Reaction | Description |
|---|---|---|
| 1 | $I \xrightarrow{hv} R*$ | Initiator photolysis |
| 2 | $R* + M \rightarrow RM*$ | Chain initiation |
| 3 | $RM*_n + M \xrightarrow{k_p} RM*_{n+1}$ | Chain propagation |
| 4 | $RM*_n + RM*_m \xrightarrow{k_t} RM_nM_m$ | Chain termination |
| 5 | $RM*_n + O_2 \xrightarrow{k_{O2}} RM_nOO$ | Oxygen inhibition |

In Table B, parameter values used for the particle polymerization model are presented.

TABLE B

Parameters for Modeling Oxygen Radical Scavenging

| Parameter | Description | Value | Units | Reference |
|---|---|---|---|---|
| $k_p$ | rate constant of propagation for acrylate polymers | 25 | $\frac{m^3}{mol \cdot s}$ | (REF 1.48) |
| $k_{O2}$ | rate constant of the radical scavenging | $5 \times 10^5$ | $\frac{m^3}{mol \cdot s}$ | (REF 1.10) |
| $k_t$ | rate constant for termination of radical species | $2.5 \times 10^3$ | $\frac{m^3}{mol \cdot s}$ | (REF 1.48) |
| $c_{O2}$ | oxygen saturation concentration in the droplet | $1 \times 10^{-3}$ | $\frac{mol}{L}$ | (REF 1.10) |
| $D_{O2}$ | oxygen diffusivity in the droplet | $1 \times 10^{-10}$ | $\frac{m^2}{s}$ | (REF 1.11, 1.50) |
| $\varphi$ | quantum yield of radical | 0.6 | | (REF 1.48, 1.49) |
| $\epsilon$ | molar absorptivity of protons | 20 | $\frac{m^2}{mol}$ | (REF 1.49) |
| $\lambda$ | wavelength number | 350 | nm | lens filter |
| r | droplet radius | 5-50 | μm | varied |
| I | UV light intensity | 5-50 | $\frac{mW}{cm^2}$ | varied |
| $c_{PEGDA\text{-}700}$ | monomer concentration (10-40% vol.) | 160-640 | $\frac{mol}{m^3}$ | varied |
| $c_{initiator}$ | initiator concentration (1-6% vol.) | 66-395 | $\frac{mol}{m^3}$ | varied |
| $\xi$ | fraction of converted monomer | 0-1 | | modeled |
| $N_A$ | Avogadro number (particles per mole) | $6.022 \times 10^{23}$ | $\frac{1}{mol}$ | |
| h | Planck's constant | $6.626 \times 10^{-34}$ | $\frac{m^2}{kg \cdot s}$ | |
| c | speed of light | 299,792,458 | $\frac{m}{s}$ | |

In this COMSOL model study, the ordinary differential equations presented in Table C, were used, and solved simultaneously:

TABLE C

Differential Equations $$\frac{d[PI]}{dt} = -k_d[PI] \text{ where } k_d = \varphi \varepsilon [I]\left(\frac{\lambda}{N_A hc}\right) \quad (1)$$

$$\frac{d[R^*]}{dt} = k_d[PI] - k_t[X]^2 - k_p[X][M] - k_{O2}[X][O_2] \quad (2)$$

$$\frac{d[O_2]}{dt} = -k_{O2}[X][O_2] + D_{O2}\left\{\frac{\partial^2[O_2]}{\partial x^2} + \frac{\partial[O_2]}{\partial y^2}\right\} \quad (3)$$

TABLE C-continued

Differential Equations $$\frac{d[M]}{dt} = -k_p[X][M] \quad (4)$$

$$\xi = \frac{[M_0] - [M]}{[M_0]} \quad (5)$$

The system of equations describe the following physical and chemical foundations of PEGDA photopolymerization within an emulsion droplet. Equation 1 describes the decomposition of the photoinitiator at a rate constant $k_d$, which depends on UV intensity [I], and the sample depth. Because the depth of targeted particles is less 100 μm, light passes through the particle relatively unattenuated and thus we disregard the energy-depth relationship in this model. The incident intensity [I] was measured directly using a radiometer. Equation 2 provides a molar balance of radical species via their formation and termination rates. The termination of free radicals occurs in variety of ways, involving all possible combinations of active species formed during initiation and propagation steps (Table A, steps 2-3). In our model we neglect complex multispecies termination mechanisms including radical trapping. Thus, all radical species (R*, RM*, RM*$_{n+1}$) were lumped into a single radical quantity [X], where [X] terminates through a second order reaction at previously established rate constant $k_t$. Radical specie consumption by oxygen is also accounted for, where each oxygen molecule reacts with a single radical specie at a rate constant $k_{O2}$. In balancing both [PI] and [R*] convective transport is neglected because [PI] is exposed and converted into radicals evenly across the droplet and [R*] is consumed much faster than it is transported. While it has been clearly established that recirculating three-dimensional flows do form in microdroplets as they flow through a microchannel (REF 1.51, 1.52), it was assumed that these interior flows diminish with polymerization, and our experimental results validate this assumption. Two events are addressed by the oxygen specie balance equation (Equation 3): oxygen-radical scavenging and the diffusive oxygen flux into the droplet.

Equation 4 accounts for monomer species [M] consumption or oligomer double bond conversion that drives polymerization. In calculating oligomer conversion, we neglect diffusion due to the macromolecule's large size and immobility, which are exacerbated as polymerization proceeds. Finally, $\xi$ is defined as the total fraction of converted oligomer (Equation 5), allowing aggregate gelation conditions can be evaluated within the droplet. It has been experimentally determined that gelation can occur at about 2% double bond conversion for multifunctional oligomers (e.g. PEG-DA) (REF 1.48, 1.53). Other work has proposed conversion requirements as high as 10% for gelation (REF 1.48). In our analysis we present a complete normalized conversion curve that does not regard fractional cut-off requirements. Gelation requirements tend to be incidental as our polymerized fraction curves display a characteristic stepwise profile with a clear distinction between the polymerized and unpolymerized regions of the droplet (FIG. 3A). Our initial condition for the model is that at t=0, dissolved oxygen everywhere in the droplet region is saturated. For our boundary conditions, oxygen flux occurs at the droplet shell surface only, driven by the saturation limit, with no radial flux at the droplet center.

Experimental

To examine the validity of our reaction diffusion model and establish baseline expectations for droplet polymerization behavior, PEGDA droplets were polymerized within non-purged (ambient oxygen) microfluidic channels. The resulting partially polymerized particles consisted of two distinct fractions (FIGS. 3C, 3D and 3E): a polymerized inner core (indicated by artificial green shading), and a uniform shell of unreacted monomer solution (blue shading). This observed scaling matches model results that predicted a polymerization threshold at a fixed distance from the droplet boundary. At this threshold, a sharp boundary occurs between the discrete polymerized fraction and the remaining liquid fraction. From model results, the boundary between these discrete fractions can be predicted by the steep, step-like profile of the polymerized fraction curve (FIG. 3A) Setting our polymerization criteria at an upper bound of 10% double bond conversion (REF 1.48, 1.53), the polymerized fraction remains relatively unchanged: 0.38±0.01 for 30 µm droplet (FIG. 3A, grey region), corresponding to a ~20 µm thick unpolymerized shell at the droplet interface. While the relative crosslinking fraction varies with droplet size, the absolute thickness of this unpolymerized zone is conserved, reinforcing that it is directly attributed to radial oxygen diffusion from the interface into the droplet (FIG. 3B, red-yellow surface curve). This indicates that a lower critical droplet diameter in which no polymerization would be observed is 40 µm for this particular combination of device and oil.

This result demonstrates control over polymerized particle size in the presence of oxygen-saturated materials. Hydrogel particles may be fabricated at finite length scales by photopolymerizing the core provided the droplet size is larger than 40 µm. Partially polymerized particles may be useful, if one wishes to produce particles without residual surfactant upon their surface. The fully polymerized particles retain a fluorosurfactant layer, which renders them hydrophobic and presents challenges to re-suspending them in aqueous solutions. With partially polymerized particles, we are able to avoid surfactant contamination altogether. After two to three passes of water sonication wash of partially polymerized particles, the liquid oligomer film containing the surfactant can be completely washed off, producing clean particles that appear identical to fully polymerized particles. Partially polymerized particles were produced in fluorocarbon oil and the solution was deposited upon a cover glass slip for visualization throughout the evaporation of the volatile continuous oil phase. As the fluorocarbon oil evaporates, a film of un-polymerized oligomer surrounding the particles coalesces, driving droplet self-assembly into organized hexagonal close-packed structures (FIG. 4D). If the liquid oligomer fraction of the particles has sufficient initiator following the first polymerization, a second exposure can lock these particles into ordered two-dimensional structures. FIGS. 4E and 4F show images of two-pass polymerization of partially polymerized particles with a UV spotlight (Blak-Ray B-100).

Direct and complete polymerization of droplets provides a superior route to controlling particle morphology and the distribution of contents within particles. Using the microjacketed microfluidic device, we polymerized a wide range of size and compositions of PEG-DA hydrogel microparticles. The reduction of oxygen by in situ nitrogen purging enables photopolymerization under significantly reduced PEG content, initiator concentration and UV dose. With nitrogen-jacketed devices, we produced PEG-DA microparticles in fluorocarbon oils with monomer compositions as low as 10%, and particle radii less than 10 µm. Intensity and initiator concentration both play a significant role in photopolymerization of microdroplets, and these two variables were found to be equally effective in accelerating the rate of microparticle polymerization. From the radical specie equation (Equation 2), intensity and initiator concentration appear to be inversely proportional. This seems reasonable, because photo initiator species are in significant excess and during UV exposure these species are converted and consumed very slowly at a rate. Only a few percent (1-2%) are consumed over the entire polymerization period. After the polymerization is complete, a large concentration of photoinitiator remains in the particle. From a functional biomaterial perspective, this is undesirable for applications in which cells are present because initiator cytotoxicity may persist long after polymerization is complete. It some approaches, it may be preferable to increase the optical intensity, while reducing the initiator concentration. In FIG. 4, the effect of increased UV intensity is shown from 10 mW/cm$^2$ to 50 mW/cm$^2$, with time intervals of 2, 4, 6, 8, and 10 seconds respectively. These results demonstrate that with increased UV intensity, the polymerized fraction is increased within the particle and overall gelation time is reduced. As supplementary oxygen is purged and prevented from reaching the droplet, complete polymerization can be achieved, avoiding an unpolymerized region altogether (FIGS. 5B1 and 5B2). In FIG. 5, partially polymerized particles are compared to fully polymerized particles. The model results imply that within the nitrogen jacketed device, and in the absence of oxygen gradients, polymerization proceeds uniformly across the particle.

Conclusions

In this example, we have characterized the photopolymerization of aqueous hydrogel forming solutions within microscale emulsion droplets. The inhibitory effects of oxygen upon microdroplet photopolymerization has been explored using a simple diffusion/reaction finite element model built with COMSOL multiphysics software. Oxygen inhibition introduces a system-dependent length scale threshold below which polymerization is completely prohibited. To overcome this limit, and enable continuous PEG-DA microgel production on a chip, a nitrogen-jacketed microfluidic device for in situ oxygen purging was developed. This platform facilitates the fabrication of PEG-DA microparticles in large quantities. Mild polymerization conditions and cytocompatible droplet compositions were successfully used, demonstrating that this approach may be extended to the production of functional biomaterials. The device and predictive model described here, can be used to define conditions for droplet photopolymerization, providing for partial or complete polymerization of PEG-DA droplets.

Example 2: Methods for Decreasing Oxygen Concentration in Nitrogen-Microjacketed Microfluidic Devices Introduction In this example, nitrogen microjacketed microfluidic devices were modified by adding prepurged channels for Novec 7500 to further decrease the oxygen concentration in device to a lower level. When nitrogen pressure was increased, less photoinitiator (LAP) was needed for the polymerization, and corresponding a higher post-encapsulation viability of cells were obtained. This new approach can be used to produce size-controllable micro hydrogels, which are compatible with the commercial-available flow cytometry methods that provide for a high level of viability of cells after encapsulation.

Materials and Methods

Cell Culture

Human lung adenocarinoma epithelial cells (A549) were used for this research and maintained in low-glucose Dulbecco's modified Eagles's medium (DMEM; Life Technologies, USA) supplemented with 10% fetal bovine serum (Life Technologies, USA), 1% Pen/Strep, and 0.2% Fungizone (Sigma-Aldrich, USA). All cells were cultured in a 5% $CO_2$ humidified incubator at 37° C.

Cell Viability

Cells were encapsulated in micro-sphere hydrogels for viability assessment.

Cells were stained for viability after resuspended into the PBS using a LIVE/DEAD Viability/Cytotoxicity Kit for mammalian cells (Life Technologies, USA) (calcein AM at 2 μM, ethidium homodimer-1 at 4 μM) where live cells stain green and DNA of dead cells stains red. The numbers of live and dead cells were counted using the inverted fluorescence microscope IX-71 (Olympus, USA) and corresponding viability of cells was calculated.

Two-Layer PDMS Device Fabrication

The first layer of the microfluidic device was fabricated on 4 inch silicon wafers (Silicon Inc. USA) using standard photolithographic methods, with a SU-8 2015 photoresist (MicroChem, MA, USA) spin at 1045 rpm to create coat with the thickness of 30 μm. Features were created by exposure to UV light (Omnicure S2000, USA) under the cover of the photomask designed using AutoCAD and printed out using a laser printer (CAD/Art Services, OR). The second layer of the microfluidic device was fabricated using the same methods, except the coat was made from SU-8 100 by spinning at 3000 rpm to obtain a thickness of 100 μm. Polydimethylsiloxane (PDMS, Dow Corning, MI) devices were casted using a silicon wafer, and cured devices with inlet and outlet holes were made with a 20 G dispensing needle (McMaster-Carr) and bonded to glass slides following oxygen plasma treatment. To create a hydrophobic surface for droplet generation, Aquapel (PPG Industries) was briefly injected into the device and flushed out with nitrogen prior to the experiment.

Prepolymer Precursor Solution

Cell suspensions were prepared by detaching from culture surfaces using 0.05% trypsin/ethylenediaminetetraacetic acid, disassociated into single cells, and then resuspended at an effective cell density, $3\times10^7$ cells/mL in heavy DMEM, which was adjusted to have a specific gravity of 1.06 g/mL by Opti Prep density medium (Sigma-Aldrich, USA). Monomer mixture contains of 45 total wt % macromere in phosphate buffered saline (PBS, pH 7.4, Sigma-Aldrich, USA), consisting of 75 mol % poly (ethylene glycol) monoacrylate (PEGMA, Mn≈400 Da; Monomer-Polymer and Dajac Labs), and 25 mol % poly(ethylene glycol) diacrylate (PEGDA, Mn 3400 Da; Alfa Aesar, MA) (REF 2.1). Lithium phenyl-2,4,6-trimethylbenzoylphosphinate (LAP) got from Dr. Melissa Pope's Lab, was dissolved in PBS and used as photoinitiator in this research. Prepolymer precursor solution was mixed in 1.5 ml centrifugal tube or in device to get the final concentration of monomer mixture to 15 total wt %, cell density to $1\times10^7$ cells/mL, and a certain LAP concentration depending on the experiment.

Microfluidic Cell Encapsulation

For microfluidic encapsulation, three components, monomer mixture, cells suspensions, and LAP, were loaded into syringe and inject into device at 0.33 μL/min, separately, and fully mixed in device. Simultaneously, fluorocarbon oil, Novec 7500, containing 2 wt % Pico-Surf (Dolomite, USA) was also injected into the device as an oil phase at 2 μL/min and 7 μL/min for the first layer and second layer of the device, respectively. At the droplet-generating nozzle in the first layer of the device, the aqueous prepolymer precursor was broken into 40 μm-diameter droplets in oil and got into the second layer of the device, where droplets were continuously polymerized on channel by exposure to UV light (352-402 nm, 100 mW/cm2, 0.025 s; Lumen 100S) before exiting the device. Microsphere hydrogels collected from the device were separated from oil and washed on a 35 μm cell strainer using PBS with 0.1 wt % Pluronic F-127 (Sigma-Aldrich, USA) to remove any un-polymerized components, which then were resuspended into cell culture medium with 0.1 wt % Pluronic F-127 and cultured in 24-well plates. All experiments were performed with quadruplicate wells for each condition.

Cell Encapsulation in Bulk

Mixing the cell suspension, monomer mixture, and LAP get prepolymer precursor solution. Added 100 μL prepolymer precursor solution to Novec 7500 with 2% Pico-surf or light Mineral Oil with 2% Span 80 (Sigma-Aldrich, USA), and then vortex for 10 s to get droplets, which were polymerized by exposed to UV light for 2 s. The hydrogels were separated from the oil and washed using the same methods.

COMSOL Model Description

Free radical photopolymerization model was built to examine and confirm peroxide radical effects on cell viability in hydrogel microparticles. The finite element numerical model was created in COMSOL multiphysics software using below outlined parameters and settings. A line drawn in 1-D axisymmetric space dimension was set to represent a distance from droplet center to a side. Time dependent transport of diluted species study across the line was selected for model basis with characteristic mass transport equation as follows:

$$\frac{\partial c_i}{\partial t} + \nabla \cdot (-D_i \nabla c_i) = R_i$$

$$N_i = -D_i \nabla c_i$$

In our droplet polymerization model, the main reacting species were: polymer, initiator, free radicals, and oxygen. First, the initiator species were converted into free radicals or in other words photo polymerization's first step—initiator photolysis. Next, free radical species were allowed to react in three different pathways: 1) monomer chain initiation/propagation, 2) radical self-termination, and 3) peroxide radical formation. Additionally, oxygen was set to freely diffuse into the droplet, and react with free radicals present. From experimental observations of nitrogen jacket effectiveness, assumption was made that the droplet was significantly diluted in oxygen concentration (0.01 mol/m$^3$).

The Reaction constant for radical oxidation 2.5-6.8×$10^7 M^{-1} s^{-1}$ (REF 2.2-2.6).

LAP has a significant absorbance at 365 nm (molar extinction coefficient (absorbtivity) at 365, c=218$M^{-1}cm^{-1}$ (REF 2.7).

Results and Discussion

Size Distribution and Uniformity of Microsphere Hydrogels

There are various methods to encapsulate cells in microsphere hydrogels, such as in bulk (REF 2.8) using different oil phases or in microfluidic devices (REF 2.9). In this research, cells were encapsulated in microsphere hydrogels either in bulk (FIG. 6A) or in microfluidic devices (FIG. 6B) using Mineral oil with 2% Span 80 and Novec 7500 with 2% Pico-Surf, respectively. LAP was used as photoinitiator in all above experiments, and all the final concentrations of LAP were 1 wt %. Microsphere hydrogels were separately from the oil phase and resuspended into PBS with 0.1% Pluronic F-127, and then the diameter of those hydrogels were measured using ImageJ, based on that the size distribution (FIG. 6C) and uniformity (FIG. 6D) were calculated and plotted. The post-encapsulation cell viability was assayed for those cells encapsulated using different methods and oils. Considering the results of size distribution and uniformity of hydrogels got using different methods, using the Novec 7500 with 2% Pico-Surf in microfluidic devices have a good advantage for cells encapsulation. However, the corresponding post-encapsulation cell viabilities assay showed the post-encapsulation viability of cells conducted using Novec 7500 was really bad, where all cells were dead (FIG. 6E).

Effects of Single Factors on Post-Encapsulation Viability of Cells

To identify which factor or step killed all the cells, a series of controls were conducted to test the effects of factors on the post-encapsulation viability of cells using Mineral oil and Novec 7500, respectively. Cells, UV, Monomer, and LAP were sequentially added to the cell encapsulation system, and the corresponding cell viability was assayed. The results showed the post-encapsulation cells viability is zero in Novec 7500 versus 85% in Mineral oil (FIG. 7). Compared the characteristics of these two oil phases, we found there is a huge different between the oxygen solubility in Mineral oil and Fluorinated oil, which are 0.134 (REF 2.10) and 12 mol/m$^3$ (REF 2.11), respectively. Then we put forward the assumption that there was enough peroxide radicals were produced during the polymerization due to the high oxygen solubility in Novec 7500, which made all the cells dead.

Cell Encapsulation Using the Nitrogen Jacketed Two-Layer PDMS Device

As discussed before, the process of radicals scavenged by oxygen is the potential factor, which killed all the cells during cell encapsulation. To test this hypothesis, a nitrogen jacked two-layer device was designed, where all the channels in device were jacked and the oil phase was prepurged by nitrogen. Employing the new device, the oxygen concentration within the prepolymer precursor mixture could be controlled by varying the pressure of the jacked nitrogen. As it showed in FIG. 8, we can easily control the size of droplets generated at the nozzle, and also the number of cells per droplet by manipulating the flow rates of components. To examine the effect of the oxygen concentration in prepolymer mixture on the polymerization, the minimum LAP needed for the polymerization with different pressure of the jacked nitrogen were tested, and it showed in FIG. 9A, lower LAP concentration needed as the nitrogen pressure increased from 0 to 9 psi. The results showed that by employing the nitrogen jacked two-layer device, oxygen concentration in droplets could be controlled by varying the pressure of nitrogen. To test if the intermediates produced during the radical scavenged by oxygen are the factor which killed the cells, a series of experiments were conducted under a constant nitrogen pressure (7 psi) but with different LAP concentration, ranging from 0.1% to 0.8%. As the resulted showed in FIG. 9B, the post-encapsulation viability of cells was decreasing as the increasing of the LAP concentration in droplets. Studies showed that peroxide radicals have some harmful effects on cells including damage of DNA (REF 2.12), lipid peroxidation (REF 2.13), oxidation of amino acids in protein (REF 2.14), and inactive specific enzymes by oxidation of co-factors (REF 2.15-2.17). All above results showed some intermediates were produced when radicals were scavenged by oxygen, and the concentrations of these intermediates were related with the post-encapsulation viability of cells.

Prediction of the Peroxide Radical Amount Using COMSOL

The cumulative amount of peroxide radical and regular radicals were predicted using COMSOL based on those available known parameters. The results showed there were more radicals and peroxide radicals were produced when we increased the LAP concentration (FIG. 10A and FIG. 10B). And the relationship between the amount of peroxide radicals and post-encapsulation cells viability were plotted (FIG. 10C). Compared the two figures, FIG. 9B and FIG. 10C, we can confirm that the amount of peroxide radicals produced during the polymerization was the factor, which have a significant effects on the post-encapsulation cells viability.

Conclusions

We demonstrated a new approach to produce encapsulated cells that integrates uses a method of controlling the production of microsphere hydrogels by varying the composition of components in a solution of prepolymer precursors. This approach will facilitate the high throughput screening of encapsulated cells in various microenvironments. We demonstrated that a nitrogen microjacketed microfluidic device allows us to control the oxygen concentrations in the prepolymer precursor solution by varying the nitrogen pre-purge time and pressure, permitting the polymerization of droplets as microsphere hydrogels under different levels of concentration of LAP, without the size limitations observed in other methods for the production of microsphere hydrogels. With the nitrogen microjacketed microfluidic devices, microsphere hydrogels with diameter around 40 µm can be produced. The minimum LAP concentration required for the photoinitiated polymerization in device was determined by manipulating the pressure of the prepurging nitrogen, showing that at a higher prepurging pressure, a lower LAP was needed for the polymerization. The relationship between oxygen concentration in prepolymer precursor solution and post-encapsulation viability of cells was demonstrated by changing the LAP concentration at a constant pre-purging pressure, with a constant oxygen concentration within the solutions. The results demonstrated that during the process of radical scavenging by oxygen, some reactive intermediates, including peroxide radicals, were produced, which have an effect on the viability of post-encapsulated cells. The concentrations of peroxide radical under a constant oxygen concentration with different LAP concentrations were modeled using COMSOL, demonstrating that the concentration of a peroxide radical appears to affect the viability of cells after encapsulation.

Example 3: Templating Hydrogel Inverse Opal Architectures with Photodegradable Microparticles Inverse colloidal crystals (ICCs) are the product of a lost wax fabrication method in which colloidal particles are assembled into ordered matrices in the presence of a liquid continuous phase. Following solidification of the continuous phase, particles are subsequently extracted, leaving behind a structured pore network. ICCs have been developed for a variety of scientific and technological applications, yet their utility remains limited by harsh processing conditions required to solubilize particles for pore framework formation.

In this example, we demonstrate a new approach to the production of ICCs based on a method involving synthesis of photodegradable polyethylene glycol diacrylate particles. Since degradation of particulate phase requires only optical illumination, particle assemblies can be eroded within tightly confining microchannels, creating microfluidic-integrated ICCs. Photodegradable particle assemblies were used to produce patterned porous structures composed of polyethylene glycol hydrogel networks and interconnected objects and voids. Use of gentle, non-invasive methods to erode photodegradable PEG particles within structural assemblies also allows secondary objects to be embedded within the pores of the ICC. These approaches are also cytocompatible, facilitating the production of functional biomaterials.

Introduction

Polyethylene glycol (PEG) hydrogels have become widely adopted scaffolding materials for tissue engineering mainly because these materials have compatible mechanical properties, water-based composition, and tunable chemical structures. Chemical structure characteristic such as monomer length, governs polymer crosslinking density, and it allows controlling of fundamental mass transport and mechanical properties in the scaffold (REF 3.1).

Micro-size inclusions have been successfully integrated within the hydrogels in past by introduction of internal phase micro templates or features (i.e., particles, fibers, meshes, bubbles) during the fabrication process. Well documented methods include phase separation, gas foaming, three-dimensional printing, emulsion or sphere templating, and porogen leaching (REF 3.2, 3.3).

In this example, we demonstrate the fabrication and in situ assembly of photodegradable PEG particles to create ICCs inside microchannels. The microchannels serve as guides to orient particles within the network and the structure of the ICC. Other functional objects can also be permanently seeded into the ICC network, since the erosion of particles is passive Experimental Soft Lithography Photodegradable PEG Synthesis The photodegradable macromer is synthesized from polyacrylated PEG chains that contain photolabile o-nitrobenzylether moieties. The full synthetic protocol has been described elsewhere (REF 3.5).

Hydrogel Particle Fabrication and ICC Network Fabrication

Photodegradable hydrogel microparticles were produced in a microfluidic device by dynamic photo-polymerization of polymer containing aqueous microdroplets (FIG. 11). Microdroplets were formed via snap-off mechanics principles in a classical T-junction channel microfluidic device (REF 3.4). In this example, we used ~100 um thick PDMS microfluidic devices for particle production and filtration. Continuous phase to dispersed phase flow ratio methods allowed us to control the droplet size, and permitting us to control the residence time needed to photo-polymerize droplets in a microfluidic serpentine belt channel. We used fluorocarbon oil (Novec 7500+2% Krytox surfactant) as a continuous phase, and prep polymer aqueous solution containing polyethylene glycol diacrylate (PEGDA)-based photodegradable macromer as a dispersed phase. Photopolymerization of droplets was carried out in a serpentine belt channel, where hydrogel particles formed by redox-initiated, acrylate free-radical chain UV photopolymerization of PEG-diPDA cross-linking molecules. Lithium phenyl-2,4,6-trimethylbenzoylphosphinate (LAP) at concentrations of ~0.5% by weight was used as an initiator. LAP has a good solubility in water, is relatively cytocompatible, and has an improved absorbance spectrum at longer UV wavelengths (including LP 405) compared to other initiators (REF 3.6). Polymerized particles suspended in fluorocarbon oil were separated out using centrifuge, followed by re-suspension in deionized water. Particle-oil separation can also be directly achieved in a microfluidic filtration device. Flow packing manipulations with produced particles were performed using filter-based microfluidic devices (FIG. 12). Packed particle assemblies on a microfluidics chip were infused with a non-degradable polyethylene diacrylate (PEGDA, MW-700, Sigma Aldrich) aqueous-based solution (3% wt. 2-hydroxy-2-methylpropiophenone (Sigma Aldrich) as initiator), and further UV-polymerized under LP-405 microscope filter (FIG. 13). Subsequent degradation of primary hydrogel particles was achieved by secondary UV exposure using DAPI microscope filter at 365 nm (FIG. 14). The photolabile group, ethyl 4-(4-(1-hydroxyethyl)-2-methoxy-5-nitrophenoxy)butanoic acid, is responsible for photo-degradation of particles.

Characterization

The porous hydrogel structures were observed and verified using standard microscopy techniques, including scanning electron microscopy, laser confocal microscopy, and bright field microscopy.

Results and Discussion

Packing in Microfluidic Channels

Flow induced microfluidic packing is an effective method for passively arranging microspheres into organized assemblies (REF 3.7, 3.8). To facilitate the production of particle-based composite materials, it is important to recognize that porosity and particle packing spatial arrangement patterns are key elements that determine the structural and global mechanical properties of a final composite assembly. Experiments performed in microfluidic devices allowed us to visualize and monitor particle flow patterns and packing phenomena in real-time. In FIG. 12 (on left), 2-D organized close packing configurations are illustrated, demonstrating a function of the angle between two neighboring hydrogel microparticles. In our experiments, on an "unbounded" plane we observed packing configurations that fall between two packing extremes: cubic lattice packing, and hexagonal close packing. Cubic lattice packing produces least dense structures, with packing density of 0.5236 ($\pi/6$), where angle between two neighboring particles is 90° (REF 3.9). Particles are in contact with 4 neighboring particles, and 6 neighboring particles in 2-D and 3-D respectively (also referred as coordination number). Cubic lattice formations are rare to initiate and difficult to reproduce when using induced flow conditions. Cubic lattice formations were only observed in 2-D, in isolated regions near the device walls, or around unintentional contaminants that distorted the original configuration. A maximum of 3 particle rows of cubic lattices were found at a time. In nearly every packing experiment we conducted, the flow induced packing in a 2-D plane produced closely-packed hexagonal arrangements. During conditions that lead to continuous colloid growth, distorted packing arrangements always "self-heal", and eventually (within ~5 rows of particles) return to hexagonal close packing configuration. Hexagonal sphere packing has been demonstrated to be is the densest form of packing obtainable, with a 2-D planar packing density of 0.6046 ($\pi/3\sqrt{3}$), and with 3-D packing density of 0.74048 ($\pi/3\sqrt{2}$) (REF 3.10). The neighboring particle number for hexagonal packing in 2-D is 6, but in 3-D environment it is 12 (REF 3.10). Supplementary 2-D particle packing experiments were also conducted in narrow confined channels with of varying widths (FIG. 12, right). We found that particles in narrow microchannels assemble passively in predictable periodic structural lattices based on carrier fluid flow streamlines that are unidirectional, consistent with previous observations made by Kumacheva and Vanapalli. Since the flow in microchannels is laminar, particles move in track with flow streamlines, and passively land in locations where streamlines convene and become kinetically entrapped. The energy of particle in hydrodynamic drag field is larger than the energy of particle kT (where kT is a product of the Boltzmann constant, k, and the temperature, T). Interstitial voids that have been created on behalf of previously deposited particles (REF 3.7, 3.8) are foci for fluid streamlines, and therefore these voids work as location templates for positioning of succeeding particles. In FIG. 12 (on right), we demonstrate the relationship between packing density and the adjacent particle angles.

Particle Erosion

In FIG. 13, we illustrate two relative time scales for complete erosion of hydrogel particles (20% wt. PEGdiPDA, 0-80 seconds), and for continuous phase full polymerization (40% PEGDA-700, 0-12 seconds). Photodegradation of particles suspended in ethanol solution was carried out in filter microfluidics device (with lightly induced flow from left to right). From the time-lapse images, we observed that particles degraded uniformly, and were effectively dissolved and carried away in ethanol. For polymerization of continuous phase, we observed robust polymer gelation indicated by hue color change and distinct boundary solidification surrounding the particles. in most cases during polymerization, we noticed irreversible deformation of degradable particle pore interphase. For closely packed structures, we observed that particle circular boundaries transformed into hexagons. If particles were loosely spaced (as seen in SEM images, FIG. 3), deformations of interstitial space were averted, and pores remained circular. The reason for deformation of original shape may be caused by polymer or particle volume changes during polymerization/degradation process. From ImageJ analysis, the measured particle area did not change significantly, suggesting that the continuous phase hydrogel is confronted by similar tension forces observed in bee honeycombs. As described by Karihaloo et al., honeycombs are initially made of cells that are circular in cross section and are packed together like a layers of spherical particles. The packing of the honeycomb wax structures, softened by the heat of the bees' bodies, is obtained pulling wax into hexagonal cells by surface tension forces at the junctions where three connecting walls meet (REF 3.11). Similar forces may be responsible for the effects we observe during polymerization of microparticles in a microscopic environment (FIG. 14).

Microfluidics assisted scaffold assembly also provides many open strategies for tuning structural and mechanical properties of composites. The packing density of our mono-sized degradable particle structures is 0.61 (2-D) and 0.74 (3-D). In experiments involving a continuous polymer phase infusion/polymerization and subsequent template particle erosion, our scaffold materials have equivalent porosities of 0.61, and 0.74 respectively. These scaffolds do not have to be limited to these singular porosity values. These values are our upper theoretical porosity limit for mono-sized particles, and we are able to control and attain scaffolds with full range (0-0.74) of porosities by fractionally adding and mixing non-degradable particles with degradable particles. By adding non-degradable particles or particles that degrade very slowly, we are able to control and design strictures that have porosity and mechanical properties that are suitable for use in specific tissues of the body.

Polystyrene microspheres (Fluoro-Max, Thermo Scientific, D=5 um, shaded lightly green) encapsulated within larger PEGdiPDA degradable particles are illustrated in Figure EX 3-5. Passive inclusion of necessary constituents within formed pores of the porous scaffold can be obtained after degradation of the PEGdiPDA template particles.

Conclusions

New techniques for producing composite porous hydrogels from photodegradable particles were demonstrated.

While the preferred embodiments of the invention have been illustrated and described in detail, it will be appreciated by those skilled in the art that that various changes can be made therein without departing from the spirit and scope of the invention. Accordingly, the particular arrangements disclosed are meant to be illustrative only and not limiting as to the scope of the invention, which is to be given the full breadth of the appended claims and any equivalent thereof.

Example 4: Cellular Response to Hydrogel Photopolymerization in Microfluidic Emulsion Droplets Encapsulating cells within biocompatible materials is a promising strategy for tissue engineering and cell-based therapies. Extensive interest in microfluidic-enabled cell encapsulation via the photopolymerization of PEGDA-based microparticles has more recently emerged. Performing cell encapsulation within microfluidic devices allows the precise control of the physical properties of the encapsulant material and microenvironmental conditions of the cells. The photopolymerization of PEGDA within gas permeable polydimethylsiloxane (PDMS) microfluidic devices can be successfully conducted employing a recently developed nitrogen-jacketed device, in which the inhibition of oxygen of radical chain polymerization has been mitigated. Compared to bulk polymerization in which cells were suspended in a static hydrogel-forming solution during gelation, encapsulating cells via microfluidic processing exposes cells to a host of potentially deleterious stresses such as fluidic shear, transient oxygen depletion, elevated pressures, and UV radiation exposure. In this example we have examined the effects of these factors upon the viability of cells encapsulated by microfluidic emulsification and photopolymerization. It was found that the fluid shear rate during microdroplet formation did not have an obvious effect on cell viability until a threshold level was reached. Effects of UV radiation time and intensity on cells, however, are more complex, as they have unequal contributions to the cumulative rate of peroxy radical which is directly related with cell viability. A reaction-diffusion model was built to calculate the accumulative generated peroxy radicals with various UV light intensity and radiation time, which were consisted with the experiment results. The results obtained in this research provides a guide to further decrease the physical damage imparted on cells during the encapsulation process via microfluidic processing and expands the applications of the established platform.

Introduction

Encapsulation within synthetic hydrogels is a promising and widely used approach to immobilize and protect cells from mechanical stresses, and deleterious macromolecules, like macrophages and antibodies, while allowing bidirectional diffusion of nutrients and wastes. Encapsulated cells can be used in tissue engineering and cell-based therapies by locating cells at injury sites or continuous delivery of therapeutic reagents for some chronic diseases, and also enable the potential for xenotransplantation. Cell encapsulation has been explored and employed as cell-based therapies for type 1 diabetes, osteodifferentiation, vascular differentiation, and cartilage formation over the past decades. Various natural and synthetic polymer hydrogels have been explored for cell encapsulation including hyaluronic acid agarose, dextran, and alginatepolykysine. Poly(ethylene glycol) (PEG)-based monomer has been widely employed and characterized for cell encapsulation due to their excellent biocompatibility, mechanical property, tunable and readily modified network. And the incorporation of acrylate end groups has significantly expanded the application of PEG-based hydrogels on cell encapsulation, in which the gelation of hydrogel-forming solution can be achieved via UV light exposure, allowing the precisely temporal and spatial control over the hydrogel properties.

Recently, microencapsulating cells within hydrogels ranging from 100 μm to 500 μm have emerged as an area of intense research interest with broadly utility in therapeutics, material synthesis, and drug discovery, in which the sensitive and signal strength can be boosted to 2 orders of magnitude comparing to the tradition methods due to the large surface to volume ratio. The advanced development of microfluidic technology promises a breakthrough application in cells microencapsulation and high throughput handling of cells, in which highly monodisperse surfactant-stabilized aqueous microdroplets were formed at a junction of microfluidic channels or in coaxial capillaries. The introduction of polydimethylsiloxane (PDMS)-based microfluidic devices has expanded the applications of microfluidic device on bioengineering related researches due to its high gas permeability and transport rate and quickly and inexpensively fabrication via replica molding from a photolithohraphically-patterned master. Previous research showed the radical chain polymerization of PEGDA is strongly inhibited by the oxygen in system and in air especially when the experiment was conducted in the gas permeable PDMS-based microfluidic device using the oxygen abundant fluorinated oil as the continuous phase. The oxygen inhibition makes cell encapsulation in microfluidic device even harder due to the generated peroxy radicals during the oxygen scavenging process, which will imparted harmful effects to cells such as lipid peroxidation, amino acids oxidation, inactivation of specific enzymes, and damage of DNA. Fully polymerized PEGDA-based microparticles has been successfully obtained via photopolymerization using the nitrogen-purged microfluidic device described herein by purging the oxygen out of the system to mitigate the oxygen inhibition of gelation. This nitrogen-purged device was further developed and we recently developed the two-layer nitrogen-purged microfluidic device for cells encapsulation with a significantly improved cell viability, enabling precisely control the oxygen concentration in fluids through regulating the nitrogen purging pressure. The advancement of inertial focusing enables the alignment of cells to well defined lateral and longitudinal locations without the need for external force, in which cells were forced to travel rapidly through a high aspect-ratio microchannel. This technology allows the single cell encapsulation in microdroplets or microparticles for high throughput analysis of cellular response or products in microfluidic device.

Cells were exposed to various potential deleterious effectors during the cell encapsulation process on microfluidic device via photopolymerization of PEGDA. Cellular response to those individual factors, however, have not been evaluated In this work, we evaluated the effects of fluid shear rate, cells residence time in microfluidic device, nitrogen purging pressure, UV exposure intensity and time upon cell viability. Compared to the increasing UV exposure intensity, the increase UV radiation time has more deleterious effect on cell viability. A finite-element reaction-diffusion model was utilized to calculate the cumulative concentration of peroxy radicals during the UV exposure, and the results showed they have unequal contributions to the cumulative rate of peroxy radical which is directly related with cell viability, which was determined by the residue oxygen and its diffusion rate in fluids. By evaluating the cellular response to those factors, we provide directions to further increase the postencapsulation cell viability during the encapsulation process via microfluidic processing and expand the applications of the on-chip cell encapsulation platform.

Materials and Methods

Cell Culture

Human lung adenocarcinoma epithelial cells (A549) were routinely cultured using low-glucose Dulbecco's modified Eagles's medium (DMEM; Sigma-Aldrich, USA) supplemented with 10% fetal bovine serum (Sigma-Aldrich, USA), 1% penicillin/streptomycin, and 0.2% Fungizone (Life Technologies, USA) at 37° C. and 5% CO2 in a humidified incubator.

Microfluidic Device Fabrication

Master cast of the microfluidic device used this work were fabricated using soft lithography techniques or according to the protocol developed in our group. For the cast with only one-layer feature, a silicon wafer (Silicon Inc. USA) was coated with SU-8 2015 negative photoresist (MicroChem, MA, USA) at a thickness of 30 μm. A photomask with design features (CAD/Art Services, OR) was put onto the wafer following by exposing to collimated UV light (Omnicure S2000, USA) to achieve the polymerized features, in which the uncured photoresist was removed using developer (Propylene glycol monomethyl ether acetate, Sigma-Aldrich, USA). As to the fabrication of the cast of the two-layer nitrogen-purged microfluidic device, the feature of the first layer (30 μm) was first fabricated using the previous described method, and then a second planar flow network was patterned on the previous made wafer using SU-8 100 (MicroChem, MA, USA) at thickness of 100 μm by the same method. Microfluidic devices were casted by pouring Polydimethylsiloxane (PDMS, Dow Corning, MI) on the patterned silicon wafer and the cured elastomer was peeled off from the wafer and punched by a sharpened 20 G dispensing needle Polydimethylsiloxane (Brico Medical Supplies, INC., USA) to introduce the inlet and outlet holes. The PDMS replicas were bonded to glass slides using oxygen plasma. Before the experiment was conducted, Aquapel (PPG Industries) was briefly injected into the device and flushed with nitrogen to obtained a hydrophobic surface for aqueous droplet generation.

Macromolecule Synthesis and Hydrogel Photopolymerization

A549 cells were grown to 80 to 90% confluence according to the previous described protocol. Confluent cells were trypsinized using 0.05% trypsin/ethylenediaminetetraacetic (Lifetechnologies, USA), pelleted, and then resuspended in heavy phosphate-buffered saline (PBS, Sigma-Aldrich, USA) (~3×10$^7$ cells/mL), which was adjusted using Opti Prep density medium (Sigma-Aldrich, USA) to have a specific density of 1.05 g/mL. 45 total wt % macromer mixture was prepared in PBS consisted of 75 mol % polyethylene glycol monoacrylate (PEGMA, Mn≈400 Da; Monomer-Polymer and Dajac Labs) and 25 mol % poly (ethylene glycol) diacrylate (PEGDA, Mn≈3400 Da; Jenkem Technology, Beijing, China). {Weber: 2008 wm} The UV initiator lithium phenyl-2,4,6-trimethylbenzoylphosphinate (LAP) was synthesized as previously described {Fairbanks: 2009 kz} and dissolved in PBS with a concentration of 0.3 wt %. The cells in heavy PBS, UV initiator and macromere solution were injected into microfluidic device separately, in which they were fully mixed to form the hydrogel-forming polymer solution consisting of $1\times10^7$ cells/mL, 0.1 wt % LAP, and 15 total wt % macromer.

Cell Viability Assessment

Cells encapsulated in microdroplets or microhydrogels were separated from oil and washed on a 5-μm cell strainer (pluriSelect, USA) using PBS with 0.1 wt % Pluronic F-127 and resuspended in PBS. Cells viability was determined using a LIVE/DEAD Viability/Cytotoxicity Kit for mammalian cells (Life Technologies, USA), in which staining solution (2 μM calcein AM and 4 μM ethidium homodimer) were added and incubated for 15 min at room temperature. The stained hydrogels were washed with PBS and the number of live and dead cells were counted using an inverted fluorescence microscope IX-71 (Olympus, USA), and the corresponding cell viability was calculated.

Flow Rate and Residence Time

Cells and hydrogel-forming macromere solution were mixed in device and then pinched by the continuous phase, Novec 7500 containing 2 wt % Pico-Surf (Dolomite, USA), to form microdroplets at the nozzle area in microfluidic device. The shear forces were varied by regulating the flow rates of the dispersed phase and the continuous phase, and then cellular response to the changing of stress forces was evaluated by assaying the corresponding cell viability. With a constant fluids flow rate and nitrogen-purging pressure ($P_{N2}$=7 psi), the residence time of cells in microfluidic device was varied by changing the outlet positions, in which the effects of residence on cell viability was illustrated.

Nitrogen-Purging Pressure

The cellular response to the nitrogen-purging pressure also was evaluated by varying the purging pressure and the corresponding cell viability. When the nitrogen purging pressure less than a certain point, fully polymerized PEGDA-based microparticles could not been achieved, in which we separate the cells instead of microparticles from the oil using the previous described protocol and then assay cell viability.

UV Radiation Intensity and Time

The effects of UV radiation on cell viability was decoupled into radiation time and radiation intensity in this work, and were evaluated separately. A mask with specific transparent area was put upon the microfluidic device to control the UV radiation time, and the UV radiation intensity was regulated using the Omnicure S2000, in which the radiation time was calculated based on the total fluid flow rate and the geometry of the channel. The effect of UV radiation time on cellular viability was evaluated by varying the radiation time from 1.1 s to 9.9 s with a constant UV radiation intensity, 120 W/cm². Cellular response to UV intensity was assessed by assaying cell viability corresponding to different UV intensity exposure ranging from 60 to 600 W/cm² with a constant UV exposure time, 1.1 s.

Photopolymerization Modeling

A reaction-diffusion model of free radical photopolymerization was constructed and used to quantify peroxy radical accumulation and get further interpret of the effects of UV exposure upon cell viability, in which the peroxy radicals were assumed inert after produced. A finite element numerical model was created in COMSOL multiphysics software using parameters and setting can be found in the supplementary information. A line drawn in 1-D axisymmetric space was set to represent a distance from droplet center to the droplet interface. A time-dependent transport of diluted species study was selected across the line as the model basis using the flowing differential equations, in which they were solved simultaneously.

TABLE D

Flowing Differential Equations

| | |
|---|---|
| $R_I = -k_d[I]$ | (6) |
| $k_d = \varphi\varepsilon(\lambda, I)I\left(\dfrac{\lambda}{N_A hc}\right)$ | (7) |
| $R_M = -k_p[X][M]$ | (8) |
| $R_X = k_d[I] - k_t[X]^2 - k_{O_2}[X][O_2]$ | (9) |
| $R_{O_2} = -k_{O_2}[X][O_2]$ | (10) |
| $R_P = k_t[X]^2$ | (11) |
| $R_{ROO} = k_{O_2}[X][O_2]$ | (12) |

In our droplet photopolymerization model, the main reacting species were: macromer, initiator, free radicals, and oxygen. All reaction parameters used in this model were obtained from the literature. Based upon experimental observations of nitrogen jacket effectiveness, an assumption was made that the oxygen concentration in a droplet within a purged microchannel was significantly dilute. The pressure-dependent oxygen concentration, 0.01 mol/m³, was calculated using the data in this experiment and the COMSOL model created in our lab.

Results and Discussion

Cellular Response to Fluid Shear and Residence Time

Figure 16:
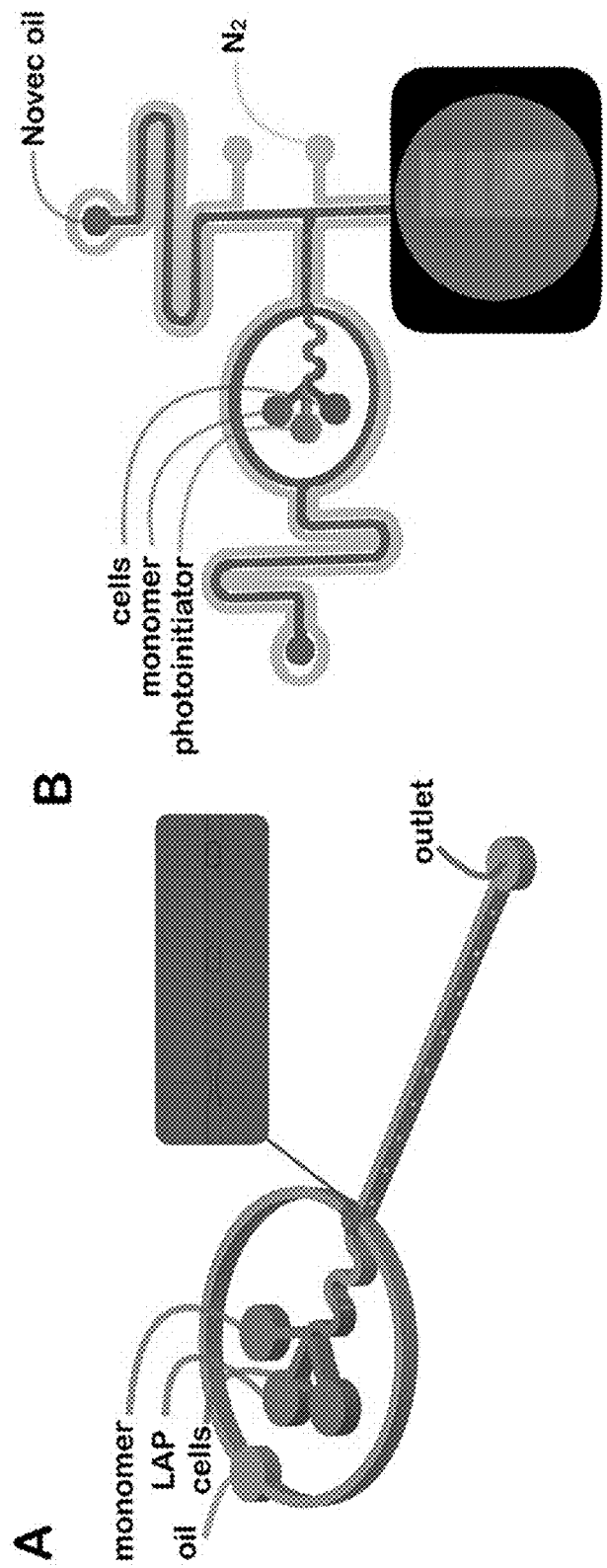
FIG. 16. provides a schematic of the device used in Example 4. (A) Schematic figure of the microfluidic device used to assess cellular response to fluids flow rate. (B) Schematic figure of the microfluidic device used to evaluate UV exposure intensity and time upon cell viability, in which the transparent size on the mask was used to regulate UV exposure time.
Figure 17:
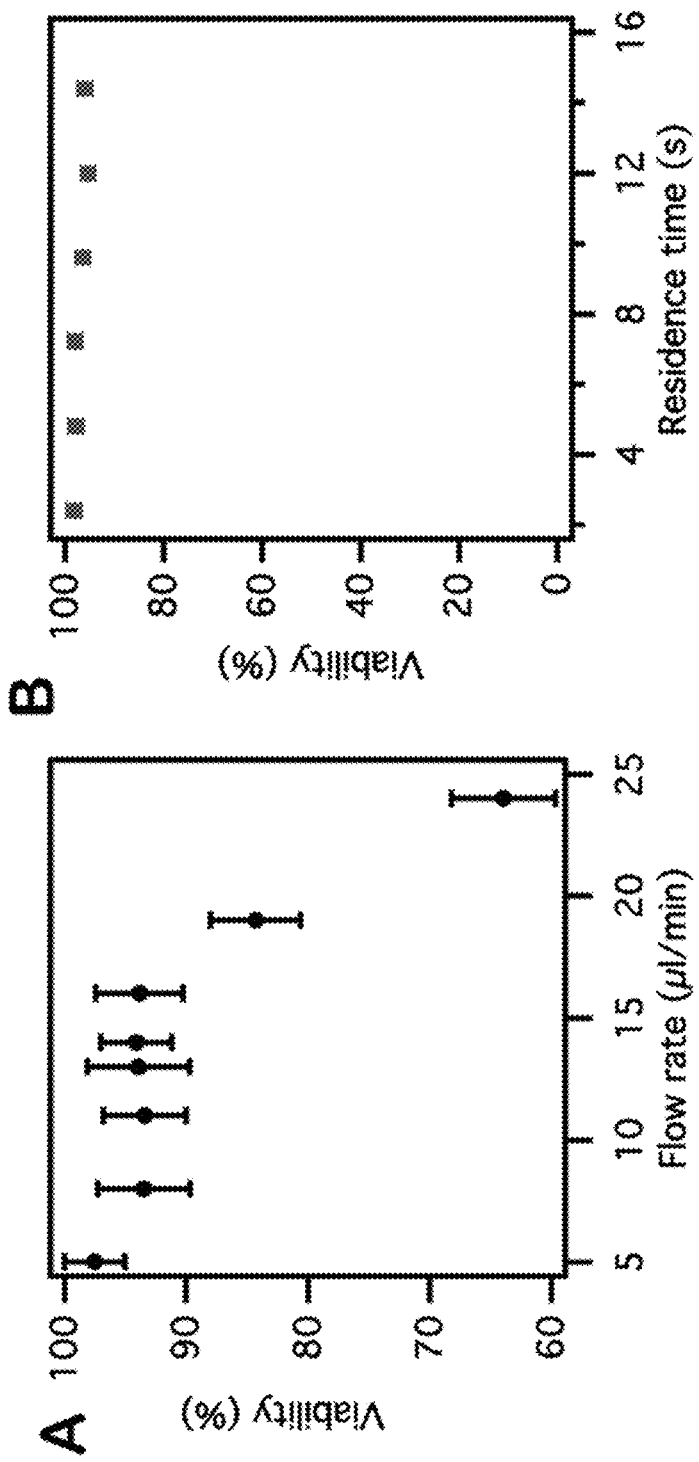
FIG. 17. demonstrates cellular response to flow rate and residence time in a microfluidic device. (A) The effect of flow rate on cell viability. (B) The effect of residence time of cells traveling in device upon cell viability, in which the total flow rate was 5 µL/min and the nitrogen purging pressure is 7 psi.

Cells in hydrogel-forming macromere solution were pinched by the continuous phase, Novec 7500 containing 2 wt % Pico-surf, to form microdroplets at the nozzle of the microfluidic device (FIG. 16A). Fluids flow rate has been shown have effect on behavior and functions of bacteria, and fluids flow rate were also related with cells rotation rate in fluids and the stress force imparted on cells, which could cause physical damage to cells. The flow rates of the hydrogel-forming solution and oil phase were varying as showed in the Table E. Microdroplets were collected and cells were separated from oil phase using the previous described method. The effect of fluids flow rate upon cell viability was mapped (FIG. 17A), in which as the increasing of flow rate, there was no obvious change of cell viability until the flow rate reached 16 μL/min. And then as the fluids flow rate was increased further, cell viability was dropped sharply. The results illustrated that the relatively low flow rates of oil and hydrogel-forming solution did not have effects on cell viability, but when it get to a threshold, it was harmful to cells in which physical damages were caused.

TABLE E

Flow rates of oil phase and hydrogel-forming macromere

| | oil (μL/min) | | | | | | | |
|---|---|---|---|---|---|---|---|---|
| | 4 | 6 | 8 | 10 | 10 | 12 | 15 | 20 |
| macromer (μL/min) | 1 | 2 | 3 | 3 | 4 | 4 | 4 | 4 |

The residence time of cells in device was regulated by varying the outlet positions on the device, and the travel time of cells in device was calculated using the total flow rate of the fluid and geometry of the microfluidic device. Cellular response to different residence time with the nitrogen purging ($P_{N_2=7}$ psi) was evaluated as showed in FIG. 17B, in which the cell viability didn't change as the residence time increased from 2.4 s to 14.4 s. The experimental data showed that neither residence time nor the high nitrogen-purging pressure have a harmful effect on cells, which allows the precisely control of the oxygen concentration in fluids via nitrogen-purging pressure to achieve encapsulating cells in fully polymerized PEGDA-based microparticles in microfluidic device with a relatively high cell viability.

Cellular Response to the Nitrogen-Purging Pressure

Figure 18:
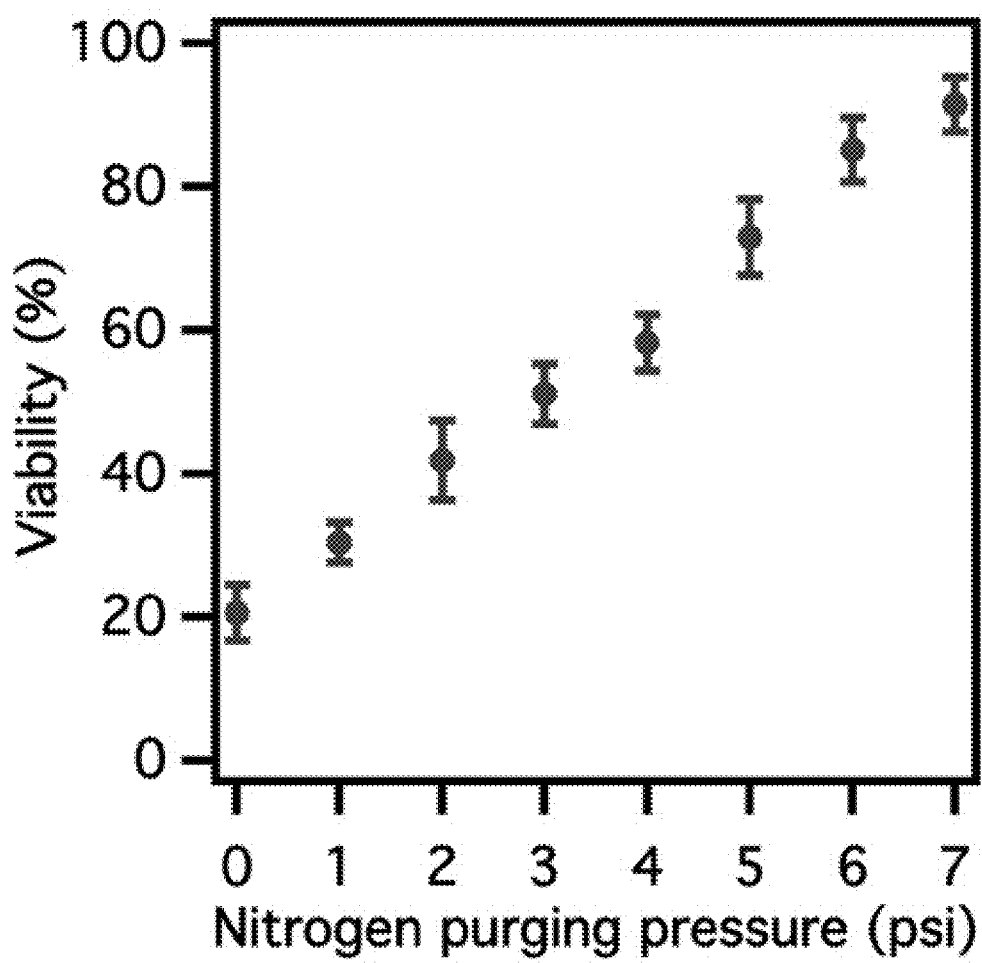
FIG. 18. demonstrates the effect of nitrogen purging pressure upon cell viability, where the microdroplets exposure to 120 mW/cm$^2$ UV light for 1.1 s.

Nitrogen purging microfluidic device has been successfully demonstrated to mitigate oxygen inhibition of free chain polymerization and be used to achieve fully polymerized microparticles in microfluidic using PEGDA via photopolymerization. Cellular response to nitrogen-purging pressure was evaluated by varying the nitrogen pressure from 0 to 7 psi, in which the flow rate of hydrogel-forming solution and oil phase was 1 μL/min, and 2 μL/min for the first layer and 7 μL/min for the second layer, respectively. Microdroplets with cells were exposed to 120 mW/cm$^2$ UV light for 1.1 s while traveling through UV exposure area on device. The experiment results illustrated that the cell viability was increased from 20% to 90% as the nitrogen purging pressure was varying from 0 to 7 psi (FIG. 18). As the cell viability has been shown directly related with the amount of peroxy radicals produced during the radical oxidation process, this results indicated that the nitrogen purging pressure related with the residue oxygen concentration in the fluids.

Cellular Response to UV Exposure Time and Intensity

Cells were encapsulated within microdroplets in device, which turned into microparticles via photopolymerization reaction while they were traveling through the UV exposure area. The recently proposed nitrogen-purging microfluidic device by our group enabled the cell encapsulation within fully polymerized PEGDA-based microparticles in device with an improved cell viability by significantly decreased the residue oxygen concentration in fluids; however, the effects of UV radiation upon cell viability have not been clearly illustrated. Here we decoupled the UV radiation into UV radiation time and intensity and mapped their effects upon cell viability, separately.

Figure 19:
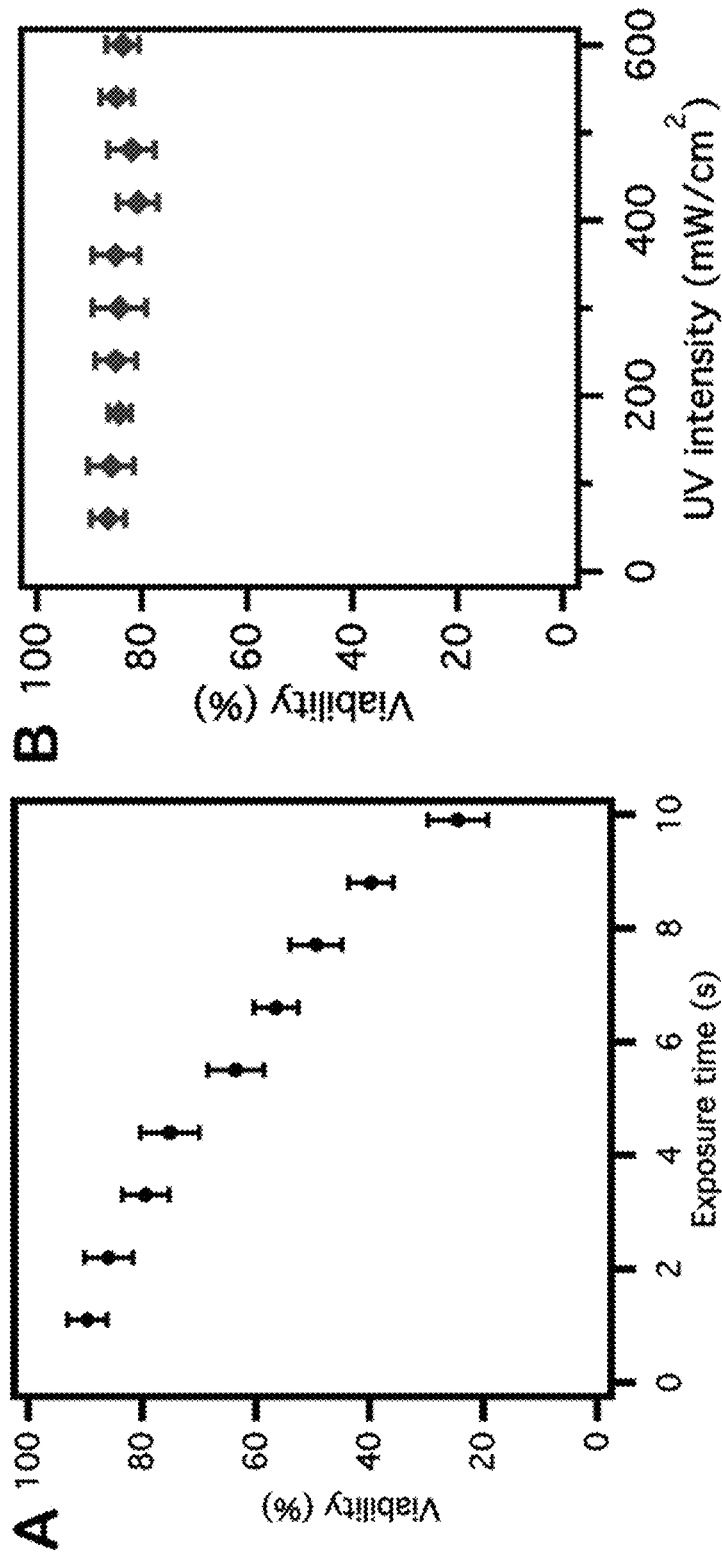
FIG. 19. provides (A) The effect of UV radiation time upon cell viability was mapped, in which the UV intensity was the same. (B) Effects if UV intensity upon cell viability with the same UV radiation time.
Figure 20:
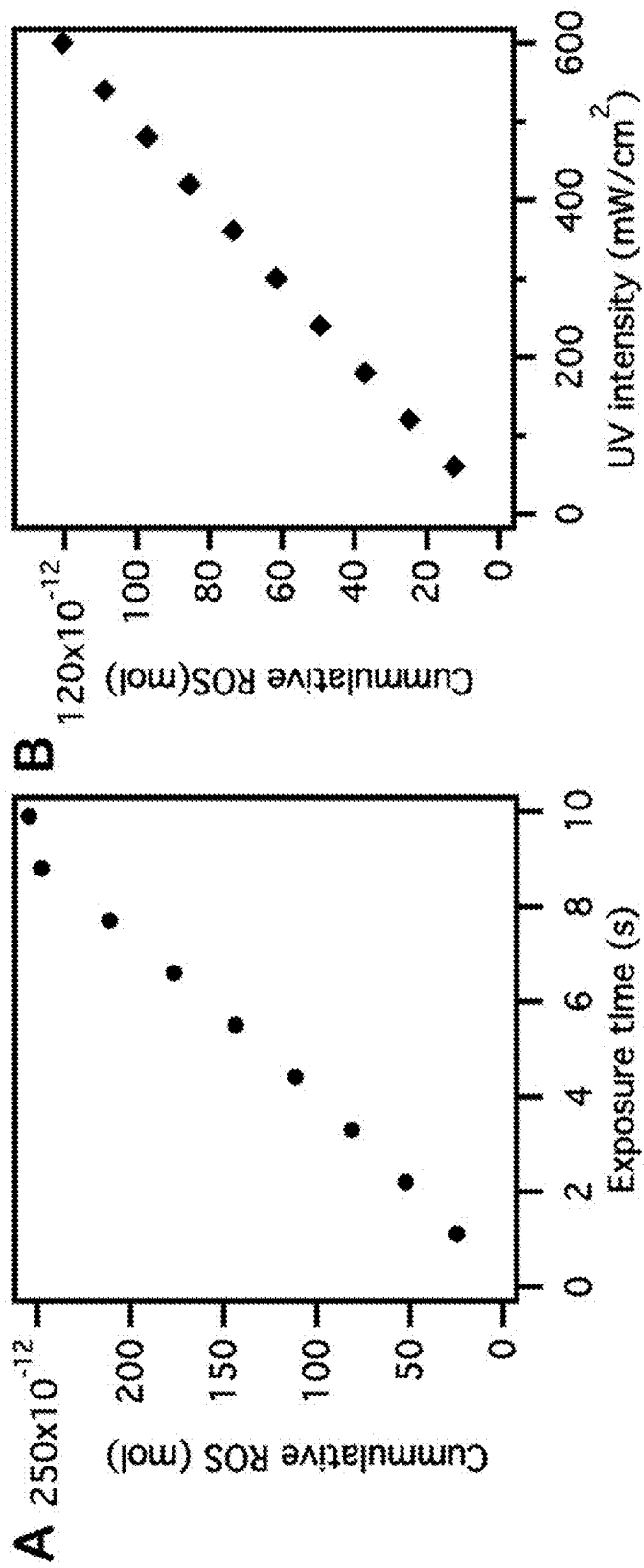
FIG. 20. illustrates (A) Cumulative concentration of peroxy radicals as a function of UV exposure time with a constant UV intensity. (B) Cumulative concentration of peroxy radicals as a function of UV intensity under the same UV exposure time.

A series of masks with specific transparent areas were designed and put on the top of microfluidic device to control the UV exposure time as it was showed in FIG. 16B. The effect of UV exposure time on cell viability was plotted in FIG. 19A, in which the cell viability dropped from 90% to 20% while the UV exposure time was increased from 1.1 s to 9.9 s. The results showed that the increasing of UV exposure time with a constant intensity has a harmful effect upon cells. And then the effect of UV intensity on cell viability was evaluated by varying the UV intensity while keeping the UV exposure time a constant, 1.1 s. The cells response to the changing of UV intensity was mapped as showed in FIG. 19B, in which cell viability didn't have an obvious change while the UV intensity was increased from 60 to 600 mW/cm$^2$. Those experimental results illustrated that the changing of UV intensity didn't have a strong effect on cell viability as the UV exposure time did. Compared the above experimental results, the cells viabilities have a huge difference (FIGS. 19A and 19B), which indicated the UV light exposure time and intensity may have a unequally contribution to the decrease of cells viability.

Calculation of the Cumulative Peroxy Radical Amount Using COMSOL

The UV radiation dosage was the same when the UV radiation time were 5.5 s and 1.1 s with the UV intensity were 120 and 600 mW/cm$^2$; the cell viabilities, however, were significantly different, and they were 60% and 85%, respectively. To further interpret why the effects of same UV radiation dosage were different upon cell viability, we calculated the cumulative peroxy radical amount formed during the UV exposure using the COMSOL model, which have been shown directly related to cell viability in our previous works. From the results obtained from the COMSOL model, even the UV radiation dosage was the same for the above two conditions, the cumulative peroxy radical amount were different, in which the one with shorter UV exposure time produced less peroxy radicals, and also led to a higher cell viability. The experimental results illustrated that with a certain UV radiation dosage, the longer UV exposure time have much more harmful effects on cells than higher intensity have.

Conclusions

In this example we have evaluated cellular response to individual factors involved in cell encapsulation in microfluidic device via photopolymerization of PEGDA. The residence time and relatively low flow rate wouldn't impart harmful effect upon cell, and a high cell viability can be obtained. The nitrogen-purging pressure, however, has a critical effect on cell viability, which should be at least higher than 5 psi in order to achieve a high postencapsulation cell viability. Cellular response to UV exposure illustrated that the UV exposure time and intensity have unequal contributions to the formation of peroxy radicals during the cell encapsulation, in which a short exposure time should be adopted instead of low UV intensity for a specific UV radiation dosage. Cellular response to those individual factors in terms of viability provides a standard for encapsulating cells within microparticles in microfluidic device via photopolymerization, in which a relative high nitrogen-purging pressure and shorter UV exposure time should be used under a relatively low flow rate to achieve a good postencapsualtion cell viability.

Supplementary Information

TABLE F

PEGDA polymerization reaction steps

| Steps # | Reaction | Description |
| --- | --- | --- |
| 1 | $I \xrightarrow{k_d} R^*$ | Initiator photolysis |
| 2 | $R^* + M \xrightarrow{k_i} M^*$ | Monomer activation |
| 3 | $M_n^* + M \xrightarrow{k_p} M_{n+1}^*$ | Chain propagation |
| 4 | $M_n^* + M_m^* \xrightarrow{k_t} M_{n+m}$ | Chain termination |
| 5 | $M_n^* + O_2 \xrightarrow{k_{O_2}} MOO$ | Oxygen inhibition |
| 6 | $M_n^* + O_2 \xrightarrow{k_{O_2}} MOO$ | Radical oxidation |

In the above table, M represents unconverted double bonds; M* represents the radical species; X represents all the radical species (M* and R*).

TABLE G

Parameters involved in modeling peroxy radicals amount prediction

| Parameter | Description | Value |
|---|---|---|
| r | radius of the droplets | 25 μm |
| $D_{O2}$ | oxygen diffusivity in the droplet | $1*10^{-10}$ m$^2$/s |
| $D_I$ | Photoinitiator diffusivity in the droplet | $1*10^{-18}$ m$^2$/s |
| $k_{O2}$ | Rate constant of the radical oxidation | $5*10^5$ m$^3$*mol$^{-1}$*s$^{-1}$ |
| $k_p$ | Rate constant of polymer propagation | 25 m$^3$*mol$^{-1}$*s$^{-1}$ |
| $k_t$ | Rate constant of radical termination | $2.5*10^3$ m$^3$*mol$^{-1}$*s$^{-1}$ |
| φ | Quantum yield of radical | 1.0 |
| λ | Wavelength | 365 nm |
| $N_A$ | Avogadro number | mol$^{-1}$ |
| h | Planck's constant | $6.63*10^{-34}$ m$^2$*kg$^{-1}$*s$^{-1}$ |
| C | Speed of light | $2.99*10^8$ m*s$^{-1}$ |
| ε | Molar absorptivity | $2.18*10^5$ cm$^2$*mol$^{-1}$ |
| $I_0$ | UV light intensity | 220 mW*cm$^{-2}$ |
| $MW_{PEGDA}$ | Molecular weight of PEGDA | $3.4*10^3$ g*mol$^{-1}$ |

Example 5: A Microfluidic-Based Cell Encapsulation Platform to Achieve High Long-Term Cell Viability in Photopolymerized PEGNB Hydrogel Microspheres Cell encapsulation within photoinitiated polyethylene glycol (PEG)-based hydrogel scaffolds has been demonstrated as a robust strategy for cell delivery, tissue engineering, regenerative medicine, and developing in vitro platforms to study cellular behavior and fate. Control over the spatial and temporal specificity of PEG hydrogel mechanical properties, chemical functionalization, and cytocompatibility has advanced considerably in recent years. Recent microfluidic technologies have enabled the miniaturization of PEG hydrogels, thus making fabrication of miniaturized cell-laden vehicles possible. However, the presence of oxygen dramatically inhibits the chain growth photopolymerization of polyethylene glycol diacrylate (PEGDA), thus limiting its application in microfluidics. Another promising PEG-based scaffold material, PEG norbornene (PEGNB), is formed by a step-growth photopolymerization, which is not inhibited by oxygen. PEGNB is also more cytocompatible than PEGDA and allows for orthogonal addition reactions. The step-growth kinetics, however, are slow and therefore present a challenge to achieve fully polymerized microgel droplets within microfluidic devices. Here, we describe a microfluidic-based droplet fabrication platform that generates consistently monodisperse cell-laden water-in-oil emulsions. PEGNB droplets are collected and photopolymerized under UV exposure in bulk. In this work, we compared this microfluidic-based cell encapsulation platform with a vortex-based method for microgel size, uniformity, post-encapsulation cell viability and long-term cell viability. Several factors that potentially influence post-encapsulation cell viability were identified. Finally, this platform was compared with a similar cell encapsulation platform using PEGDA in term of long-term cell viability. We show that this PEGNB microencapsulation platform is capable of generating cell-laden hydrogel microspheres at high rates with well-controlled size distributions and high long-term cell viability.

Introduction

Bulk hydrogels are widely used to encapsulate live cells for a variety of applications. In tissue engineering, encapsulating and organizing cells within a three-dimensional hydrogel scaffold can direct the formation of desired tissue through the presentation of specific signaling cues (REF 5.1-5.2). Recently, implantation of a cell-laden hydrogel scaffold has been developed as an alternative and appealing approach for controlled, sustainable growth factor delivery in vivo (REF 5.3), in which hydrogel scaffolds serve as a barrier to isolate implanted cells from the immune system, preventing immune-rejection (REF 5.4) while allowing bidirectional diffusion of oxygen, nutrients, and cell products and wastes (REF 5.5). Advances in hydrogel scaffold development has facilitated cell encapsulation a potential therapy for type 1 diabetes (REF 5.6), cartilage (REF 5.7) and bone regeneration (REF 5.8), osteroarthritis (REF 5.9), parkinsonian symptoms (REF 5.10) and cancer (REF 5.11). A variety of cell encapsulants have been investigated including agarose, alginate, collagen, and hyaluronic acid (REF 5.12-5.15). In recent years, PEG-based, free-radical photopolymerized hydrogels have been intensively studied and developed as a cell encapsulant due to their synthetic versatility and ability to spatially and temporally control hydrogel network properties (REF 5.16-5.18). Also, PEG hydrogels have displayed excellent cytocompatibility for many cell types including mesenchymal stem cells (MSCs), β cells, fibroblasts, and neural cells, making them an attractive scaffold material for cell encapsulation (REF 5.19-5.22).

Free-radical photopolymerization strategies generally include either acrylate or thiol-ene chemistries allowing chain-growth or step-growth gelation mechanisms, respectively (REF 5.23-5.25). Chain-growth polymerization (PEGDA), however, is almost completely inhibited by the presence of oxygen because the rate of radical quenching by oxygen is much faster than the rate of chain initiation and propagation (REF 5.26-5.28) Products of radical scavenging include an accumulation of reactive oxygen species (ROS), which can induce elevated intracellular oxidative stress in cells thus cause damage to biomacromolecules such as DNA, proteins, and lipids (REF 5.29-5.30). Conversely, step-growth polymerization of PEGNB, occurring between a thiol and vinyl group is not dramatically inhibited by oxygen. Upon photoinitiation, PEGNB can form a more homogenous polymer network with reduced shrinkage in structure thus induce less cellular stresses than PEGDA (REF 5.31). Perhaps most importantly, PEGNB has been shown to support increased post-encapsulation viability over PEGDA for certain cell types, suggesting its powerful utility as a cell encapsulant (REF 5.32). While the origins of PEGNB's increased cytocompatibility is uncertain, studies have shown that PEGNB polymerization can be propagated by, thereby consuming ROS (REF 5.33-5.34). For cell types that are especially sensitive to ROS, reducing these deleterious side products of photopolymerization may be a contributing factor to observed increasing cell viability.

Miniaturizing PEG hydrogels through microfabrication or microfluidics has emerged as a promising and versatile platform for biosensing, tissue engineering, drug delivery, and high throughput screening (REF 5.35-5.39). Cell encapsulation has been demonstrated by stop flow lithography (SFL), a single-phase microfluidic technique for PEG microgel fabrication, at low throughput but with precise control over microgel shape and size (REF 5.40). SFL combined with hydrolytically degradable hydrogel networks can produce a cell or drug delivery scaffold with tunable properties and degradation profiles (REF 5.41). Microfluidic emulsification, a two-phase microfluidic technique capable of generating monodisperse aqueous droplets in continuous oil phase has improved microgel fabrication frequency to kHz (REF 5.38), thus providing a potential tool for high throughput single cell encapsulation or screening (REF 5.42-5.44). Sustained cell viability following photoencapsulation is an important parameter to consider especially in applications that require growth factor secretion from encapsulated cells. However, even though high initial post-encapsulation cell viability can be achieved after encapsulating cells within PEGDA hydrogel microspheres (REF 5.28, 5.45), a dramatic decrease in cell viability is observed over longer time periods.

In this example, we utilize a cross-flow microfluidic device to encapsulate cells within PEGNB droplets, which are then collected and exposed to UV light in bulk solution for photopolymerization. Utilizing this platform, we have been able to exploit the benefits of microfluidics by producing uniform cell-laden hydrogel microspheres at high rates. By polymerizing in bulk, we overcome the slow polymerization kinetics of PEGNB, and achieve high post-encapsulation cell viability for a much longer period of time. Hydrogel microsphere uniformity and post-encapsulation cell viability has been compared between this platform and vortex-based cell encapsulation. Several factors that might have an impact on cell viability have been investigated with the goal of increasing post-encapsulation cell viability. In comparison with PEGDA, we have shown this microfluidic-based cell encapsulation platform is able to produce cell-laden PEGNB hydrogel microspheres with dramatically increased post-encapsulation cell viability.

Materials and Methods
Initiator and Macromer Synthesis

Synthesis of the photoinitiator lithium acylposphinate salt (LAP) was conducted according to an established protocol (REF 5.46). Briefly, 2,4,6-trimethylbenzoyl chloride was added dropwise to a 100 mL round bottom flask containing an equimolar quantity of dimethyl phenylphosphonite (both from Sigma-Aldrich). The flask was continuously purged with nitrogen gas and stirred at room temperature overnight. A solution containing a four-fold (mol:mol) excess of LiBr dissolved in 80 mL 2-butanone (both from Sigma-Aldrich) was added to the Michaelis-Arbozov product from previous step, stirred, and heated to 50° C. until the formation of a precipitate was observed (10 minutes). The flask was then cooled to room temperature and allowed to stir for 4 hours. Product was dried under vacuum and rinsed with aliquots of 2-butanone to remove unreacted LiBr. The product LAP was recovered with a yield of >80%, and confirmed via H-NMR.

Synthesis of the macromer 4-arm poly(ethylene glycol) tetranorbornene (PEGNB) was conducting according to established protocols (REF 5.24, 5.32, 5.47). Briefly, 12 grams of 20 kDa 4-arm PEG (Creative PEGworks) was added to 20 mL of methylene chloride (MeCl, Sigma Aldrich) in a 40 mL scintillation flask, stirred until complete dissolution was achieved, and set aside. To a 50 mL rb-flask containing 10 mL MeCl was added N,N-dicyclohexyldiimide followed by the dropwise addition of 5-norbornene-2-carboxylic acid (5 and 10 molar excess to 4-arm PEG, respectively; both from Sigma Aldrich). The previously prepared 4-arm PEG solution was added to the 50 mL rb-flask, placed in an icebath, and allowed to stir overnight under nitrogen. Ice cold diethyl ether (Sigma Aldrich) was added to the product-containing solution and the resultant precipitate was vacuum-filtered, recrystallized, and then subjected to soxhlet extraction for 36 hours to remove undesired impurities. The white PEGNB product was dried overnight under vacuum. The product was recovered with 67% yield, and confirmed via H-NMR.

Microfluidic Device Fabrication

Microfluidic cross-flow devices were fabricated using standard PDMS soft lithography techniques (REF 5.48). Briefly, polydimethylsiloxane (PDMS) was poured onto an SU-8 micropatterned silicon wafer, vacuumed to remove entrapped air, and cured in a 70° C. oven for at least 1 hour. PDMS replicas were cut and punched with a 20 G needle (Brico Medical Supplies, Inc., USA) to form inlets and outlets. PDMS chips were treated with oxygen plasma and bonded to glass slide. To facilitate droplet formation, a hydrophobic microchannel surface was created by filling the device with Aquapel (PPG Industries) and flushing with air. For PEGNB droplet formation, channel dimensions (h×w) were 80 µm×100 µm for the cell-containing aqueous phase and 80 µm×30 µm for the oil phase. Double layer nitrogen-jacketed microfluidic devices for PEGDA particle production were fabricated as previously described (REF 5.45).

Pre-Polymer Solution

PEGNB pre-polymer solutions were mixed to a final concentration of 10 wt % PEGNB ($M_n \approx 20000$ Da with 4 arms), 10 mM di-thiol linker ($M_n \approx 1500$ Da, Sigma-Aldrich, USA), 0.1 wt % lithium phenyl-2,4,6-trimethylbenzoylphosphinate (LAP, photoinitiator). PEGDA pre-polymer solutions were mixed to a final concentration of 10 wt % PEGDA ($M_n \approx 2400$ Da, JenKem Technology, USA), 0.1 wt % LAP, and 5 mM RGDS.

Cell Culture

Human lung adenocarcinoma epithelial cells (A549s) were cultured in Dulbecco's modified Eagle's medium (DMEM; Life Technology, USA) with low glucose, and supplemented with 10% fetal bovine serum (FBS, Life Technology, USA), 1% PenStrep, and 0.2% Fungizone (Sigma-Aldrich, USA). A549 s were cultured in a 37° C., 5% $CO_2$ incubator, with medium change every 3 days and subculture every 6 days. In preparation for cell encapsulation, A549 s were detached from culture flask with 0.05% trypsin (Life Technology, USA), pelleted, and resuspended to a cell density of $5 \times 10^7$ cells/mL in culture medium. Medium density was adjusted to 1.06 g/mL by adding in 18.75% v/v Opti Prep (Sigma-Aldrich, USA).

Microfluidic Cell Encapsulation

Figure 21:
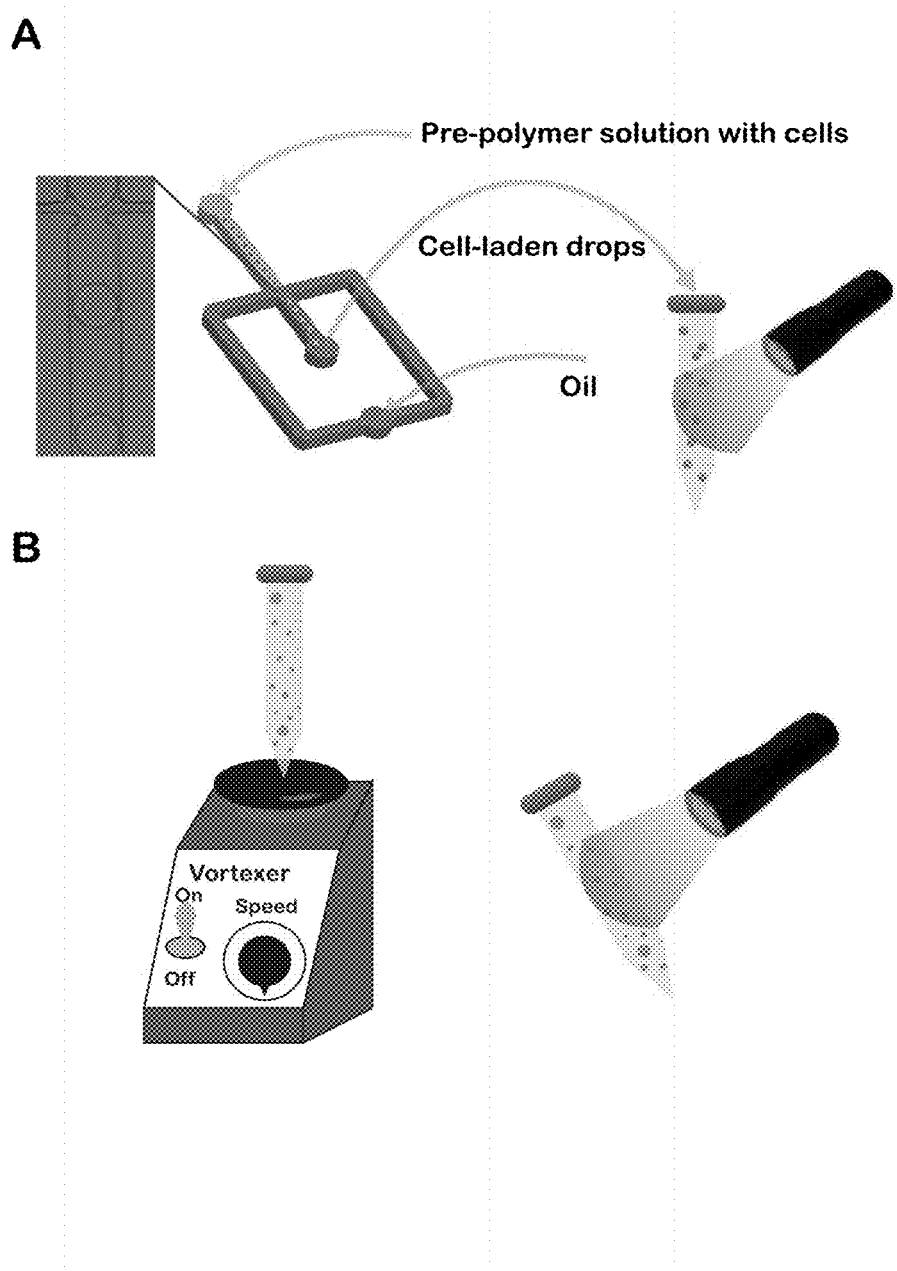
FIG. 21. provides a schematic of PEGNB hydrogel microsphere formation made by emulsification in a cross-flow microfluidic channel (A) or by vortexing (B), followed by exposure to ultraviolet radiation.

Prior to cell encapsulation in PEGNB (FIG. 21A), A549 s were suspended in pre-polymer solution, mixed, and injected into the microfluidic device via syrine pump. Flow rates for fluorocarbon oil (Novec 7500 with 2 wt % Pico-Surf (Dolomite) as surfactant) and aqueous phase were held constant at 10 µL/min and 2 µL/min, respectively. Cell-laden droplets were collected, and polymerized into hydrogel microspheres in bulk by exposing to UV light for 20 seconds (100 mW/cm², Lumen Dynamics Group Inc., 52000-XLA, Canada). Hydrogel microspheres were separated from oil by washing and centrifuging on a 10 µm strainer (PluriSelect, Germany) with 0.1 wt % Pluronic F-68 (Sigma-Aldrich, USA) in PBS. Cell-laden hydrogel microspheres were resuspended into culture medium containing 0.1 wt % F-68 in low-attachment 6-well plates (Corning Incorporated, USA) (REF 5.28).

For PEGDA encapsulation (FIG. 25C), A549s, PEGDA, and LAP with RGDS were loaded into three syringes and mixed within microfluidic device with a constant flow rate of 0.33 µL/min. Fluorocarbon oil was injected into microfluidic device at 2 µL/min and 7 µL/min for the first layer and second layer, respectively. Nitrogen pressure in the jacketing was held at a constant pressure of 7 psi. Before exiting the device, droplets passed through a serpentine channel in the second layer of the device where they were polymerized by exposure to UV light (Mecury-100W, Chiu Technical Corporation, USA) through a 20× microscope objective (Olympus). Cell-laden PEGDA hydrogel microspheres were separated from oil and cultured as described above.

Vortex Cell Encapsulation

A549 s and PEGNB pre-polymer solution were mixed by vortex for 30 s on a vortexer (~1000 osc/min) (Scientific Industries Inc., USA). Fluorocarbon oil was then added to the pre-polymer solution and vortexed for 1 min to form emulsions, which were polymerized into hydrogel microspheres by exposure to UV light for 20 seconds (FIG. 1B). Hydrogel microspheres were separated and cultured using the same approach as described above.

Bulk Cell Encapsulation

A549 s were mixed within PEGNB or PEGDA pre-polymer solution and exposed to UV light for 20 seconds to form cell-laden hydrogel constructs. Cells encapsulated within bulk hydrogels were cultured in culture medium, which was changed every other day. The approximate volume of each construct was 60 µL and the density of cells within construct was held constant at ~$5 \times 10^7$ cells/mL.

Cell Viability Measurement

Viability of encapsulated cells was measured using a membrane integrity assay (LIVE/DEAD Viability kit, Life Technologies, USA) that stains live cells green and dead cells red. Cell viability was imaged using an inverted fluorescence microscope (IX-71, Olympus, USA) and calculated.

Results and Discussion

Figure 22:
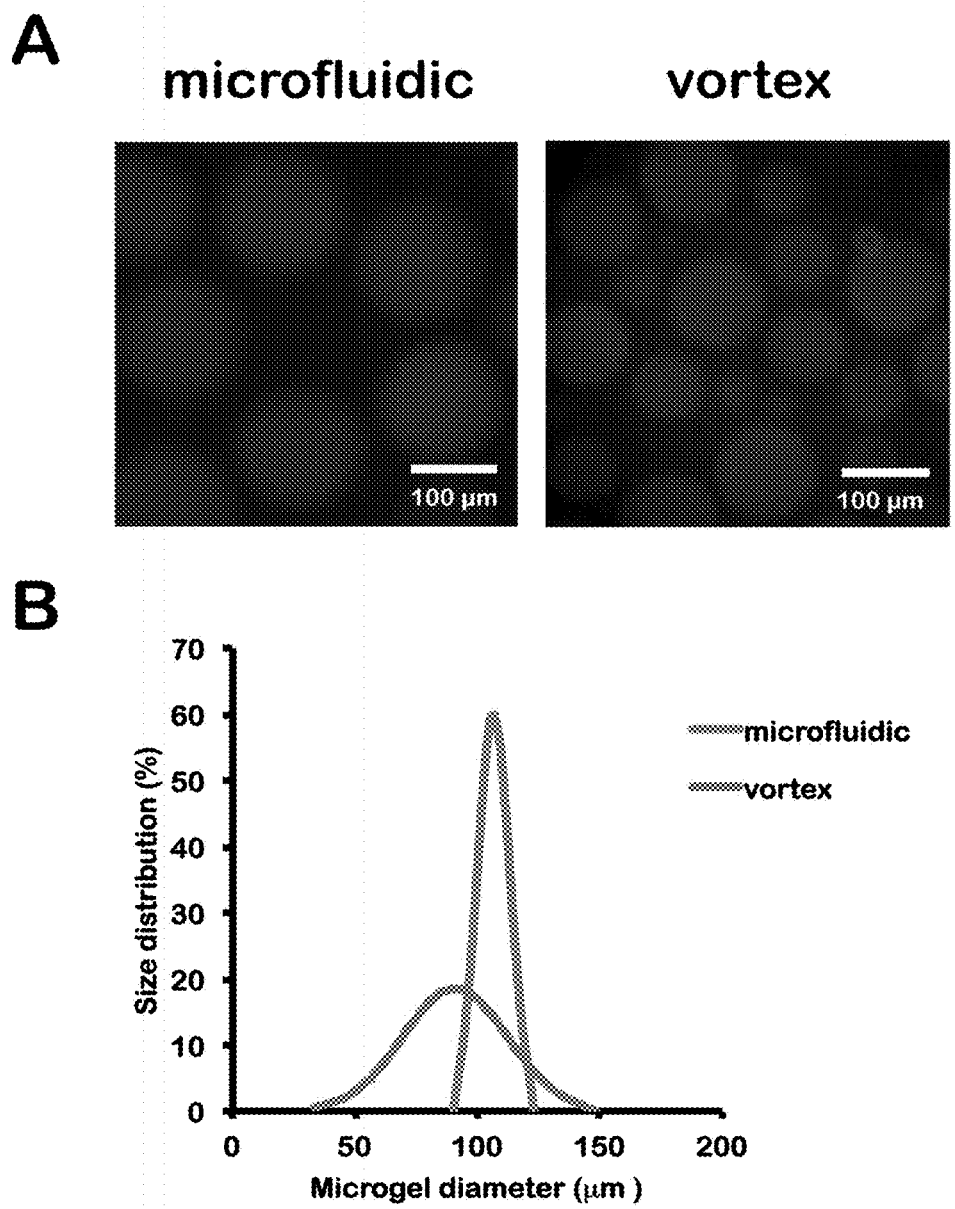
FIG. 22 demonstrates Size distributions and images of PEGNB hydrogel microspheres made by emulsification in cross-flow microfluidic devices (A) or by vortex (B).

Size Distribution of Hydrogel Microspheres Made by Microfluidic Device and Vortex Hydrogel microsphere size characterization was performed by two approaches. First a red dye, 0.01 wt % thiolated Rhodamine B was added into pre-polymer solution to label the network. Hydrogel microspheres were imaged using fluorescence microscopy and their diameters were measured using ImageJ. Fluorescence images of hydrogel microspheres and size normal distributions are shown in FIG. 22. As expected, hydrogel microspheres produced by microfluidic devices have a diameter range from 90 to 130 µm, exhibiting a much tighter size distribution than those produced by vortex with a diameter range from 30 to 140 µm. The polydispersity of microgel particles was calculated as the standard deviation of the diameter of particles divided by the mean diameter for both microfluidic and vortex fabrication methods. Microfluidics generated microgels with a 6.22% polydispersity while vortexing produced particle samples with an average polydispersity of 23.62%, indicating microfluidics had greatly improved the monodispersity of microgels.

Cell Microencapsulation and Effect on Cell Viability

A549 s were encapsulated and photopolymerized within PEGNB hydrogel microspheres through two approaches described above (FIG. 23B). These cell-laden particles were collected and cultured separately in a 37° C., 5% $CO_2$ incubator with medium change every other day. Cell viability assays were conducted in the course of 30 days by staining cell-laden particles with 2 µM calcein AM and 4 µM ethidium homodimer-1. Cells encapsulated by vortexing and within microfluidic devices shared similar trends in viability. High cell viability (>90%) was observed immediately after encapsulation into hydrogel microspheres, followed by gradually decreased cell viability over time while maintaining at a relative high level (FIG. 23A). Notably, blank PEGNB hydrogel particles were fabricated without any modification to facilitate cell attachment or proliferation in this work. However, as previous work has indicated, protein or peptide modifications to the hydrogel network improve cell attachment or hydrogel degradation (REF 5.49-5.50). Similar network modifications may be explored as a route to further increasing long-term post-encapsulation viability of cells encapsulated within PEGNB particles.

Figure 23:
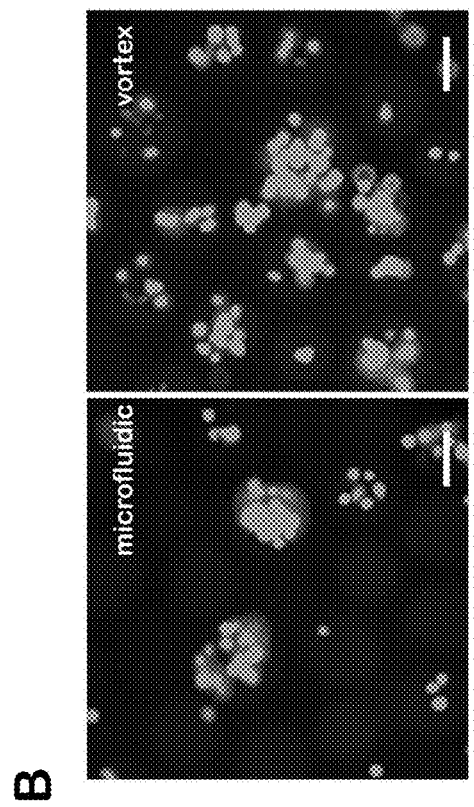
FIG. 23 illustrates the (A) Viability of A549 cells encapsulated within PEGNB microparticles by either vortex or microfluidic emulsification. Cell residence time in the hydrogel-forming solutions were 1 minute and 10 minutes for the vortex and microfluidic methods, respectively. (B) Images of cell-laden hydrogel microspheres made by each method (scale bar=100 µm). Viability of cells is indicated by live/dead staining assay (live and dead correspond to green and red, respectively).
Figure 23:
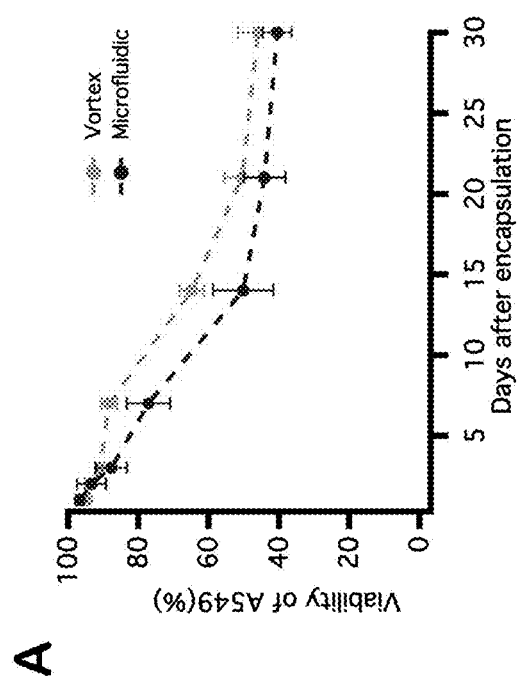
Figure 24:
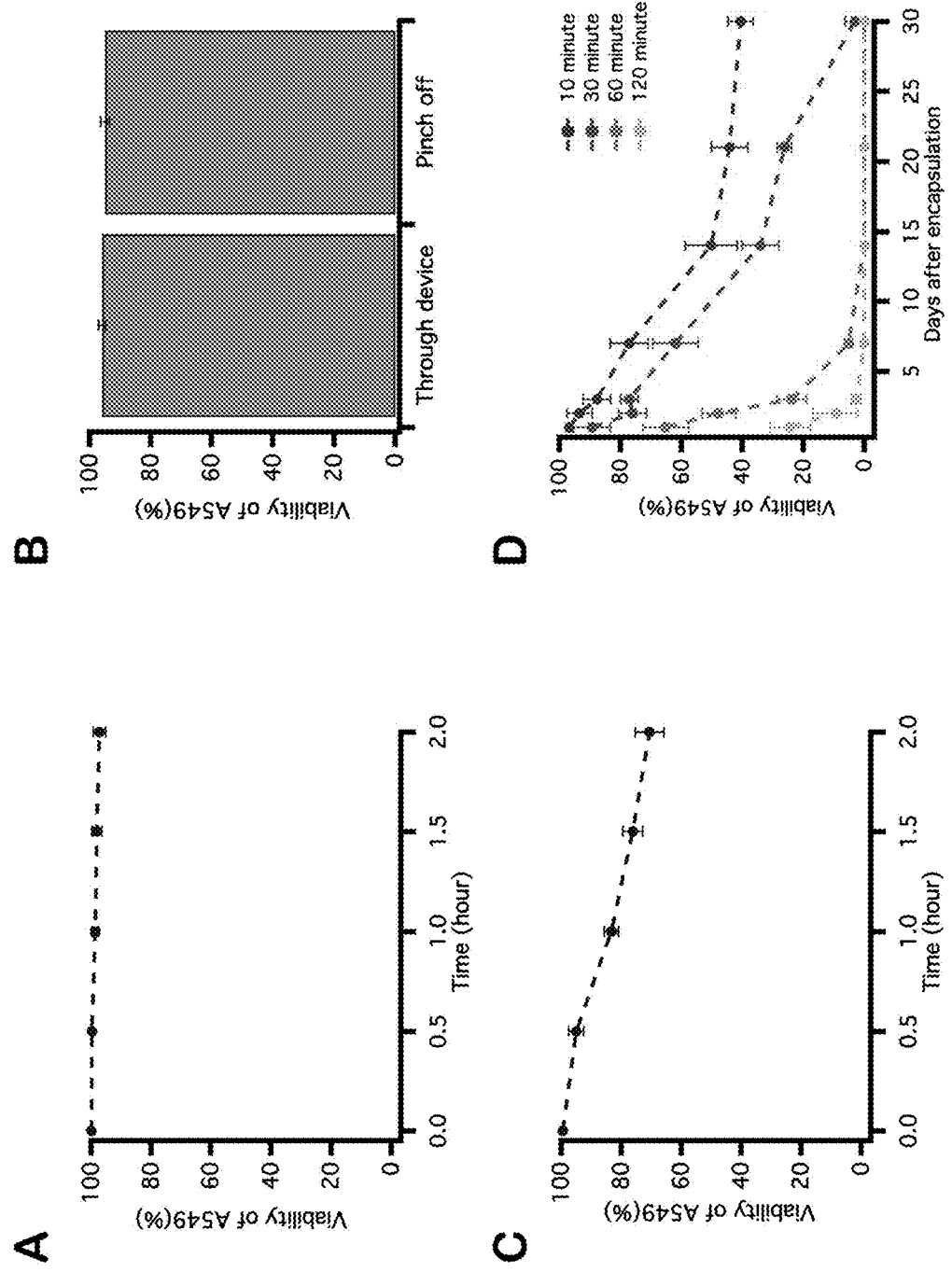
FIG. 24. illustrates factors affecting post-encapsulation cell viability were investigated. (A) Viability of cells maintained in media within a syringe over time. (B) Viability of cells pumped through a device in culture medium with or without being formed into emulsion droplets. Flow rates for cells and oil were 2 µL/min and 10 µL/min, respectively. (C) Viability of cells maintained within hydrogel-forming solution within a syringe over time. (D) Viability of cells encapsulated into PEGNB microspheres via microfluidic emulsification, collected in a vial, and exposed to UV light following specific incubation periods. Viability was measured for 30 days.

Effect of Factors Involved in Microfluidic Cell Encapsulation on Post-Encapsulation Cell Viability To identify parameters during microfluidic cell encapsulation that associate with cell damage, and loss of viability, a series of control experiments were performed using cell viability as the primary metric. To replicate the logistics of encapsulation, A549 s were transferred in culture medium to a syringe, where they were maintained at room temperature for 2 hours, with cell viability assayed every 0.5 hour. Little decrease in cell viability was observed over the course of 2 hours (FIG. 24A), indicating that long residence times in a syringe prior to delivery to the device is not deleterious to cells. To explore whether aspects of microfluidic encapsulation of cell into droplets affected cell viability, A549 in medium were injected into a microchannel and were either passed through or were pinched off into droplets by an oil phase. In the latter case, flow rates for aqueous and oil phase were 2 µL/min and 10 µL/min. Emulsions were broken by centrifugation using a 5 µm cell strainer. Cell viability was reduced by only about 4% as a result of traveling through the microfluidic device, and by an additional 5% by virtue of being pinched off by oil and encapsulated into droplets (FIG. 24B). A549 s were next mixed into the PEGNB pre-polymer solution and maintained at room temperature without any UV exposure over a period of 2 hours. A notable decrease in cell viability was observed by staining these cells every 30 minutes (FIG. 24C), indicating that merely incubating cells in the PEG hydrogel-forming solution for extended periods of time represents a process that reduces cell viability. The effect of the elapsed time between cell encapsulation and hydrogel photopolymerization on post-encapsulation cell viability was also investigated. Cell-laden PEGNB droplets were collected for discrete durations, and then polymerized by exposure to UV light. Cells suffered a significant decrease in viability with increasing collection time (FIG. 24D). The time-dependent decrease in cell viability observed as a result of cell residence within hydrogel forming solutions may explain the slight increase in cell viability following encapsulation by vortexing over microfluidics (FIG. 23). Vortexing, like the polymerization of bulk hydrogel constructs, is an inherently batch process, which required only about two minutes between emulsion generation and the collection of polymerized cell-laden particles. Microfluidic encapsulation, on the other hand, is a continuous process that may require extended incubation within unpolymerized hydrogel forming solutions. As noted, this residence time, while unexplained, is deleterious to cells.

Comparison Between PEGNB and PEGDA Post-Encapsulation Cell Viability

Figure 25:
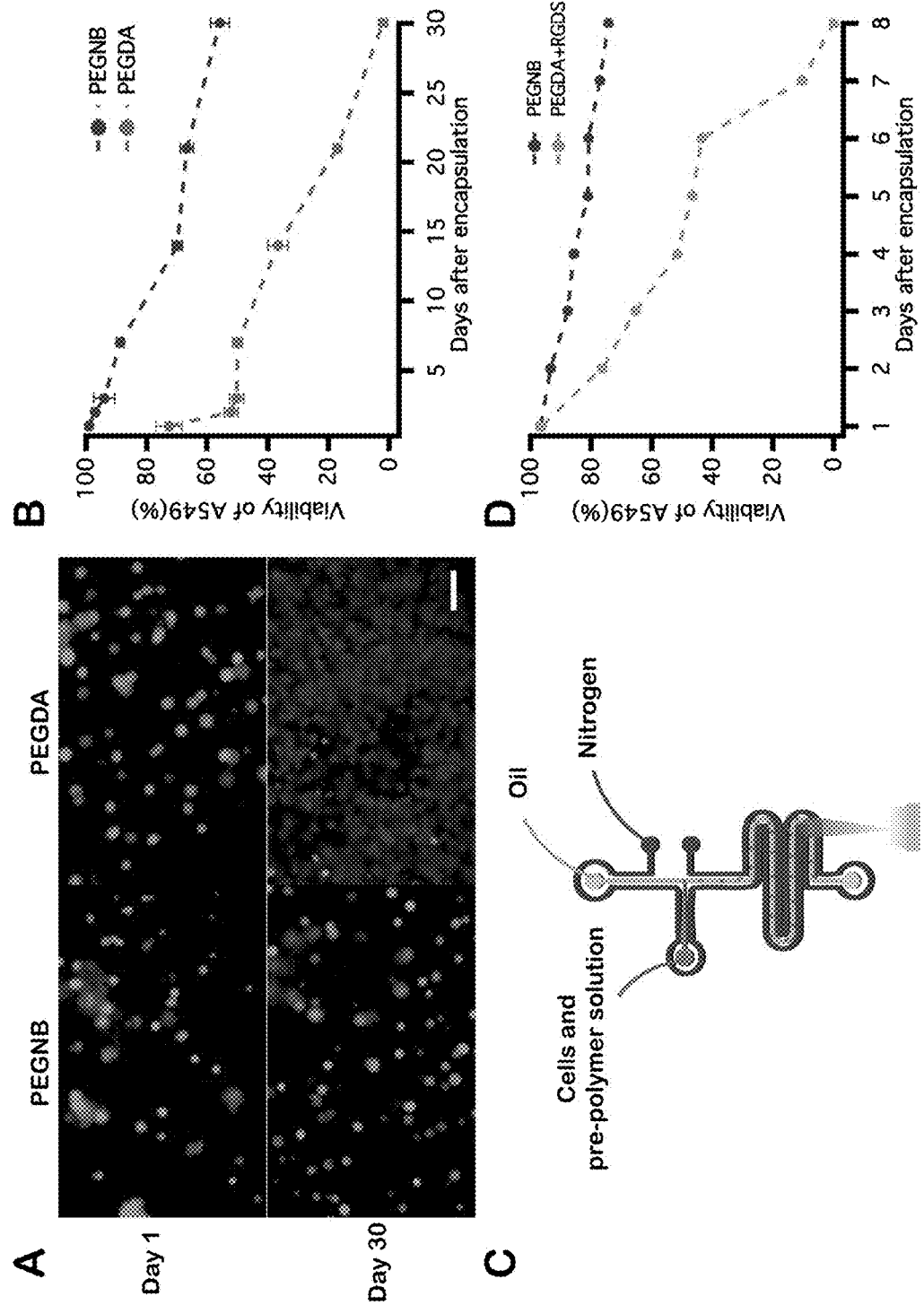
FIG. 25. provides a comparison between observed viability for cells encapsulated within PEGNB and PEGDA microspheres via microfluidic emulsification. (A) Images of cells encapsulated into 10 wt % PEGNB and PEGDA bulk hydrogels. Cells were mixed with PEG hydrogel-forming solution followed by exposure to UV light to polymerize the cell-laden bulk structure. (B) Cell viability was quantified for 30 days following encapsulation in bulk hydrogels. (C) Schematic illustration of the nitrogen jacketed microfluidic device used for cell encapsulation into PEGDA hydrogel microspheres. (D) Quantification of post-encapsulation viability of cells within PEGNB and RGDS-modified PEGDA hydrogel microspheres. Scale bar=100 µm.

PEGDA has been widely proven as a viable material for cell encapsulation, and has recently been shown to support high cell viability immediately following encapsulation and photopolymerization in microdroplets (REF 5.45). To evaluate the biocompatibility of PEGNB as a cell encapsulant relative to PEGDA under different encapsulation conditions, A549 s were encapsulated into PEGNB or PEGDA bulk hydrogels and hydrogel microspheres. Following bulk encapsulation, cells in PEGNB hydrogels maintained a higher viability than those in PEGDA hydrogel (FIGS. 25A and 25B), which is in agreement with previously reported results (REF 5.32, 5.51). For continuous cell microencapsulation, the high oxygen permeability of PDMS microfluidic devices, combined with the high oxygen solubility of the fluorocarbon oil used in these studies necessitates the use of a custom microfluidic design (REF 5.28, 5.52-5.53). This device, a nitrogen-jacketed double layer device (FIG. 25C) was introduced to circumvent oxygen inhibition of PEGDA (REF 5.45) by eliminating oxygen diffusion to the droplet from the PDMS device or oil. Immediately after encapsulation, high cell viability was achieved in both blank PEGNB and RGDS-modified PEGDA hydrogel microspheres. After incubating for 8 days, however, high cell viability was sustained in PEGNB particles while cell viability decreased dramatically to 0% on day 8 in PEGDA particles (FIG. 25D). These results reflect trends observed in bulk hydrogels and further suggest that PEGNB is an inherently more cytocompatible cell encapsulant than PEGDA and supports enhanced sustained cell survival.

Conclusions

In this example, we have introduced a microfluidic-based cell encapsulation platform that allows PEGNB to be employed as the cell encapsulant. This approach was compared with and found to be superior to vortex-based cell encapsulation in terms of controlling hydrogel microsphere size and uniformity. We have shown that highly monodisperse, uniform cell-laden microgels with average diameters of approximately 110 μm can be generated consistently at high rates. Post-encapsulation cell viability, which is regarded as a primary parameter in this study, can be maintained at a relatively high level in the course of 30 days. Several experimental parameters have been investigated in order to tune cell viability after microencapsulation. Notably, a correlation was identified between post-encapsulation cell viability and droplet collection time, indicating cell viability decreases in a time-dependent manner until photopolymerization is conducted. Finally, the cytocompatibility of PEGNB was compared with PEGDA under bulk and microparticle cell encapsulation conditions. Cells encapsulated within PEGNB were found to exhibit excellent long-term survival, far outperforming PEGDA-encapsulated cells despite equivalent viabilities immediately following encapsulation. The microfluidic approach demonstrated here will enable PEGNB to be formed into microparticles that display the same relative advantages over PEGDA that have been observed in bulk hydrogels

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

REFERENCES 1.1. Mark, H. F. Encyclopedia of Polymer Science and Technology, Concise. (Wiley, 2013).
1.2. Saunders, K. J. in Organic Polymer Chemistry 125-148 (Springer Netherlands, 1988). doi:10.1007/978-94-009-1195-6_6
1.3. Burkoth, A. K. & Anseth, K. S. A review of photocrosslinked polyanhydrides: in situ forming degradable networks. Biomaterials 21, 2395-2404 (2000).
1.4. Metters, A. T., Bowman, C. N. & Anseth, K. S. A Statistical Kinetic Model for the Bulk Degradation of PLA-b-PEG-b-PLA Hydrogel Networks. J. Phys. Chem. B 104, 7043-7049 (2000).
1.5. Yu, Q., Nauman, S., Santerre, J. P. & Zhu, S. Photopolymerization behavior of di(meth)acrylate oligomers. Journal of Materials Science 36, 3599-3605 (2001).
1.6. Sawhney, A. S., Pathak, C. P. & Hubbell, J. A. Bioerodible hydrogels based on photopolymerized poly (ethylene glycol)-co-poly (.alpha.-hydroxy acid) diacrylate macromers. Macromolecules 26, 581-587 (1993).
1.7. Nguyen, K. T. & West, J. L. Photopolymerizable hydrogels for tissue engineering applications. Biomaterials 23, 4307-4314 (2002).
1.8. Mequanint, A. P. A. K. Hydrogel Biomaterials. 1-22 (2011).
1.9. Billiet, T., Vandenhaute, M., Schelfhout, J., Van Vlierberghe, S. & Dubruel, P. A review of trends and limitations in hydrogel-rapid prototyping for tissue engineering. Biomaterials 1-22 (2012). doi:10.1016/j.biomaterials.2012.04.050
1.10. Decker, C. & Jenkins, A. Kinetic approach of oxygen inhibition in ultraviolet- and laser-induced polymerizations. Macromolecules 18, 1241-1244 (1985).
1.11. O'Brien, A. K. & Bowman, C. N. Modeling the Effect of Oxygen on Photopolymerization Kinetics. Macromol. Theory Simul. 15, 176-182 (2006).
1.12. Ligon, S. C., Husár, B., Wutzel, H., Holman, R. & Liska, R. Strategies to Reduce Oxygen Inhibition in Photoinduced Polymerization. Chem. Rev. 114, 557-589 (2014).
1.13. Bryant, S. J., Nuttelman, C. R. & Anseth, K. S. Cytocompatibility of UV and visible light photoinitiating systems on cultured NIH/3T3 fibroblasts in vitro. Journal of Biomaterials Science, Polymer Edition 11, 439-457 (2000).
1.14. Rice, M. A. & Anseth, K. S. Encapsulating chondrocytes in copolymer gels: Bimodal degradation kinetics influence cell phenotype and extracellular matrix development. J. Biomed. Mater. Res. 70A, 560-568 (2004).
1.15. Mann, B. K., Gobin, A. S., Tsai, A. T., Schmedlen, R. H. & West, J. L. Smooth muscle cell growth in photopolymerized hydrogels with cell adhesive and proteolytically degradable domains: synthetic ECM analogs for tissue engineering. Biomaterials 22, 3045-3051 (2001).
1.16. Ford, M. C. A macroporous hydrogel for the coculture of neural progenitor and endothelial cells to form functional vascular networks in vivo. Proceedings of the National Academy of Sciences 103, 2512-2517 (2006).
1.17. Burdick, J. A. & Anseth, K. S. Photoencapsulation of osteoblasts in injectable RGD-modified PEG hydrogels for bone tissue engineering. Biomaterials 23, 4315-4323 (2002).
1.18. Mooney, R. et al. Control of Neural Cell Composition in Poly(Ethylene Glycol) Hydrogel Culture with Soluble Factors. Tissue Engineering Part A 17, 2805-2815 (2011).
1.19. Nicodemus, G. D. & Bryant, S. J. Cell encapsulation in biodegradable hydrogels for tissue engineering applications. Tissue Engineering Part B: Reviews 14, 149-165 (2008).
1.20. Zhu, J. Bioactive modification of poly(ethylene glycol) hydrogels for tissue engineering. Biomaterials 31, 4639-4656 (2010).
1.21. Kloxin, A. M., Kasko, A. M., Salinas, C. N. & Anseth, K. S. Photodegradable Hydrogels for Dynamic Tuning of Physical and Chemical Properties. Science 324, 59-63 (2009).
1.22. Pregibon, D., Toner, M. & Doyle, P. Multifunctional encoded particles for high-throughput biomolecule analysis. Science 315, 1393 (2007).
1.23. Panda, P. et al. Stop-flow lithography to generate cell-laden microgel particles. Lab Chip 8, 1056 (2008).
1.24. Dendukuri, D., Gu, S. S., Pregibon, D. C., Hatton, T. A. & Doyle, P. S. Stop-flow lithography in a microfluidic device. Lab Chip 7, 818 (2007).

1.25. Suh, S. K., Bong, K. W., Hatton, T. A. & Doyle, P. S. Using Stop-Flow Lithography To Produce Opaque Microparticles: Synthesis and Modeling. Langmuir 27, 13813-13819 (2011).

1.26. Appleyard, D. C., Chapin, S. C., Srinivas, R. L. & Doyle, P. S. Bar-coded hydrogel microparticles for protein detection: synthesis, assay and scanning. Nature Protocols 6, 1761-1774 (2011).

1.27. Lewis, C. L. et al. Microfluidic Fabrication of Hydrogel Microparticles Containing Functionalized Viral Nanotemplates. Langmuir 26, 13436-13441 (2010).

1.28. Hwang, D. K. et al. Stop-Flow Lithography for the Production of Shape-Evolving Degradable Microgel Particles. J. Am. Chem. Soc 131, 4499-4504 (2009).

1.29. Landfester, K. & Musyanovych, A. in Chemical Design of Responsive Microgels 234, 39-63 (Springer Berlin Heidelberg, 2010).

1.30. Ahmed, E. M. Hydrogel: Preparation, characterization, and applications: A review. Journal of Advanced Research 6, 105-121

1.31. Sivadas, N. & Cryan, S.-A. Inhalable, bioresponsive microparticles for targeted drug delivery in the lungs. Journal of Pharmacy and Pharmacology 63, 369-375 (2011).

1.32. Oliveira, M. B. & Mano, J. F. Polymer-based microparticles in tissue engineering and regenerative medicine. Biotechnol Progress 27, 897-912 (2011).

1.33. Hazel, J. et al. Changes in cytoplasmic volume are sufficient to drive spindle scaling. Science 342, 853-856 (2013).

1.34. Liu Tsang, V. & Bhatia, S. N. Three-dimensional tissue fabrication. Advanced Drug Delivery Reviews 56, 1635-1647 (2004).

1.35. Olabisi, R. M. et al. Hydrogel Microsphere Encapsulation of a Cell-Based Gene Therapy System Increases Cell Survival of Injected Cells, Transgene Expression, and Bone Volume in a Model of Heterotopic Ossification. Tissue Engineering Part A 16, 3727-3736 (2010).

1.36. De Geest, B. G., Urbanski, J. P., Thorsen, T., Demeester, J. & De Smedt, S. C. Synthesis of Monodisperse Biodegradable Microgels in Microfluidic Devices. Langmuir 21, 10275-10279 (2005).

1.37. Hwang, C. M. et al. Benchtop fabrication of PDMS microstructures by an unconventional photolithographic method. Biofabrication 2, 045001-045001 (2010).

1.38. Kuck, L. & Taylor, A. Photopolymerization as an innovative detection technique for low-density microarrays. Biotech. 45, 179-186 (2008).

1.39. Hamilton, S. K. et al. Development of 3-D Hydrogel Culture Systems With On-Demand Cell Separation. Biotechnology journal 8, 485-495 (2013).

1.40. Nair, J. R. et al. UV-Induced Radical Photo-Polymerization: A Smart Tool for Preparing Polymer Electrolyte Membranes for Energy Storage Devices. Membranes 2, 687-704 (2012).

1.41. Whitesides, G. Soft lithography. Annual review of materials science (1998).

1.42. Duffy, D., Schueller, O., Brittain, S. & Whitesides, G. Rapid prototyping of microfluidic switches in poly (dimethyl siloxane) and their actuation by electro-osmotic flow. Journal of Micromechanics and Microengineering 9, 211 (1999).

1.43. An, H. Z., Safai, E. R., Burak Eral, H. & Doyle, P. S. Synthesis of biomimetic oxygen-carrying compartmentalized microparticles using flow lithography. Lab Chip 13, 4765-4774 (2013).

1.44. Cox, M. E. & Dunn, B. Oxygen diffusion in poly (dimethyl siloxane) using fluorescence quenching. I. Measurement technique and analysis. Journal of Polymer Science Part A: Polymer Chemistry 24, 621-636 (1986).

1.45. Vermuë, M., Tacken, M. & Tramper, J. Tetralin and oxygen transfer in the liquid-impelled loop reactor. Bioprocess Engineering 11, 224-228 (1994).

1.46. Tang, X. & Zheng, B. A PDMS viscometer for assaying endoglucanase activity. Analyst 136, 1222-1226 (2011).

1.47. Abbyad, P., Tharaux, P.-L., Martin, J.-L., Baroud, C. N. & Alexandrou, A. Sickling of red blood cells through rapid oxygen exchange in microfluidic drops. Lab Chip 10, 2505-9 (2010).

1.48. Dendukuri, D. et al. Modeling of Oxygen-Inhibited Free Radical Photopolymerization in a PDMS Microfluidic Device. Macromolecules 41, 8547-8556 (2008).

1.49. Jariwala, A. S. et al. Modeling effects of oxygen inhibition in mask-based stereolithography. Rapid Prototyping Journal 17, 168-175 (2011).

1.50. O'Brien, A. K. & Bowman, C. N. Impact of Oxygen on Photopolymerization Kinetics and Polymer Structure. Macromolecules 39, 2501-2506 (2006).

1.51. Grigoriev, R. O., Schatz, M. F. & Sharma, V. Chaotic mixing in microdroplets. Lab Chip 6, 1369-1372 (2006).

1.52. Ma, S., Sherwood, J. M., Huck, W. T. S. & Balabani, S. On the flow topology inside droplets moving in rectangular microchannels. Lab Chip 1-10 (2014). doi:10.1039/C4LC00671B 1.53. Andrzejewska, E. Photopolymerization kinetics of multifunctional monomers. Progress in Polymer Science 26, 605-665 (2001).

2.1 Laney M. Weber, Kirsten N. Hayda, and Kristi S. Anseth. Cell-Matrix Interactions Improve β-Cell Survival and Insulin Secretion in Three-Dimensional Culture Tissue Engineering Part A. December 2008, 14(12): 1959-1968. doi:10.1089/ten.tea.2007.0238. Published in Volume: 14 Issue 12: Nov. 19, 2008; Online Ahead of Print: Aug. 26, 2008.

2.2 Ross, A. B., & Neta, P. (1979). Rate constants for reactions of inorganic radicals in aqueous solution. Washington D. C: US Department of Commerce, National Bureau of Standards.

2.3 Bamford, C. H., & Dewar, M. J. S. (1949, August). The autoxidation of tetralin. In Proceedings of the Royal Society of London A: Mathematical, Physical and Engineering Sciences (Vol. 198, No. 1053, pp. 252-267). The Royal Society.

2.4 Mayo, F. R. (1968). Free radical autoxidations of hydrocarbons. Accounts of Chemical Research, 1(7), 193-201.

2.5 Ladygin, B. Y., Zimina, G. M., & Vannikov, A. V. (1984). KINETICS OF THE REACTIONS OF PEROXY-RADICALS FORMED BY THE ELECTRON-IRRADIATION OF NORMAL AND CYCLIC HYDROCARBONS IN THE PRESENCE OF OXYGEN. HIGH ENERGY CHEMISTRY, 18(4), 241-244.

2.6 Smaller, B., Remko, J. R., & Avery, E. C. (1968). ELECTRON PARAMAGNETIC RESONANCE STUDIES OF TRANSIENT FREE RADICALS PRODUCED BY PULSE RADIOLYSIS. Argonne National Lab., Ill.

2.7 Fairbanks, B. D., Schwartz, M. P., Bowman, C. N., & Anseth, K. S. (2009). Photoinitiated polymerization of PEG-diacrylate with lithium phenyl-2, 4, 6-trimethylbenzoylphosphinate: polymerization rate and cytocompatibility. Biomaterials, 30(35), 6702-6707.

2.8 Du, Y., Lo, E., Ali, S., & Khademhosseini, A. (2008). Directed assembly of cell-laden microgels for fabrication 2.9 Li, C. Y., Stevens, K. R., Schwartz, R. E., Alejandro, B. S., Huang, J. H., & Bhatia, S. N. (2014). Micropatterned cell-cell interactions enable functional encapsulation of primary hepatocytes in hydrogel microtissues. Tissue Engineering Part A, 20(15-16), 2200-2212.

2.10 Kubie, L. S. (1927). The solubility of o2, co2, and n2 in mineral oil and the transfer of carbon dioxide from oil to air. Journal of Biological Chemistry, 72(2), 545-548.

2.11 Vermuë, M., Tacken, M., & Tramper, J. (1994). Tetralin and oxygen transfer in the liquid-impelled loop reactor. Bioprocess Engineering, 11(6), 224-228.

2.12 Imlay, J. A., & Linn, S. (1988). DNA damage and oxygen radical toxicity. Science, 240(4857), 1302-1309.

2.13 Esterbauer, H., Gebicki, J., Puhl, H., & JUrgens, G. (1992). The role of lipid peroxidation and antioxidants in oxidative modification of LDL. Free Radical Biology and Medicine, 13(4), 341-390.

2.14 Stadtman, E. R., & Levine, R. L. (2003). Free radical-mediated oxidation of free amino acids and amino acid residues in proteins. Amino acids, 25(3-4), 207-218.

2.15 Brooker, R. J. (2009). Genetics: Analysis & principles. New York, N.Y.: McGraw-Hill.

2.16 Whittemore, E. R., Loo, D. T., Watt, J. A., & Cotmans, C. W. (1995). A detailed analysis of hydrogen peroxide-induced cell death in primary neuronal culture. Neuroscience, 67(4), 921-932.

2.17 Armstrong, D., & Browne, R. (1994). The analysis of free radicals, lipid peroxides, antioxidant enzymes and compounds related to oxidative stress as applied to the clinical chemistry laboratory. In Free radicals in diagnostic medicine (pp. 43-58). Springer US.

3.1. Peppas, N., Bures, P., Leobandung, W. & Ichikawa, H. Hydrogels in pharmaceutical formulations. European Journal of Pharmaceutics and Biopharmaceutics 50, 27-46 (2000).

3.2. Lebourg, M. et al. Biodegradable polycaprolactone scaffold with controlled porosity obtained by modified particle-leaching technique. J Mater Sci: Mater Med 19, 2047-2053 (2007).

3.3. LaNasa, S. M., Hoffecker, I. T. & Bryant, S. J. Presence of pores and hydrogel composition influence tensile properties of scaffolds fabricated from well-defined sphere templates. Journal of Biomedical Materials Research Part B: Applied Biomaterials 96B, 294-302 (2011).

3.4. Thorsen, T., Roberts, R. W., Arnold, F. H. & Quake, S. R. Dynamic Pattern Formation in a Vesicle-Generating Microfluidic Device. Phys. Rev. Lett. 86, 4163-4166 (2001).

3.5. Kloxin, A. M., Tibbitt, M. W. & Anseth, K. S. Synthesis of photodegradable hydrogels as dynamically tunable cell culture platforms. Nature Protocols 5, 1867-1887 (2010).

3.6. Fairbanks, B. D., Schwartz, M. P., Bowman, C. N. & Anseth, K. S. Photoinitiated polymerization of PEG diacrylate with lithium phenyl-2,4,6-trimethylbenzoylphosphinate: polymerization rate and cytocompatibility. Biomaterials 30, 6702-6707 (2009).

3.7. Vanapalli, S. A. et al. Fluidic Assembly and Packing of Microspheres in Confined Channels. Langmuir 24, 3661-3670 (2008).

3.8. Kumacheva, E., Garstecki, P., Wu, H. & Whitesides, G. M. Two-Dimensional Colloid Crystals Obtained by Coupling of Flow and Confinement. Phys. Rev. Lett. 91, 128301 (2003).

3.9. Zong, C. Sphere packings. (1999). doi:10.1007/b98975

3.10. Rohrer, G. S. Structure and Bonding in Crystalline Materials. (2001).

3.11. Karihaloo, B. L., Zhang, K. & Wang, J. Honeybee combs: how the circular cells transform into rounded hexagons. J R Soc Interface 10, 20130299-20130299 (2013).

5.1 S. Ansari, C. Chen, X. Xu, N. Annabi, H. H. Zadeh, B. M. Wu, A. Khademhosseini, S. Shi and A. Moshaverinia, Annals of Biomedical Engineering, 2016, 1-13.

5.2 S. J. Bryant, R. J. Bender, K. L. Durand and K. S. Anseth, *Biotechnol. Bioeng.*, 2004, 86, 747-755.

5.3 M. Kar, Y.-R. V. Shih, D. O. Velez, P. Cabrales and S. Varghese, *Biomaterials,* 2016, 77, 186-197.

5.4 P. E. Lacy, O. D. Hegre, A. Gerasimidi-Vazeou, F. T. GENTILE and K. E. Dionne, *Science,* 1991, 254, 1782-1784.

5.5 A. Murua, A. Portero, G. Orive, R. M. Hernandez, M. de Castro and J. L. Pedraz, *Journal of Controlled Release,* 2008, 132, 76-83.

5.6 A. J. Vegas, O. Veiseh, M. Gürtler, J. R. Millman, F. W. Pagliuca, A. R. Bader, J. C. Doloff, J. Li, M. Chen, K. Olejnik, H. H. Tam, S. Jhunjhunwala, E. Langan, S. Aresta-Dasilva, S. Gandham, J. J. McGarrigle, M. A. Bochenek, J. Hollister-Lock, J. Oberholzer, D. L. Greiner, G. C. Weir, D. A. Melton, R. Langer and D. G. Anderson, *Nat Med,* 2016, 22, 306-311.

5.7 J. Lam, E. C. Clark, E. L. S. Fong, E. J. Lee, S. Lu, Y. Tabata and A. G. Mikos, *Biomaterials,* 2016, 83, 332-346.

5.8 S. Subramaniam, Y.-H. Fang, S. Sivasubramanian, F.-H. Lin and C.-P. Lin, *Biomaterials,* 2016, 74, 99-108.

5.9 X. Guo, H. Park, S. Young, J. D. Kretlow, J. J. van den Beucken, L. S. Baggett, Y. Tabata, F. K. Kasper, A. G. Mikos and J. A. Jansen, *ACTA BIOMATERIALIA,* 2010, 6, 39-47.

5.10 M. D. LINDNER, S. R. WINN, E. E. BAETGE, J. P. HAMMANG, F. T. GENTILE, E. DOHERTY, P. E. MCDERMOTT, B. FRYDEL, M. D. ULLMAN, T. SCHALLERT and D. F. EMERICH, *Experimental Neurology,* 1995, 132, 62-76.

5.11 A. Monette, C. Ceccaldi, E. Assaad, S. Lerouge and R. Lapointe, *Biomaterials,* 2016, 75, 237-249.

5.12 P. D. BENYA and J. D. SHAFFER, *Cell,* 1982, 30, 215-224.

5.13 A. I. Chou and S. B. Nicoll, *J. Biomed. Mater. Res.,* 2009, 91A, 187-194.

5.14 C. M. Rubert Pérez, A. Panitch and J. Chmielewski, *Macromol. Biosci.,* 2011, 11, 1426-1431.

5.15 S.-Y. Choh, D. Cross and C. Wang, *Biomacromolecules,* 2011, 12, 1126-1136.

5.16 A. Priola, G. Gozzelino, F. Ferrero and G. Malucelli, *Polymer,* 1993, 34, 3653-3657.

5.17 D. Seliktar, *Science,* 2012, 1-6.

5.18 A. M. Kloxin, A. M. Kasko, C. N. Salinas and K. S. Anseth, *Science,* 2009.

5.19 D. S. W. Benoit, M. P. Schwartz, A. R. Durney and K. S. Anseth, *Nature Materials,* 2008, 7, 816-823.

5.20 L. M. Weber, K. N. Hayda, K. Haskins and K. S. Anseth, *Biomaterials,* 2007, 28, 3004-3011.

5.21 B. D. Fairbanks, M. P. Schwartz, C. N. Bowman and K. S. Anseth, *Biomaterials,* 2009, 30, 6702-6707.

5.22 M. J. Mahoney and K. S. Anseth, *Biomaterials,* 2006, 27, 2265-2274.

5.23 A. M. Kloxin, C. J. Kloxin, C. N. Bowman and K. S. Anseth, *Adv. Mater.,* 2010, 22, 3484-3494.

5.24 B. D. Fairbanks, M. P. Schwartz, A. E. Halevi, C. R. Nuttelman, C. N. Bowman and K. S. Anseth, *Adv. Mater.,* 2009, 21, 5005-5010.

5.25 C.-C. Lin and K. S. Anseth, *Adv. Funct. Mater.*, 2009, 19, 2325-2331.

5.26 A. K. O'Brien and C. N. Bowman, *Macromol. Theory Simul.*, 2006, 15, 176-182.

5.27 D. Dendukuri, P. Panda, R. Haghgooie, J. M. Kim, T. A. Hatton and P. S. Doyle, *Macromolecules*, 2008, 41, 8547-8556.

5.28 K. Krutkramelis, B. Xia and J. Oakey, *Lab Chip*, 2016, 1-9.

5.29 H. Wiseman and B. Halliwell, *Biochemical Journal*, 1996, 313, 17-29.

5.30 E. Cabiscol, J. Tamarit and J. Ros, *International Microbiology*, 2010, 3, 3-8.

5.31 C. E. Hoyle and C. N. Bowman, *Angew. Chem. Int. Ed.*, 2010, 49, 1540-1573.

5.32 C.-C. Lin, A. Raza and H. Shih, *Biomaterials*, 2011, 32, 9685-9695.

5.33 A. K. O'Brien, N. B. Cramer and C. N. Bowman, *J. Polym. Sci. A Polym. Chem.*, 2006, 44, 2007-2014.

5.34 J. J. Roberts and S. J. Bryant, *Biomaterials*, 9999, 34, 9969-9979.

5.35 V. K. Yadavalli, W.-G. Koh, G. J. Lazur and M. V. Pishko, *Sensors and Actuators B: Chemical*, 2004, 97, 290-297.

5.36 Y. Lu, G. Mapili, G. Suhali, S. Chen and K. Roy, *J. Biomed. Mater. Res.*, 2006, 77A, 396-405.

5.37 R. Gref, Y. Minamitake, M. T. Peracchia, V. Trubetskoy, V. Torchilin and R. Langer, *Science*, 1994, 263, 1600-1603.

5.38 C. Siltanen, M. Yaghoobi, A. Hague, J. You, J. Lowen, M. Soleimani and A. Revzin, *ACTA BIOMATERIALIA*, 2016, 1-8.

5.39 S. Gobaa, S. Hoehnel, M. Roccio, A. Negro, S. Kobel and M. P. Lutolf, *Nat Meth*, 2011, 8, 949-955.

5.40 P. Panda, S. Ali, E. Lo, B. G. Chung, T. A. Hatton, A. Khademhosseini and P. S. Doyle, *Lab Chip*, 2008, 8, 1056-6.

5.41 D. K. Hwang, J. Oakey, M. Toner, J. A. Arthur, K. S. Anseth, S. Lee, A. Zeiger, K. J. Van Vliet and P. S. Doyle, *J. Am. Chem. Soc.*, 2009, 131, 4499-4504.

5.42 A. Reece, B. Xia, Z. Jiang, B. Noren, R. McBride and J. Oakey, *Current Opinion in Biotechnology*, 2016, 40, 90-96.

5.43 A. M. Klein, L. Mazutis, I. Akartuna, N. Tallapragada, A. Veres, V. Li, L. Peshkin, D. A. Weitz and M. W. Kirschner, *Cell*, 2015, 161, 1187-1201.

5.44 E. Z. Macosko, A. Basu, R. Satija, J. Nemesh, K. Shekhar, M. Goldman, I. Tirosh, A. R. Bialas, N. Kamitaki, E. M. Martersteck, J. J. Trombetta, D. A. Weitz, J. R. Sanes, A. K. Shalek, A. Regev and S. A. McCarroll, *Cell*, 2015, 161, 1202-1214.

5.45 B. Xia, K. Krutkramelis and J. Oakey, *Biomacromolecules*, 2016, 17, 2459-2465.

5.46 T. Majima, W. Schnabel and W. Weber, *Die Makromolekulare Chemie*, 1991, 192, 2307-2315.

5.47 H. Shih and C.-C. Lin, *Biomacromolecules*, 2012, 13, 2003-2012.

5.48 Y. Xia and G. M. Whitesides, *Annual review of materials science*, 1998, 28, 153-184.

5.49 F. Yang, C. G. Williams, D.-A. Wang, H. Lee, P. N. Manson and J. Elisseeff, *Biomaterials*, 2005, 26, 5991-5998.

5.50 S. B. Anderson, C.-C. Lin, D. V. Kuntzler and K. S. Anseth, *Biomaterials*, 2011, 32, 3564-3574.

5.51 Z. Muñoz, H. Shih and C.-C. Lin, *Biomaterials Science*, 2014, 2, 1063-11.

5.52 H. Shiku, T. Saito, C.-C. Wu, T. Yasukawa, M. Yokoo, H. Abe, T. Matsue and H. Yamada, *Chem. Lett.*, 2006, 35, 234-235.

5.53 J. G. Riess and M. Le Blanc, *Pure and Applied Chemistry*, 1982, 54, 2383-2406.

We claim:

1. A method of preparing a plurality of microparticles in a microfluidics device in an oxygen-controlled environment comprising the steps of:
   (a) providing a continuous phase comprising a non-aqueous liquid and an aqueous phase comprising a polyethylene glycol (PEG)-based photodegradable macromer having a molecular weight selected from the range of 200 to 20,000 Daltons, a biological material, and an initiator;
   (b) forming a composition comprising microdroplets of said aqueous phase dispersed in said non-aqueous liquid;
   (c) controlling oxygen concentration in the microdroplets to enhance viability of the biological material, wherein the controlling comprises:
      (i) providing said composition comprising said microdroplets and said non-aqueous liquid in a first channel of said microfluidics device;
      (ii) flowing said oxygen-free gas through a second channel, adjacent to said first channel;
      (iii) diffusing at least some of said oxygen-free gas into a region of the microfluidics device between the first and second channels; and
      (iv) varying a supply pressure of the oxygen-free gas in order to vary the oxygen concentration within the microdroplets; and
   (d) partially polymerizing said monomer or said macromer in said microdroplets, wherein, as polymerization is impeded by dissolved oxygen, only a fraction of a radial volume of each microdroplet is polymerized and the rest remains as a liquid film of un-polymerized aqueous phase on a polymerized core thereby generating microparticles within said aqueous phase having a smaller radius than said microdroplets; wherein the partially polymerizing step is at least partially controlled via the controlling oxygen concentration step (c); and wherein the microparticles have a mean diameter of less than or equal to 1000 μm.

2. The method of claim 1, wherein said oxygen-free gas is nitrogen.

3. The method of claim 1, wherein said oxygen-free gas is varied within the range of 0.1 atm to 10 atm.

4. The method of claim 1, where said initiator is a photoinitiator and said step of polymerizing said monomer or macromer is carried out in the presence of ultraviolet light.

5. The method of claim 4, wherein said photoinitiator is lithium phenyl-2,4,6-trimethylbenzoylphosphinate (LAP) or Irgacure 1173.

6. The method of claim 1, wherein said non-aqueous liquid comprises a fluorocarbon oil.

7. The method of claim 6, wherein said fluorocarbon oil is a segregated hydrofluoroether.

8. The method of claim 1, wherein said non-aqueous liquid further comprises a surfactant and said surfactant is provided at a concentration selected from the range of 0.1% to 4%.

9. The method of claim 8, wherein said surfactant is a Dolomite FluoroPEG surfactant, RAN Biotechnologies FluoroPEG surfactant or Krytox FSL 157.

10. The method of claim 1, wherein said microparticles are hydrogel microparticles.

11. The method of claim 1, wherein said microparticles are photodegradable.

12. The method of claim 1, wherein said macromer is a PEG-diacrylate (PEGDA) macromer.

13. The method of claim 1, wherein said step (c) of controlling oxygen concentration in the microdroplets reduces the amount of oxygen in the composition to a preselected concentration selected from the range of 1% to 90%.

14. The method of claim 1, wherein said step(c) of controlling oxygen concentration in the microdroplets reduces the amount of oxygen in the non-aqueous liquid to a preselected concentration selected from the range of 1% to 90%.

15. The method of claim 1, wherein said step (c) of controlling oxygen concentration in the microdroplets comprises providing a membrane between said composition and said oxygen-free gas.

16. The method of claim 15, wherein said membrane is a polydimethylsiloxane membrane.

17. The method of claim 1, further comprising the steps of:
 (e) at least partially encapsulating said microparticles within a non-photodegradable polymer, wherein said microparticles are photodegradable; and
 (f) photodegrading said photodegradable microparticles to produce a composite porous hydrogel.

18. The method of claim 1, wherein said biological material comprises cells.

19. The method of claim 18, wherein said pores of said composite porous hydrogel have a lateral dimension to receive an individual cell.

20. The method of claim 1 wherein said biological material is selected from the group consisting of: mesenchymal stem cells, ß cells, satellite muscle cells, proteins, therapeutic small molecules, imaging molecules, secondary nanoparticles and any combination thereof.

21. The method of claim 1, wherein said composition is a water in oil emulsion.

22. The method of claim 1, wherein said microparticles are photodegradable microparticles and further comprising:
 (e) at least partially encapsulating said photodegradable microparticles within a non-photodegradable polymer;
 (f) photodegrading said photodegradable microparticles to produce a composite porous hydrogel; and
 (g) contacting said composite porous hydrogel with a biological material, thereby capturing a portion of said biologically material in said composite porous hydrogel.

23. The method of claim 1, wherein the step of regulating oxygen exposure (c)(iv) comprises varying a residence time of the microdroplets in the first channel of said microfluidics device.

24. The method of claim 18, comprising tuning viability of the cells via the step of controlling oxygen concentration in the microdroplets.

25. The method of claim 1 comprising removing the un-polymerized liquid film from the microparticles.

26. The method of claim 1 comprising removing the non-aqueous phase from the microparticles to induce self-assembly of a hexagonal matrix of microparticles surrounded by un-polymerized aqueous phase.

27. The method of claim 26 comprising polymerizing the un-polymerized aqueous phase of the hexagonal matrix to form an ordered structure.

* * * * *